(12) United States Patent  (10) Patent No.: US 8,357,169 B2
Henniges et al.  (45) Date of Patent: Jan. 22, 2013

(54) SYSTEM AND METHOD FOR DELIVERING AN AGGLOMERATION OF SOLID BEADS AND CEMENT TO THE INTERIOR OF A BONE IN ORDER TO FORM AN IMPLANT WITHIN THE BONE

(75) Inventors: Bruce D. Henniges, Galesburg, MI (US); Richard F. Huyser, Kalamazoo, MI (US); Douglas L. Tyler, Paw Paw, MI (US); Karen Smit, Kalamazoo, MI (US)

(73) Assignee: Spinal Ventures, LLC, Brighton, MI (US)

( * ) Notice: Subject to any disclaimer, the term of this patent is extended or adjusted under 35 U.S.C. 154(b) by 1453 days.

(21) Appl. No.: 11/754,120

(22) Filed: May 25, 2007

(65) Prior Publication Data

US 2008/0009792 A1 Jan. 10, 2008

(51) Int. Cl.
*A61B 17/58* (2006.01)
(52) U.S. Cl. .......................... 606/94; 606/92
(58) Field of Classification Search ............. 606/92–94
See application file for complete search history.

(56) References Cited

U.S. PATENT DOCUMENTS

| | | | |
|---|---|---|---|
| 834,261 A | 10/1906 | Chambers | |
| 1,347,622 A | 7/1920 | Deininger | |
| 1,596,754 A | 8/1926 | Moschelle | |
| 2,659,369 A | 11/1953 | Lipman | |
| 4,270,675 A | 6/1981 | Wicks et al. | |
| 4,451,253 A | 5/1984 | Harman | |
| 4,966,601 A * | 10/1990 | Draenert | 606/92 |
| 5,288,291 A | 2/1994 | Teoh | |
| 5,431,654 A | 7/1995 | Nic | |
| 5,514,101 A | 5/1996 | Schulz et al. | |
| 5,638,997 A | 6/1997 | Hawkins et al. | |
| 5,702,454 A | 12/1997 | Baumgartner | |
| 5,755,797 A | 5/1998 | Baumgartner | |
| 5,756,127 A | 5/1998 | Grisoni et al. | |
| 5,893,488 A | 4/1999 | Hoag et al. | |
| 6,139,320 A | 10/2000 | Hahn | |
| 6,241,734 B1 | 6/2001 | Scribner et al. | |
| 6,340,299 B1 | 1/2002 | Saito | |
| 6,387,130 B1 | 5/2002 | Stone et al. | |
| 6,595,998 B2 | 7/2003 | Johnson et al. | |
| 6,613,054 B2 | 9/2003 | Scribner et al. | |
| 7,351,262 B2 | 4/2008 | Bindseil et al. | |
| 7,682,400 B2 | 3/2010 | Zwirkoski | |
| 7,803,188 B2 | 9/2010 | Justis et al. | |
| 7,935,121 B2 * | 5/2011 | Lidgren et al. | 606/92 |
| 8,034,109 B2 | 10/2011 | Zwirkoski | |
| 2004/0024409 A1 | 2/2004 | Sand et al. | |
| 2004/0052829 A1 | 3/2004 | Shimp | |
| 2004/0215343 A1 | 10/2004 | Hochschuler et al. | |

(Continued)

FOREIGN PATENT DOCUMENTS

DE 10309986 A1 9/2004
WO WO-0247563 A1 6/2002
WO WO 2005044154 A1 * 5/2005

*Primary Examiner* — Nicholas Woodall

(57) ABSTRACT

A system for forming an implant to stabilize an interior of a vertebral body is provided. The system includes a delivery cannula (18) in which there is an agglomeration of beads (20) and cement (22). A membrane is disposed over the open end of the cannula. When the agglomeration is discharged from the cannula it fills the membrane. The membrane thus forms the outer shell of the implant internal to the bone.

15 Claims, 55 Drawing Sheets

U.S. PATENT DOCUMENTS

| | | |
|---|---|---|
| 2005/0033265 A1 | 2/2005 | Engel et al. |
| 2005/0244451 A1 | 11/2005 | Diaz et al. |
| 2005/0278023 A1 | 12/2005 | Zwirkoski |
| 2006/0184246 A1* | 8/2006 | Zwirkoski ................. 623/11.11 |
| 2006/0265077 A1 | 11/2006 | Zwirkoski |
| 2007/0162132 A1 | 7/2007 | Messerli |
| 2007/0233146 A1 | 10/2007 | Henniges et al. |

* cited by examiner

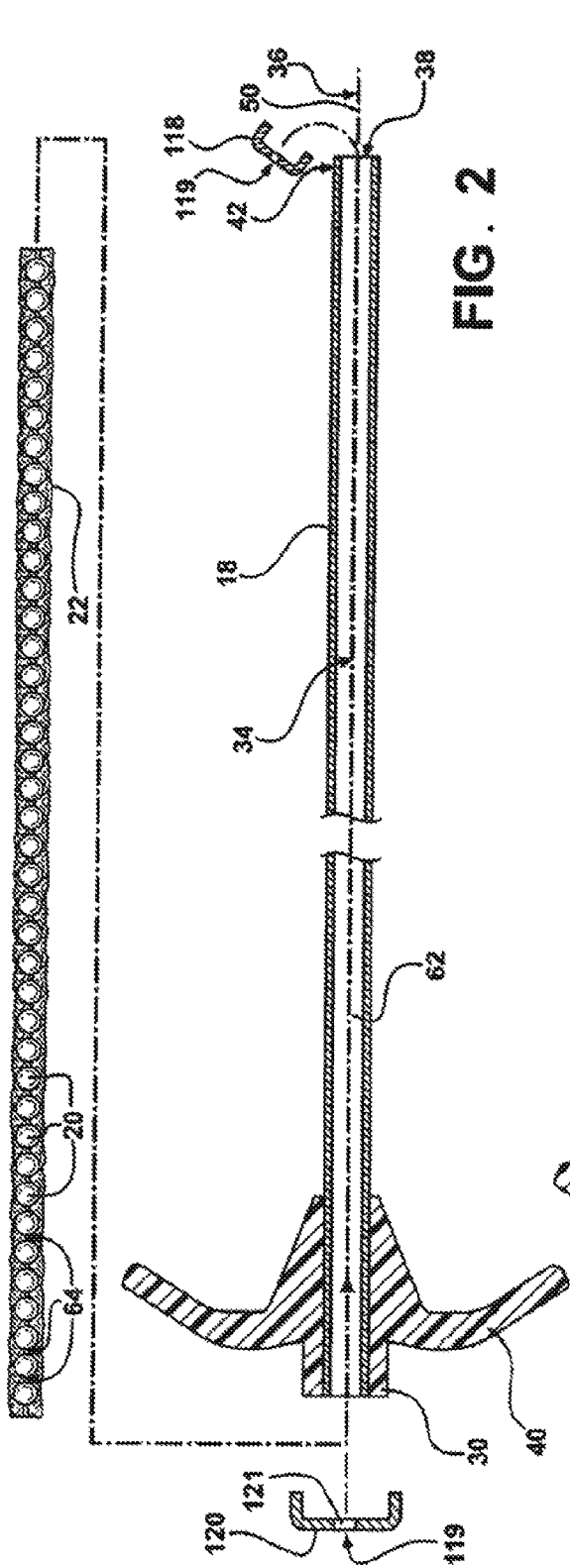
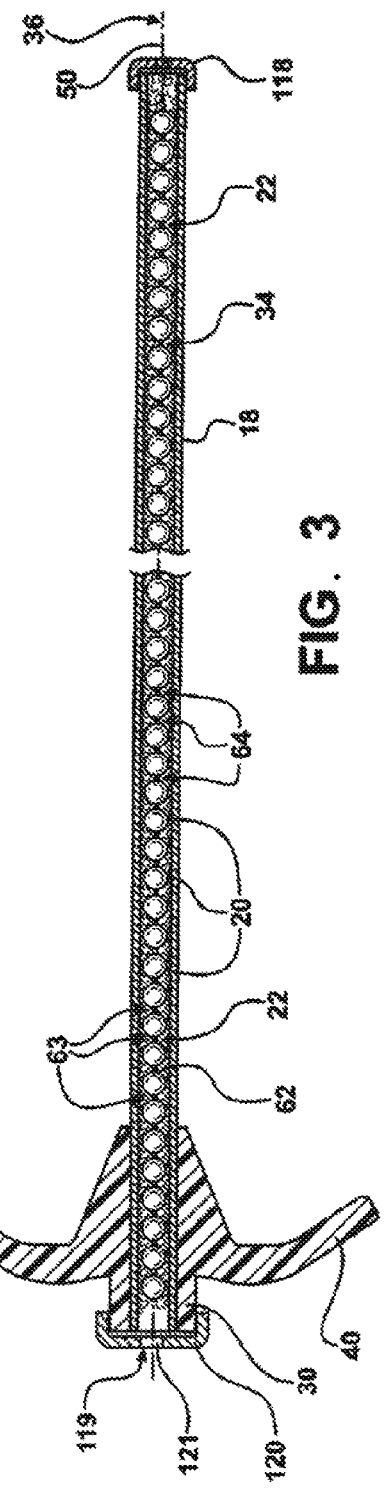

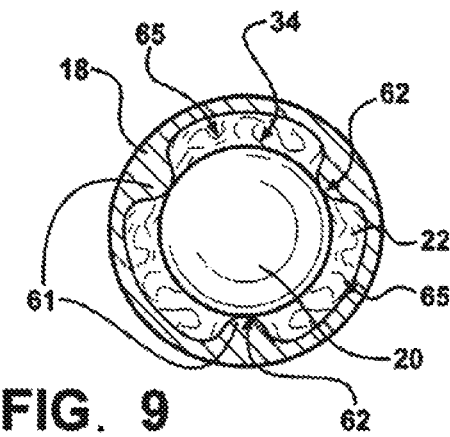
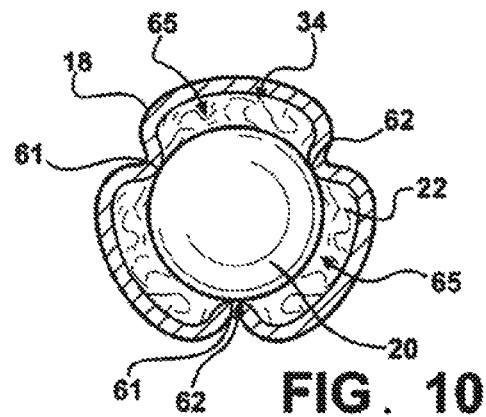
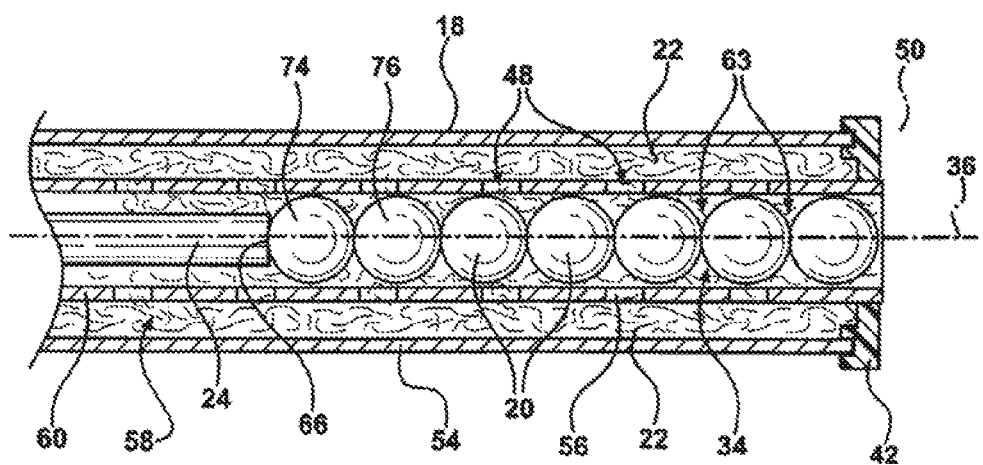

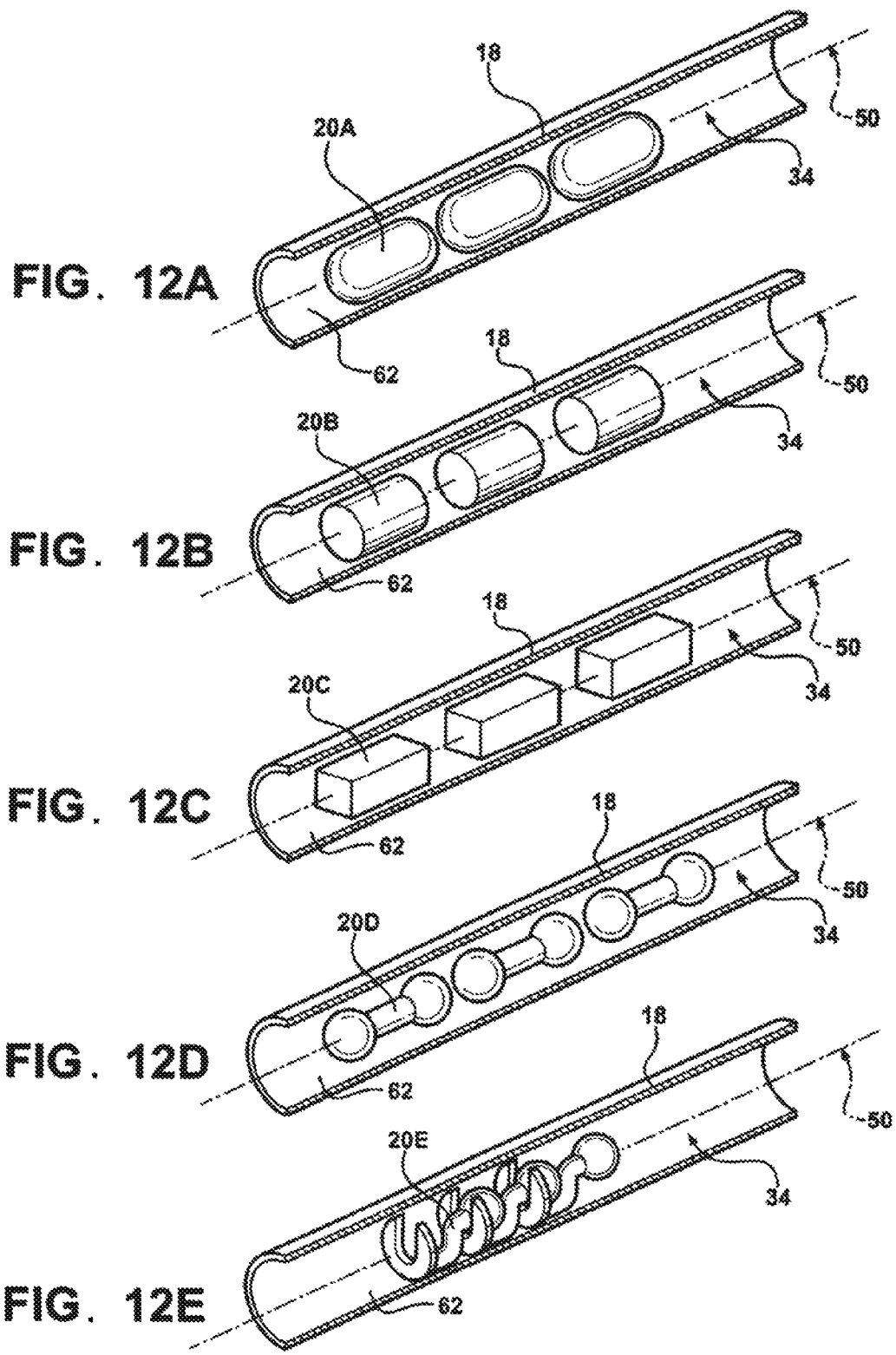

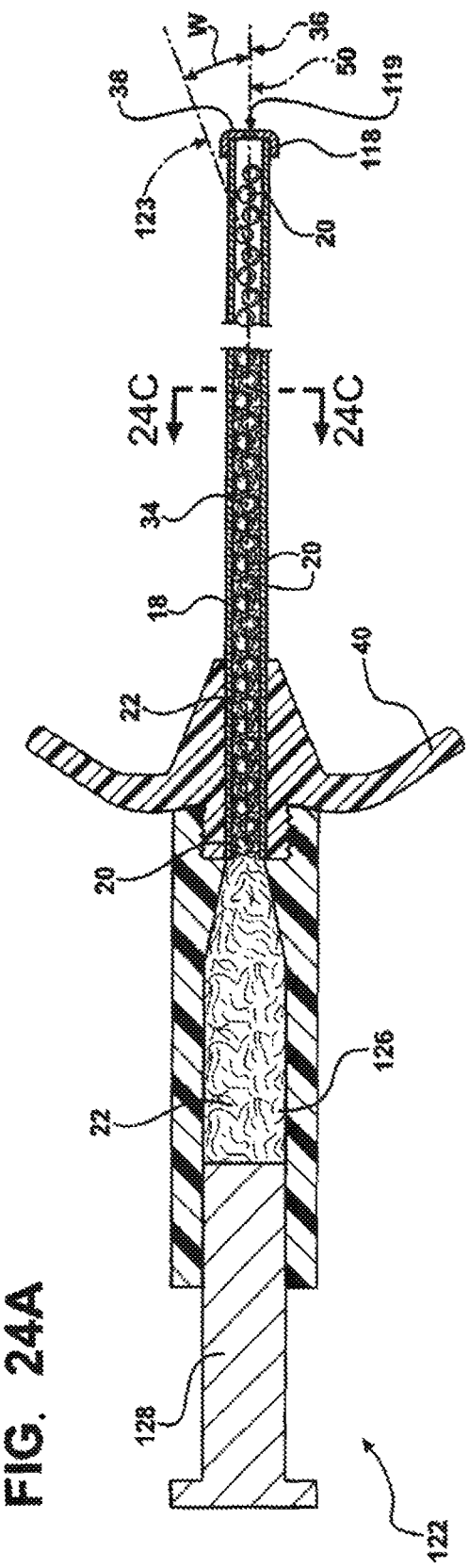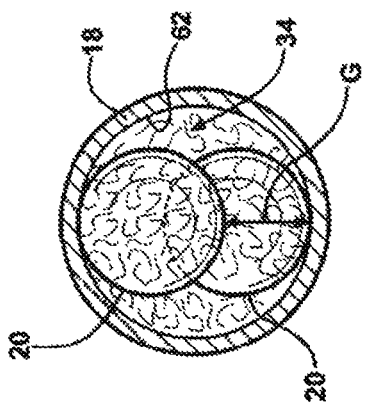
FIG. 24A
FIG. 24C

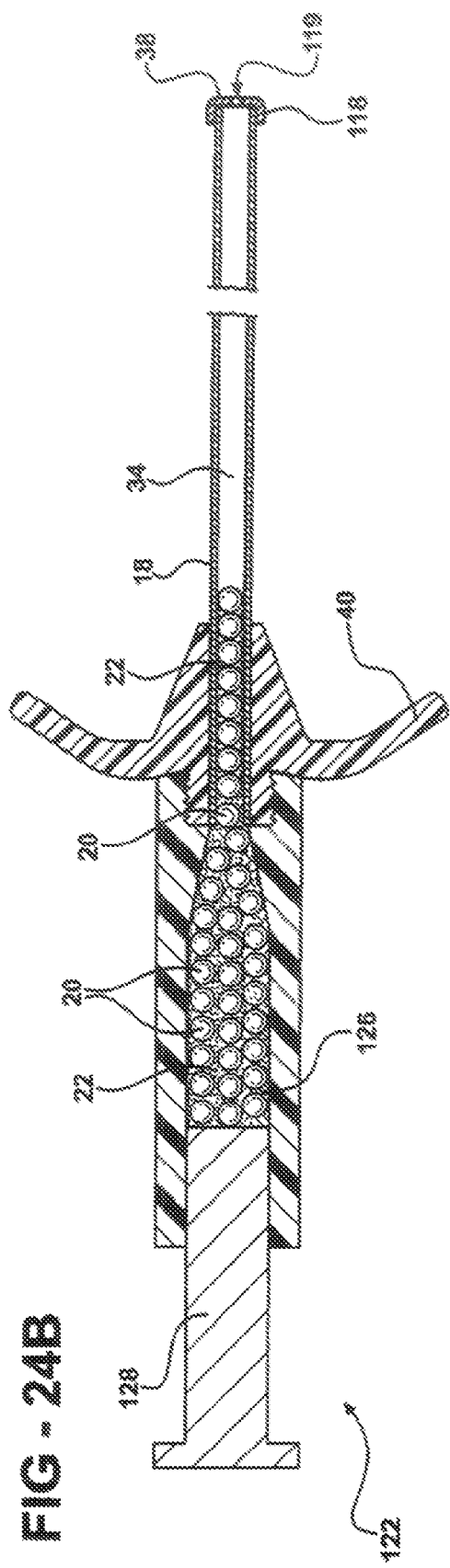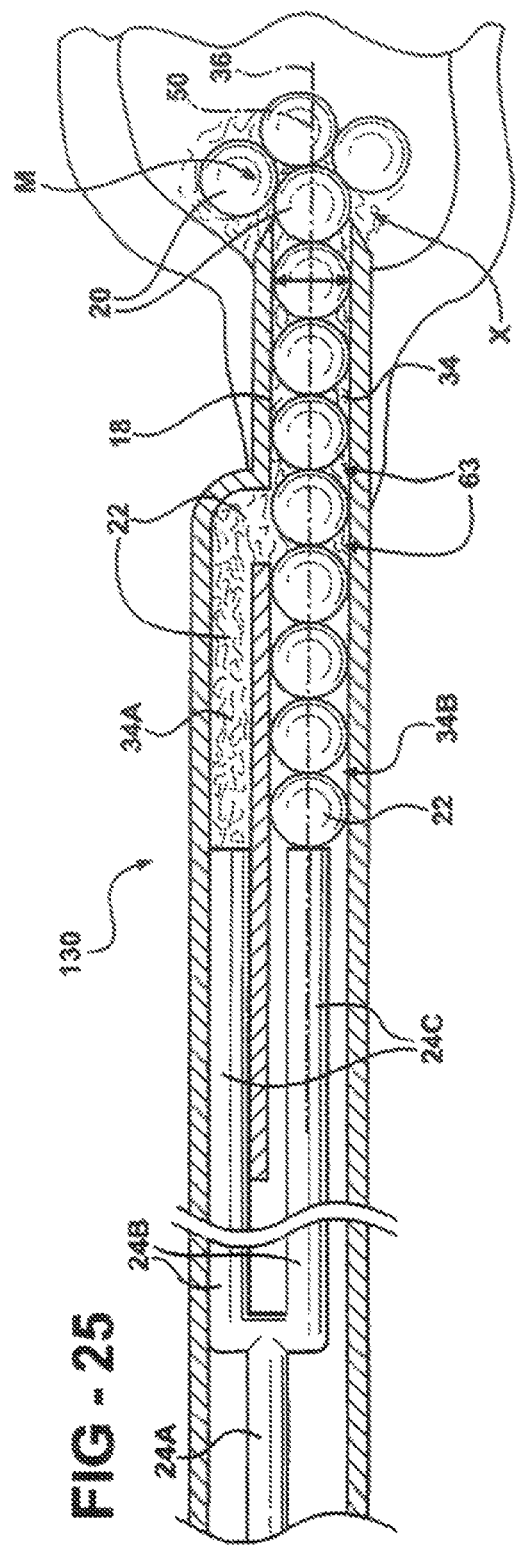
FIG - 24B
FIG - 25

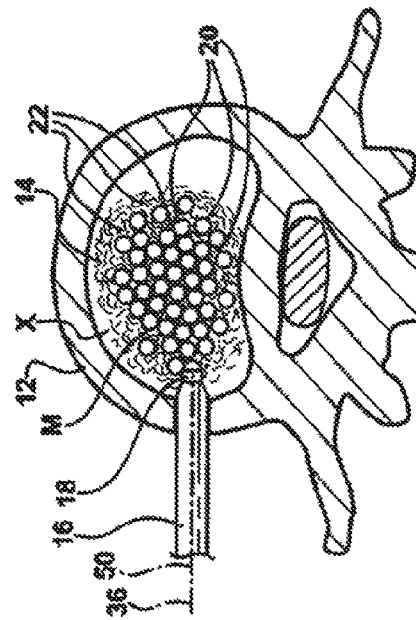
FIG. 26A
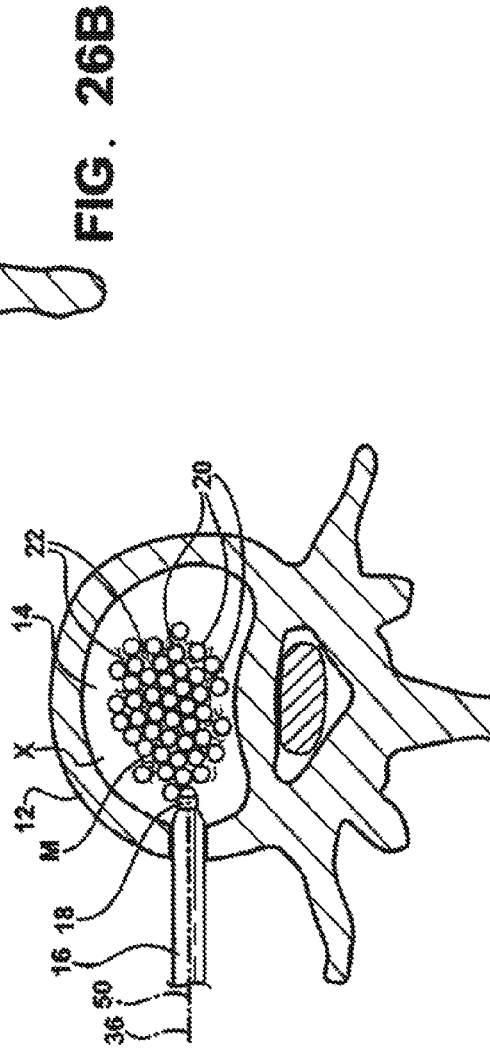
FIG. 26B
FIG. 26C
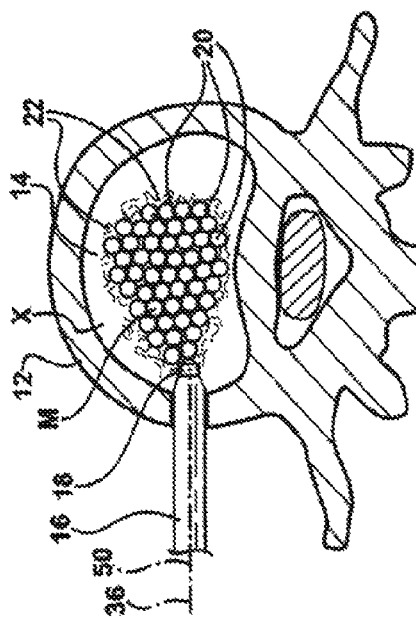

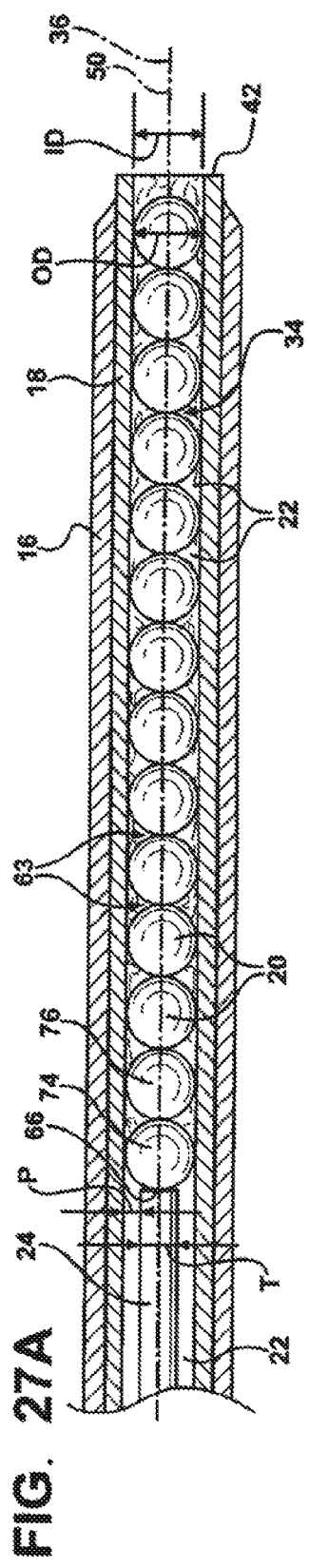 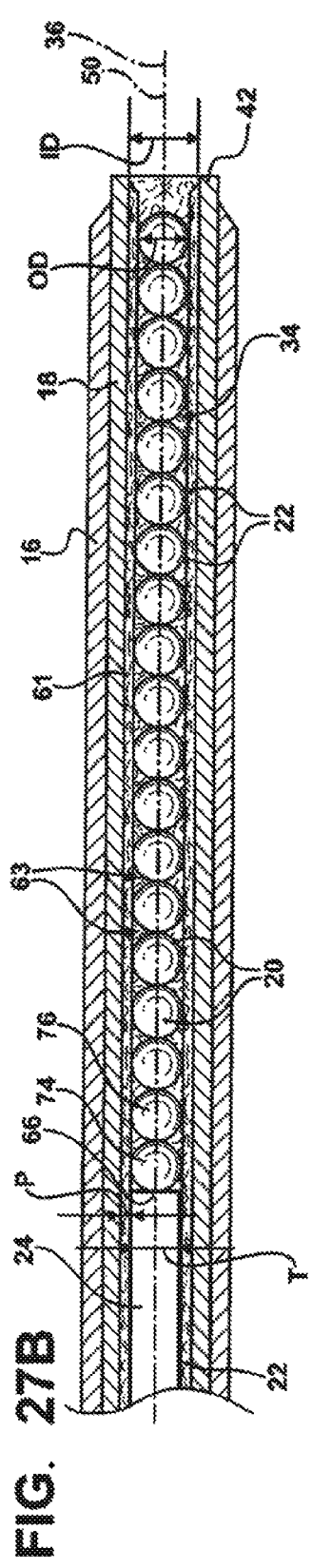 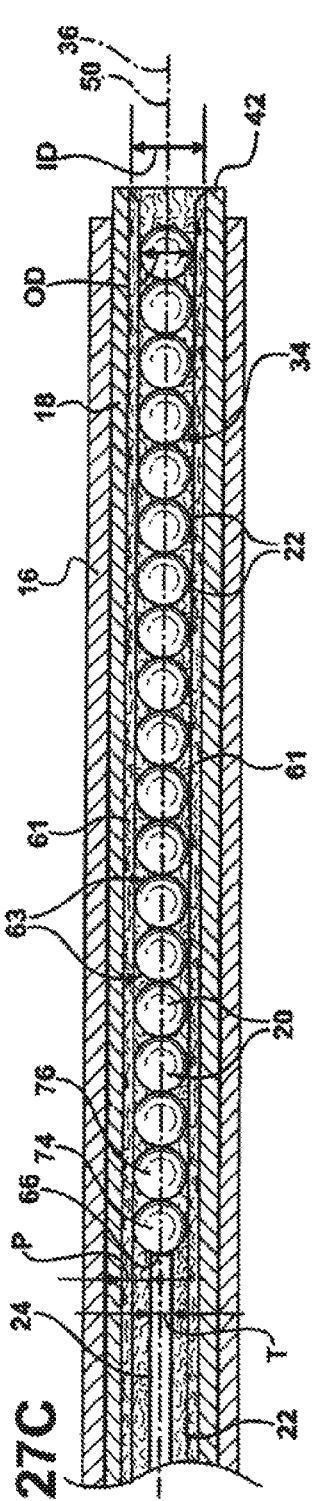

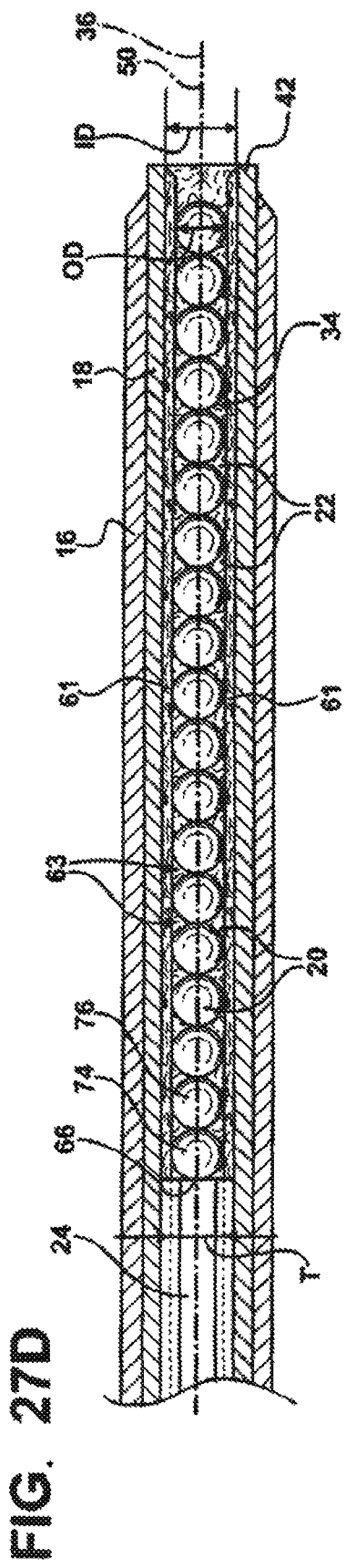
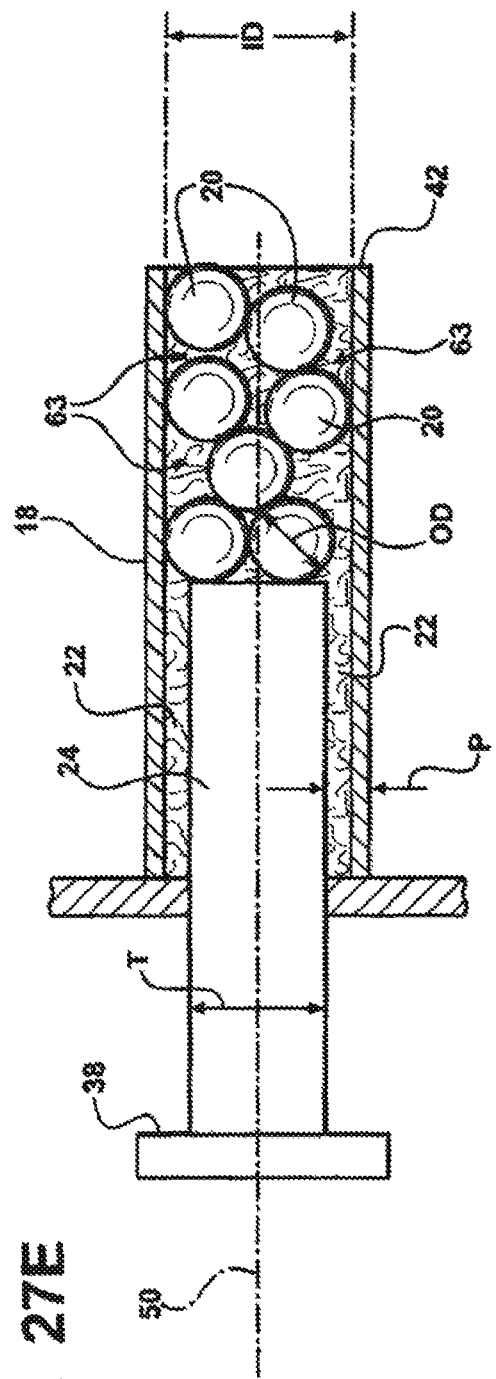
FIG. 27D
FIG. 27E

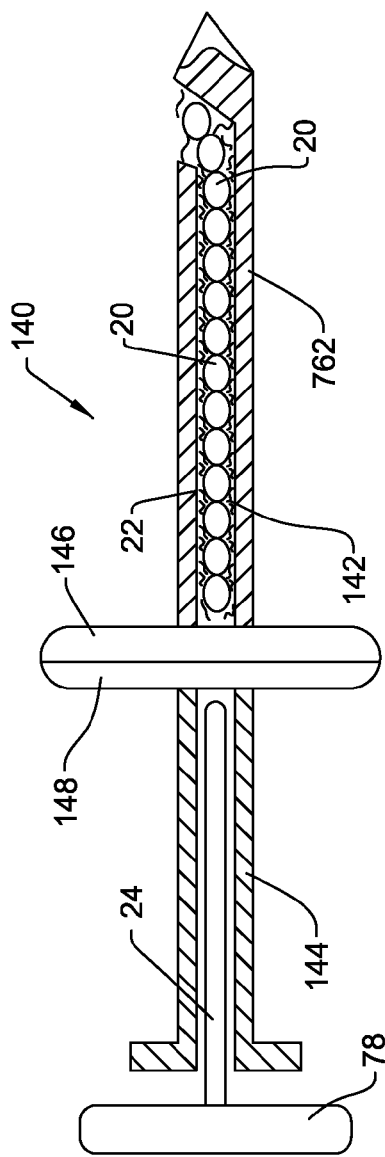
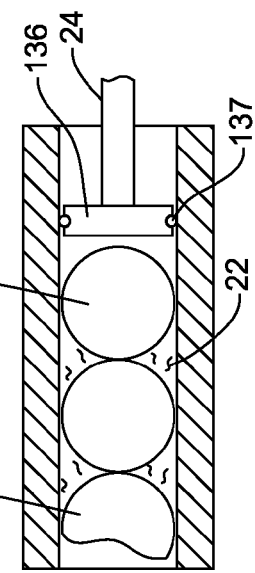
FIG. 29
FIG. 28A

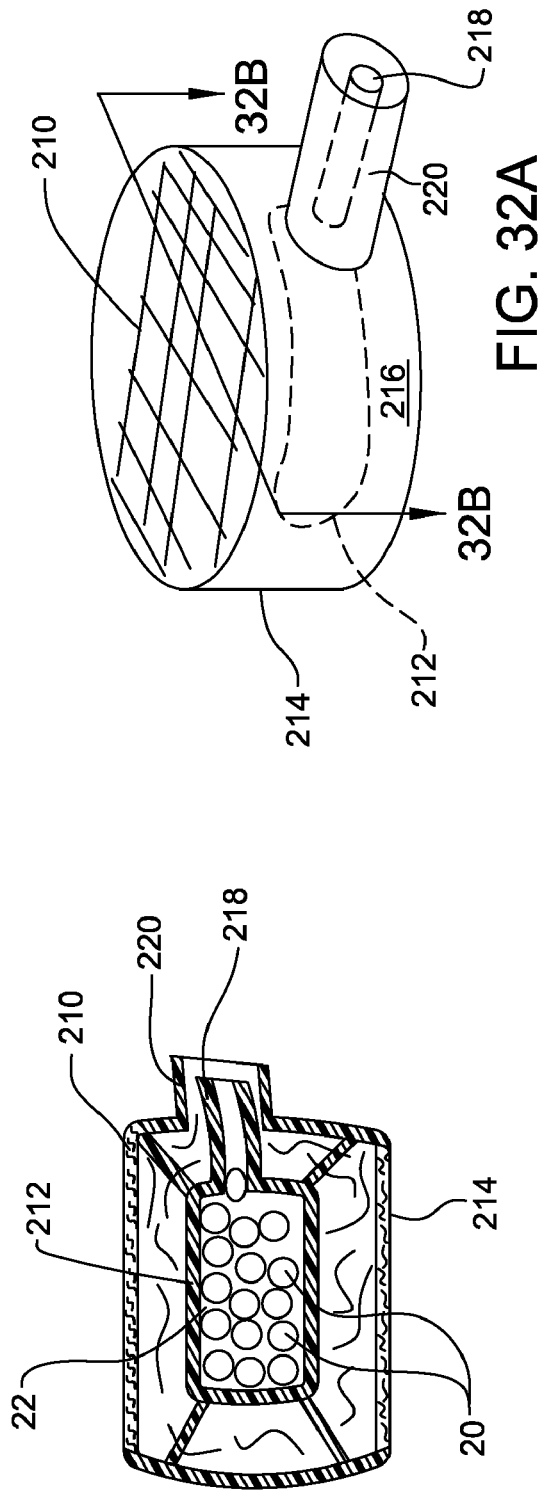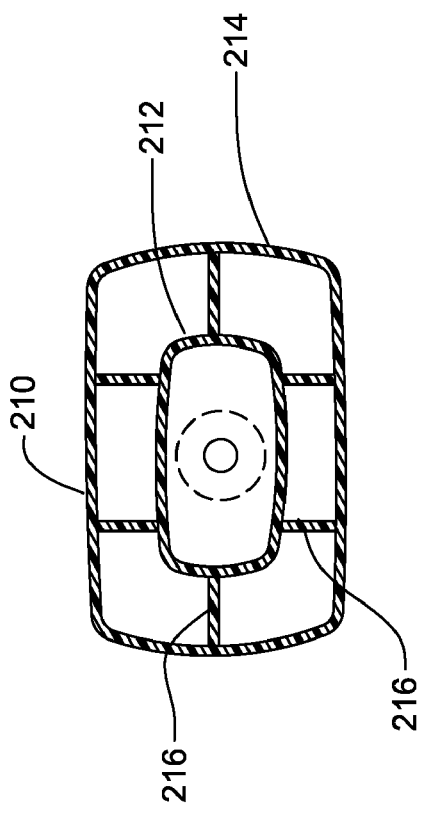
FIG. 32A
FIG. 32B
FIG. 32C

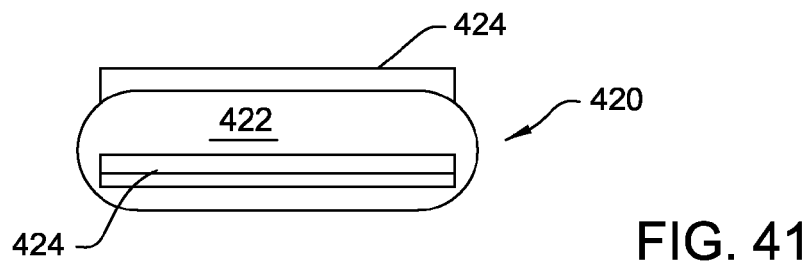
FIG. 41
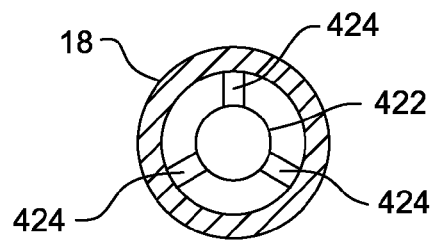
FIG. 42
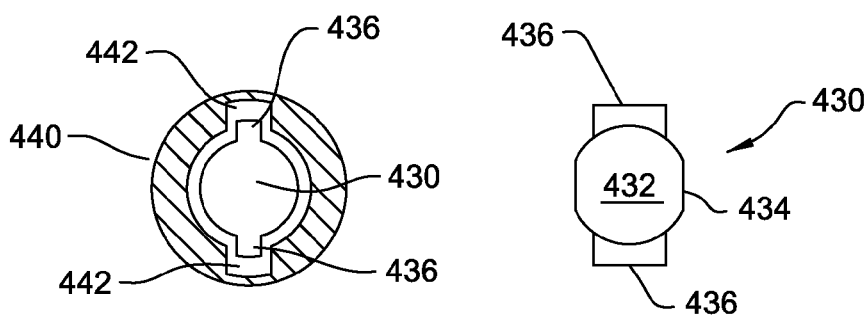
FIG. 43                    FIG. 44
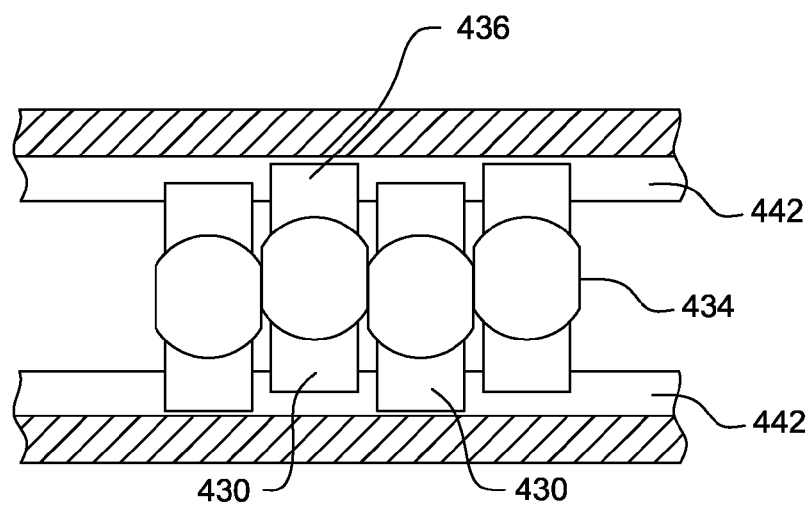
FIG. 45

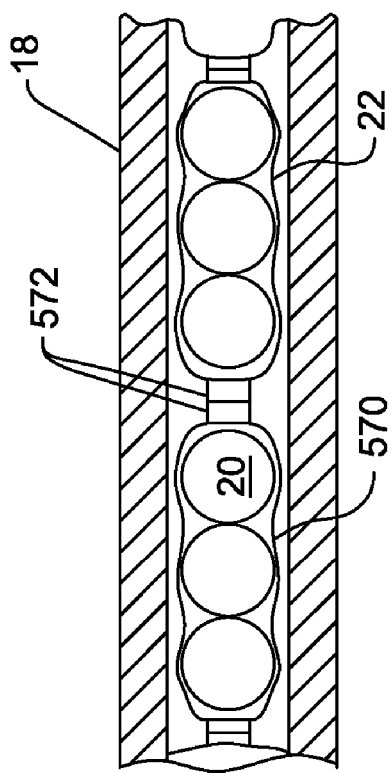
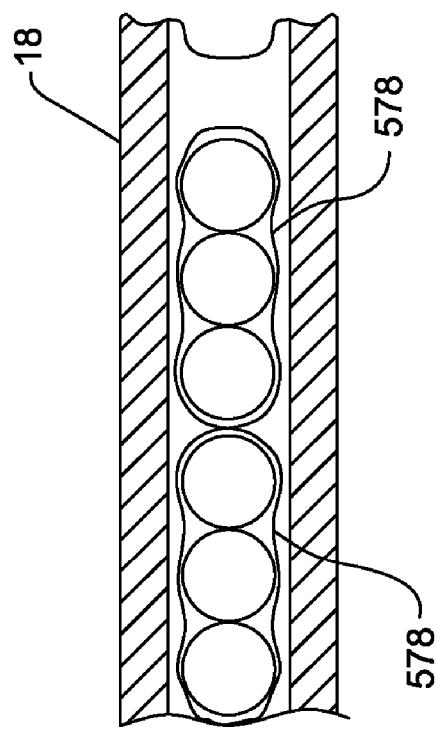

SYSTEM AND METHOD FOR DELIVERING AN AGGLOMERATION OF SOLID BEADS AND CEMENT TO THE INTERIOR OF A BONE IN ORDER TO FORM AN IMPLANT WITHIN THE BONE

CROSS REFERENCE TO RELATED APPLICATIONS

U.S. patent application Ser. No. 11/627,771 filed Jan. 26, 2007, U.S. Provisional Patent Application Ser. No. 60/762,779, filed on Jan. 27, 2006, and U.S. Provisional Patent Application Ser. No. 60/808,681, filed on May 26, 2006 are hereby incorporated by reference.

FIELD OF THE INVENTION

The invention generally relates to a system and a method for delivering a mixture, an agglomeration of solid beads and liquid-state cement for implantation into a bone. More particularly, this invention relates to a system and method for delivering the mixture of solids and cements so as to minimize the uncontrolled flow of cement out of the space into which it is delivered.

BACKGROUND OF THE INVENTION

Systems are well known in the art for delivering materials such as bone cement to a target site for medical treatment. One particular use of these types of systems is to treat compression fractures caused by trauma, metastasis, or osteoporosis. A compression fracture occurs when a normal vertebral body of a spine has collapsed or compressed from its original anatomical size. Typically, these vertebrae fail at an anterior cortical wall causing a wedge shaped collapse of the vertebra. Fractures can be painful for the patient typically causing a reduced quality of life. Treatments to repair these fractures are performed to reinforce the fractured bone, alleviate associated pain, and to prevent further vertebral collapse.

A common means to treat this condition is to insert cement into the vertebra in order to stabilize the bone. This procedure is generally referred as a vertebroplasty procedure. One type of vertebroplasty procedure is balloon-assisted vertebroplasty. In this procedure, fluoroscopy is used to establish a percutaneous passage in the bone or vertebral body to be treated. This is followed by the insertion of an inflatable balloon-like device into the passage in the vertebral body. Liquids, typically called contrast media, are used to inflate the balloon-like device to compact the cancellous bone about the balloon and/or bone marrow toward the inner cortical wall of the vertebral body, thereby resulting in an enlargement of the passage creating a cavity. The balloon-like device is then deflated and removed from the vertebral cavity, leaving behind a cavity. A biocompatible filling material, such as polymethylmethacrylate (PMMA) bone cement is then delivered while in its flowable form into the cavity. This delivery is performed by using pressure type devices. The filling material is then allowed to set to a hardened condition to provide internal structural support to the bone.

Balloon-like devices require exertion of pressure for expansion of the balloon and/or insertion of flowable materials into the balloon. These balloon-like devices can require high inflation pressures, sometimes as high as 400 psi., obtain the desired cavity size or compaction. These balloon-like devices have been known to fail during inflation due to the high inflation pressures, thin balloon membranes required to fit into the percutaneous passage, and sharp tools or bony structures piercing the membranes. Other mechanical devices have been suggested in order to tamp the bone and create a cavity for subsequent filling with bone cement. In today's art, filling the cavity created by a balloon or tamping device requires applying a pressure to the flowable material. Syringe-like devices are typically used to create the pressure to flow the cement from a chamber and down a channel into the bone. Once the flowable materials leave the delivery system, they flow toward lower pressure regions along the path of least resistance until the pressure has neutralized with its surroundings. This action can occur in an uncontrollable manner where the user cannot influence the direction of the flow. These cements have been know to flow along fracture lines, into vascular structure as well as into other cracks, holes or spaces in the bone that may or may not have been known to the practitioner.

Other vertebroplasty procedures do not employ balloon-type devices to create a void space in the vertebra into which the cement is flowed. Typically, though the procedure is performed under fluoroscopic guidance and includes the placement of a cannula into the vertebral body to provide a pathway for the bone cement to enter the vertebral body. During these procedures, the pressure head of the cement, compresses the cancellous bone, the sponge-like inner bone. Again, due to the high pressure under which this cement is introduced into the bone, the cement ill flow along the path of least resistance. In some instances this leads to undesirable leaking or extravasations outside of the vertebral body.

Usually these cement leaks do not result in undesirable side effects that require additional medical intervention. However, occasionally complications have arisen as a result of these cement leaks outside of the vertebral body. Such side effects include: epidural hematoma; development of a radiculopathy, or paresthesias. These side effects can result in loss of neurological function or even result in a pulmonary embolism.

Another limitation of the current pressure delivery system is the difficulty of visualizing the flowable materials using a fluoroscope. Fluoroscopes are traditionally used by the medical practitioner in order to identify the bony structure, the radiopaque instruments used and the radiopaque flowable materials injected as described above. As mentioned earlier, the practitioner cannot influence the flow of the materials. Once the materials have left the delivery system, these materials can flow through thin cracks or small crevices in a manner where the practitioner cannot see the image of this thin flow on the fluoroscope. As one can appreciate, the inability to see thin flow fronts can mislead the practitioner into applying more pressure to deliver more flowable materials, even when the thin flow fronts are leaking outside the vertebral body and into undesirable locations. An example of a filling material for use in vertebroplasty to overcome these problems can be found in U.S. Pat. No. 6,231,615 to Preissman. Preissman discloses an enhanced visibility composition of a flowable material with radiopaque particles up to 350 (micron) and tracer elements having a size between 570 (micron) and 2200 (micron) for improving the visualization with medical imaging. Preissman, however, did not consider the problem when thin flow fronts exist and the disclosed tracers are separated from the flow when the bony structure restrains the tracers, effectively filtering them, as the flow continues down thin sections.

Recently, in an attempt to overcome these problems, systems have been developed to treat compression fractures by delivering structural elements to distract tissue surfaces forming the collapsed vertebral body. A shortcoming of these systems is the lack of complete stabilization of the bony structure and the lack of a permanent fixation of the implant M to the bone. It is believed that motion of a bony structure of cancellous bone within the vertebral body may result in pain to the patient. Thus, it is desirable to stabilize the cancellous bone to prevent this motion.

U.S. Pat. No. 6,595,998 to Johnson et al. discloses a tissue distraction device for treating compression fractures by inserting a plurality of wafers into a vertebral body to form a wafer stack. Once the wafer stack is formed, the bone cement can be delivered into the vertebral body around the wafer stack to lock the wafers together and form a stable implant M. The wafer stack provides support on upper and lower sides of the vertebral body, but may not provide uniform support on all sides. Also, Johnson et al. does not disclose how much bone cement is delivered and/or whether enough is delivered to stabilize the bony structure of cancellous bone within the vertebral body. Furthermore, this delivery occurs through relatively little control of the flow of pressurized bone cement during delivery, much like as described above.

Another prior art system is described in U.S. Patent Application Publication No. 2005/0278023 to Zwirkoski. In this system, a plurality of segments, flexibly connected to one another, are inserted into a vertebral body to treat a compression fracture. The system includes an applicator having a rotary driver, such as an auger or a cog wheel, for transporting the plurality of flexibly connected segments through a cannula and into the vertebral body. Zwirkoski suggests passage of fluent materials such as bone cement into the vertebral body concurrent with the segments.

SUMMARY OF THE INVENTION

The present invention provides a system for forming an implant to stabilize a vertebral body. The system comprises a delivery cannula defining a delivery passage for providing access to the interior of the vertebral body. A plurality of solid beads, solid elements, are disposed adjacent to one another in the delivery passage of the delivery cannula. A void space is defined between the adjacent beads. The plurality of beads include a first bead adjacent to a second bead. A liquid, a fluent material, such as a cement, capable of setting to a hardened condition, is disposed within at least a portion of the void spaces between the beads in the delivery passage. A push rod is movably disposed within the delivery passage of the delivery cannula applies a force to the first bead and transfer the force through the first bead to the second bead to move the beads through the delivery passage and into the interior of the vertebral body. The beads simultaneously carry the fluent material therewith through the delivery passage and into the interior of the vertebral body upon application of the force to the first bead. The fluent material sets to the hardened condition to lock the beads to one another and form the implant.

The present invention further provides a method of delivering the plurality of beads and the fluent material into the vertebral body to form the implant using a system comprising the delivery cannula and the push rod. The method comprises the steps of disposing the beads in the delivery passage of the delivery cannula in a linear array to define the void space between the beads and disposing the fluent material within at least a portion of the void space in the delivery passage. The method further includes the steps of inserting the push rod in the delivery passage of the delivery cannula and moving the push rod along the delivery passage to apply the force to the first of the beads. The force is transferred through the first bead to the second bead disposed in the delivery passage to move the beads through the delivery passage and into the interior of the vertebral body. Additionally, the method includes the step of simultaneously carrying the fluent material with the beads as the beads move through the delivery passage and into the interior of the vertebral body upon application of the force. The fluent material then sets to the hardened condition to secure the beads and form the implant.

The present invention further provides a method of loading the plurality of beads and the fluent material into the delivery passage of the delivery cannula using a fill system having a container defining a loading chamber. A mover is provided for inserting into the loading chamber. The method comprises the steps of disposing the beads and the fluent material in the loading chamber of the container, inserting the mover in the loading chamber, and coupling the container to the delivery cannula. The beads and the cement are transferred from the loading chamber into the delivery passage of the delivery cannula such that the beads and fluent material are loaded into the delivery cannula with void spaces defined between adjacent beads and with the fluent material at least partially filling the void spaces in the delivery passage.

The invention further provides a method of loading the plurality of beads and the fluent material into the delivery passage of the delivery cannula using the fill system. The method comprises the steps of disposing the beads in the delivery cannula in a staggered arrangement. The container is coupled to the delivery cannula. The fluent material is then transferred from the loading chamber into the delivery passage of the delivery cannula such that the fluent material is loaded into the delivery cannula and at least partially fills the void spaces defined between the adjacent beads by moving through gaps defined between the beads and the delivery cannula.

The present invention also provides a method of loading the fluent material in void spaces defined between the plurality of beads in the delivery cannula while simultaneously delivering the beads and the fluent material to the interior of the vertebral body. The method comprises the steps of disposing the beads in the delivery passage defined by the delivery cannula in the linear array to define the void spaces between the beads in the delivery passage, inserting a push rod in the delivery passage of the delivery cannula, and moving the push rod along the delivery passage to apply the force to the beads. Application of force moves the beads through the delivery passage and into the interior of the vertebral body. The fluent material is introduced within at least a portion of the void spaces as the beads move through the delivery passage and before the beads exit the delivery cannula and enter the interior of the vertebral body.

By delivering the beads under the force of the push rod, the fluent material is transported by the beads and enters into the interior of the vertebral body under a low pressure. This low pressure delivery of the fluent material prevents extravasations which can result from delivering the fluent material under a high pressure. Additionally, amounts of the beads and the fluent material delivered can be highly controlled to ensure adequate stabilization of the bony structure of cancellous bone present within the vertebral body thereby preventing motion of the implant within the vertebral body. The system also provides the user with flexibility in that the beads and the fluent material can be loaded into the delivery cannula and delivered to the interior of the vertebral body using a variety of loading and delivery systems.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 2 is an exploded cross-sectional side view of the delivery cannula and beads surrounded by a fluent material;

FIG. 3 is a cross-sectional side view of the beads and the cement, the fluent material, loaded in the delivery cannula;

FIG. 9 is a cross-sectional end view of an alternative delivery cannula;

FIG. 10 is a cross-sectional end view of another alternative delivery cannula;

FIG. 11 is a cross-sectional side view of yet another alternative delivery cannulae;

FIGS. 12A-12I are cross-sectional perspective views of delivery cannulae illustrating alternative configurations for the beads;

FIGS. 24A and 24B are cross-sectional side views of a 2-stage system for filling the delivery cannula with beads and the cement;

FIG. 24C is a cross-sectional end view taken along line 24C-24C of FIG. 24A;

FIG. 25 is a cross-sectional side view of a parallel system for loading the fluent material to the beads as the beads are moved along the delivery passage of the delivery cannula;

FIGS. 26A-26C are cross-sectional top views of the vertebral body illustrating the delivery of the beads and the fluent material to the interior at different volumetric ratios;

FIGS. 27A-27E are cross-sectional side views of the access cannula and delivery cannula of the system exposing the push rod, beads, and fluent material and illustrating the delivery of different volumetric ratios of the beads to the fluent material based on a minimum dimension of the push rod;

FIG. 28A is a partial cross sectional view of a portion of the interior of the barrel of the delivery assembly of FIG. 28;

FIG. 29 is a cross sectional view of an assembly of this invention capable of both mixing the beads and cement to form the agglomeration and then delivering the agglomeration to the bone;

FIGS. 32A-32C are perspective and cross sectional views of a balloon of this invention constructed to contain to hold the agglomeration as well as a think coating of cement around the agglomeration;

FIG. 41 is a side view of an alternative bead of this invention;

FIG. 42 is a view looking into a delivery cannula wherein the bead of FIG. 41 is disposed;

FIG. 43 is a view of an alternative bead of this invention disposed in the delivery cannula that contains the bead and cement agglomeration;

FIG. 44 is a side view of the bead disposed in the cannula of FIG. 43;

FIG. 45 is partial cross sectional longitudinal view of an array of the beads of FIG. 43 disposed in the delivery cannula;

FIGS. 54A and 54B are longitudinal partial cross section views illustrating how sets of beads of the agglomeration of this invention are partially or fully contained in socks;

DETAILED DESCRIPTION

I. Overview

Figure 1:
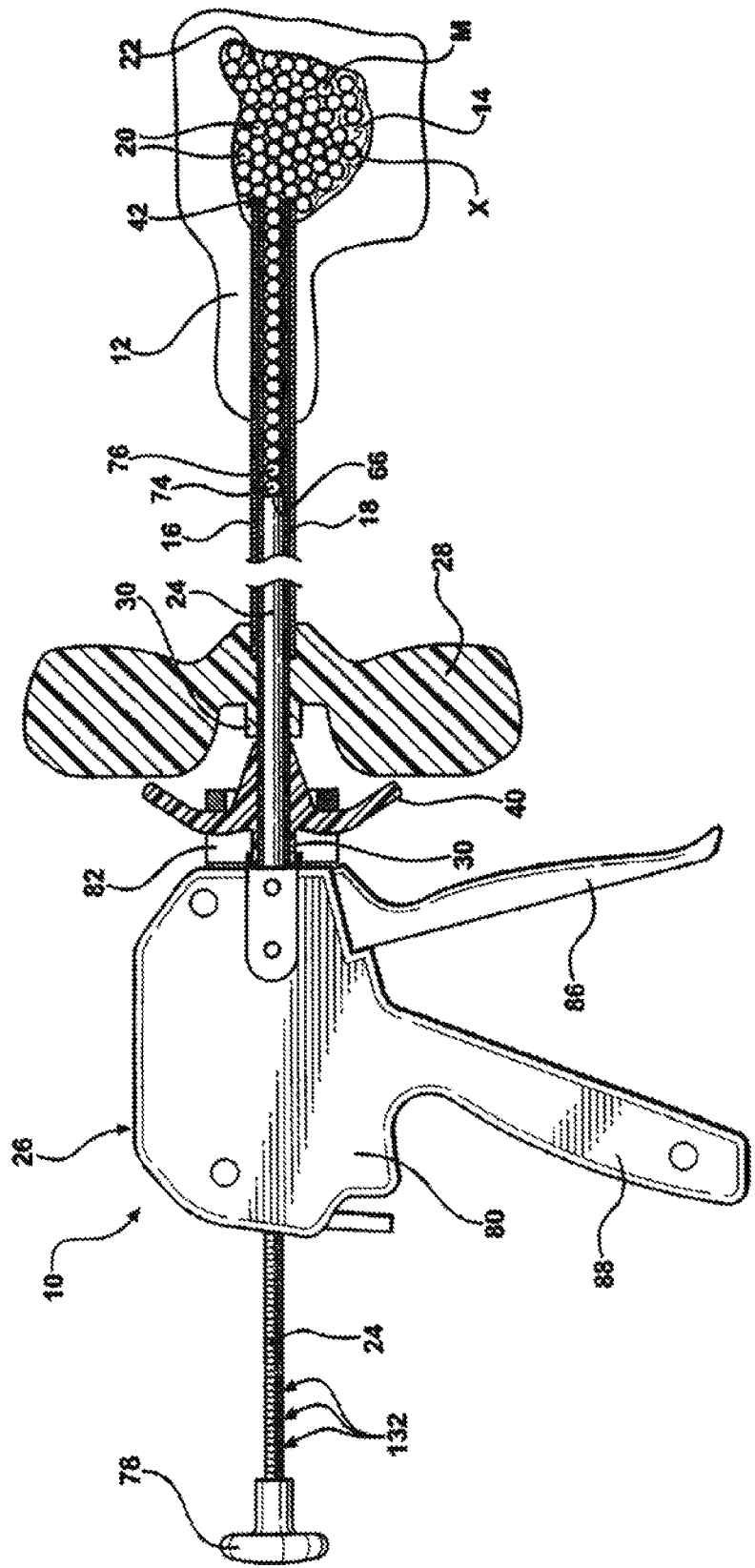
FIG. 1 is a partial cross-sectional side view of a system for performing vertebral augmentation with an access cannula and a delivery cannula inserted in an interior of a vertebral body.

Referring to the Figures, wherein like numerals indicate corresponding parts throughout the several views, a system for forming an implant M to stabilize a vertebral body 12 having an interior of cancellous bone 14 is shown generally at 10. The system 10 is used to treat vertebral compression fractures, for repair of intervertebral discs, as an interbody fusion device, as well as for treating other compression fractures including, but not limited to, tibia plateau fractures, Colles' fractures, crush fractures, or distal tibia fractures. For example, when the vertebral body 12 experiences a compression fracture, system 10 is used to form an implant M in the interior of cancellous bone 14 of the vertebral body 12 and stabilize the vertebral body 12. The system 10 may also be used for restoring an orbit floor or for elevating soft tissue in cosmetic applications. The system 10 may be used to distract tissue, fill a cavity in tissue (existing or created), reinforce tissue, compress tissue (e.g., cancellous bone), or create a cavity in tissue. Moreover, the system 10 will form the implant M at a low pressure to prevent extravasations of the implant M from the vertebral body 12 thereby preventing the implant M from entering any other part of the body, such as vascular tissue.

II. Access Cannula

Referring generally to FIGS. 1-6, the system 10 includes an access cannula 16, a delivery cannula 18, a plurality of beads 20, a cement 22, and a push rod 24. The access cannula 16 is for accessing the interior of the vertebral body 12. The delivery cannula 18 is sized for insertion in the access cannula 16. The beads 20 and the cement 22 are disposed within the delivery cannula 18 where the push rod 24 applies a force on the plurality of beads 20 in the delivery cannula 18 to deliver the beads 20 and the cement 22 from the delivery cannula 18 to the interior of the vertebral body 12. To facilitate delivery of the beads 20 and the cement 22, the system 10 may also include a delivery mechanism 26.

Figure 4:
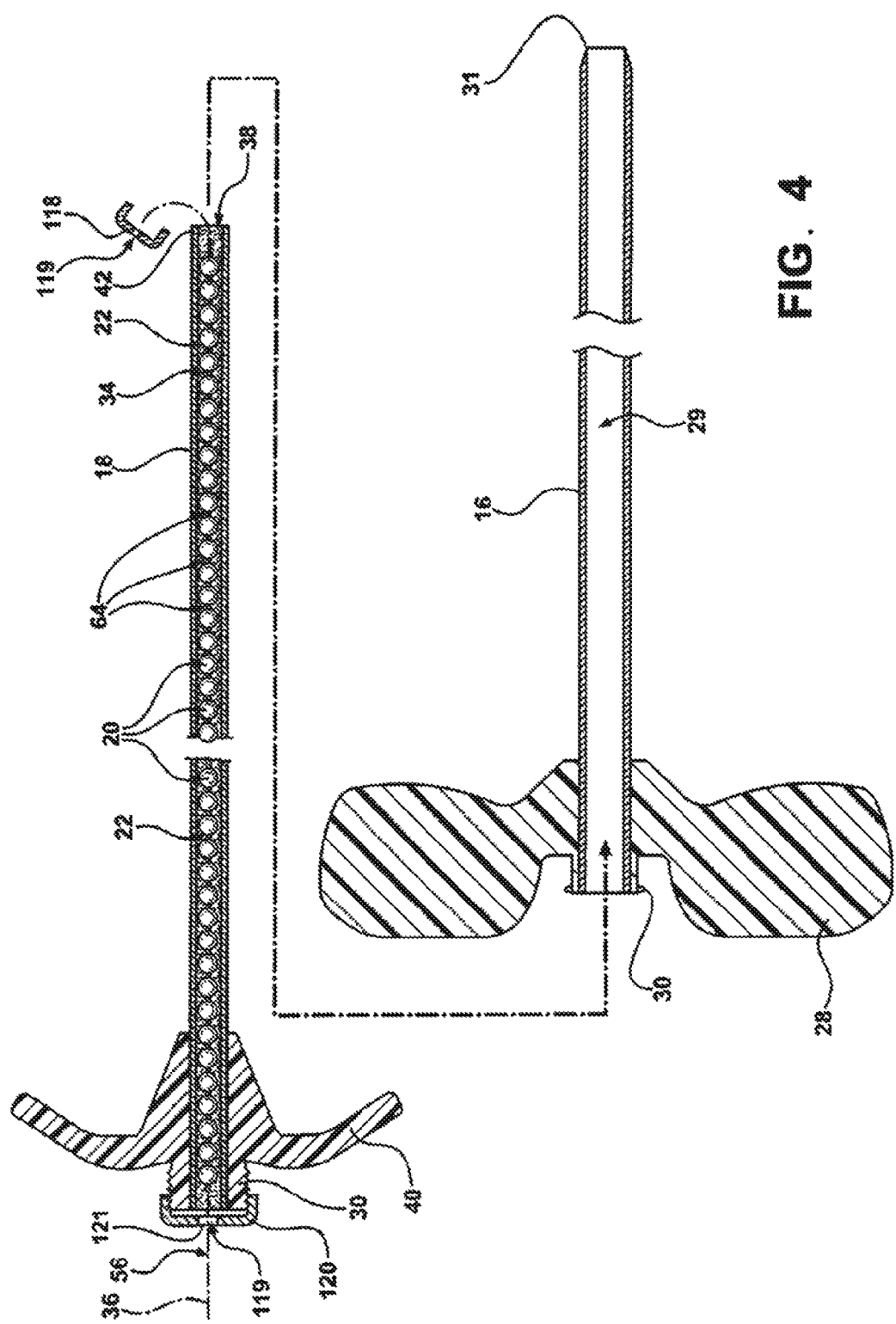
FIG. 4 is an exploded cross-sectional side view of the delivery cannula, beads, and cement of FIG. 3 and the access cannula.
Figure 5:
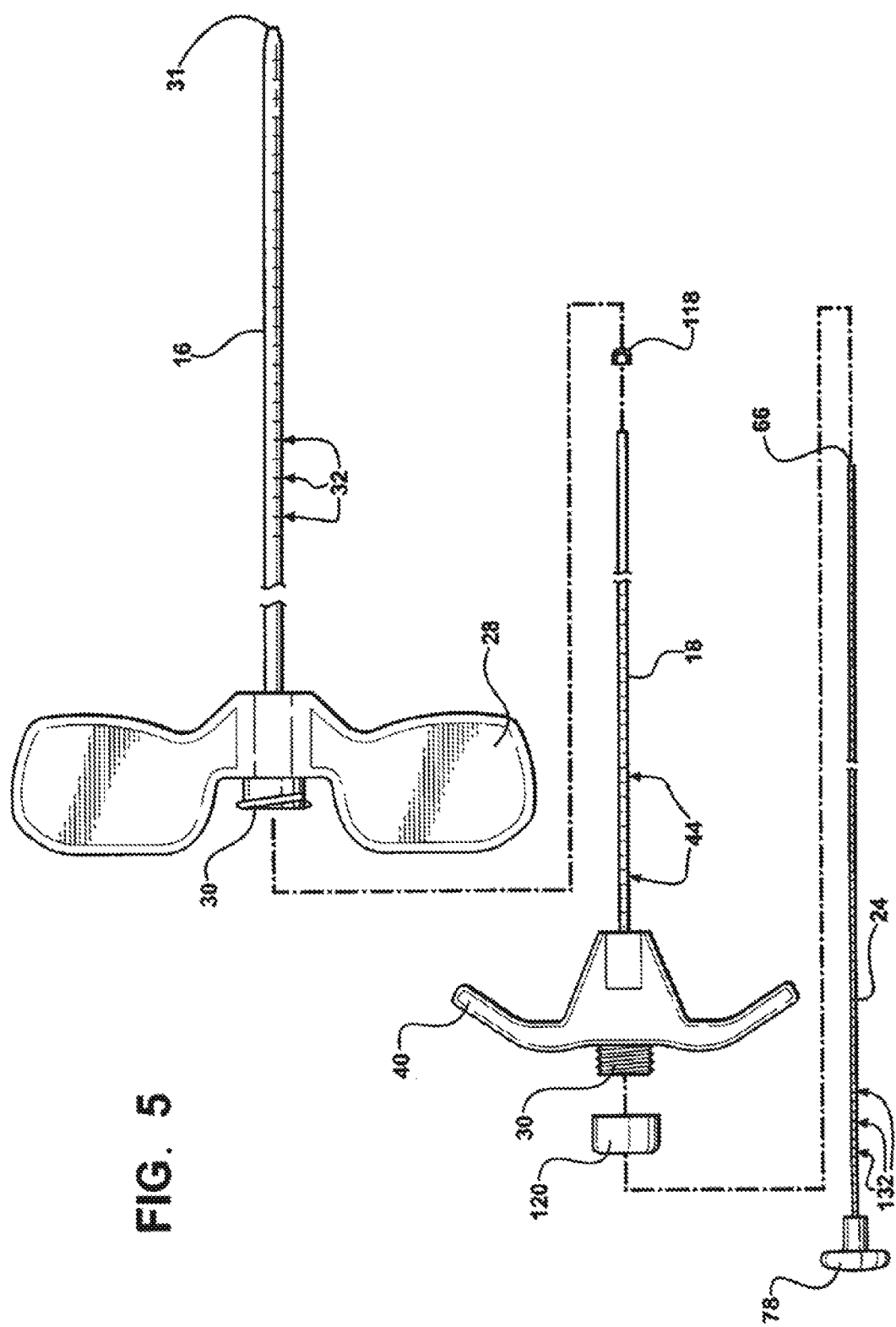
FIG. 5 is an exploded side view of the access cannula, the delivery cannula, and a push rod.
Figure 6:
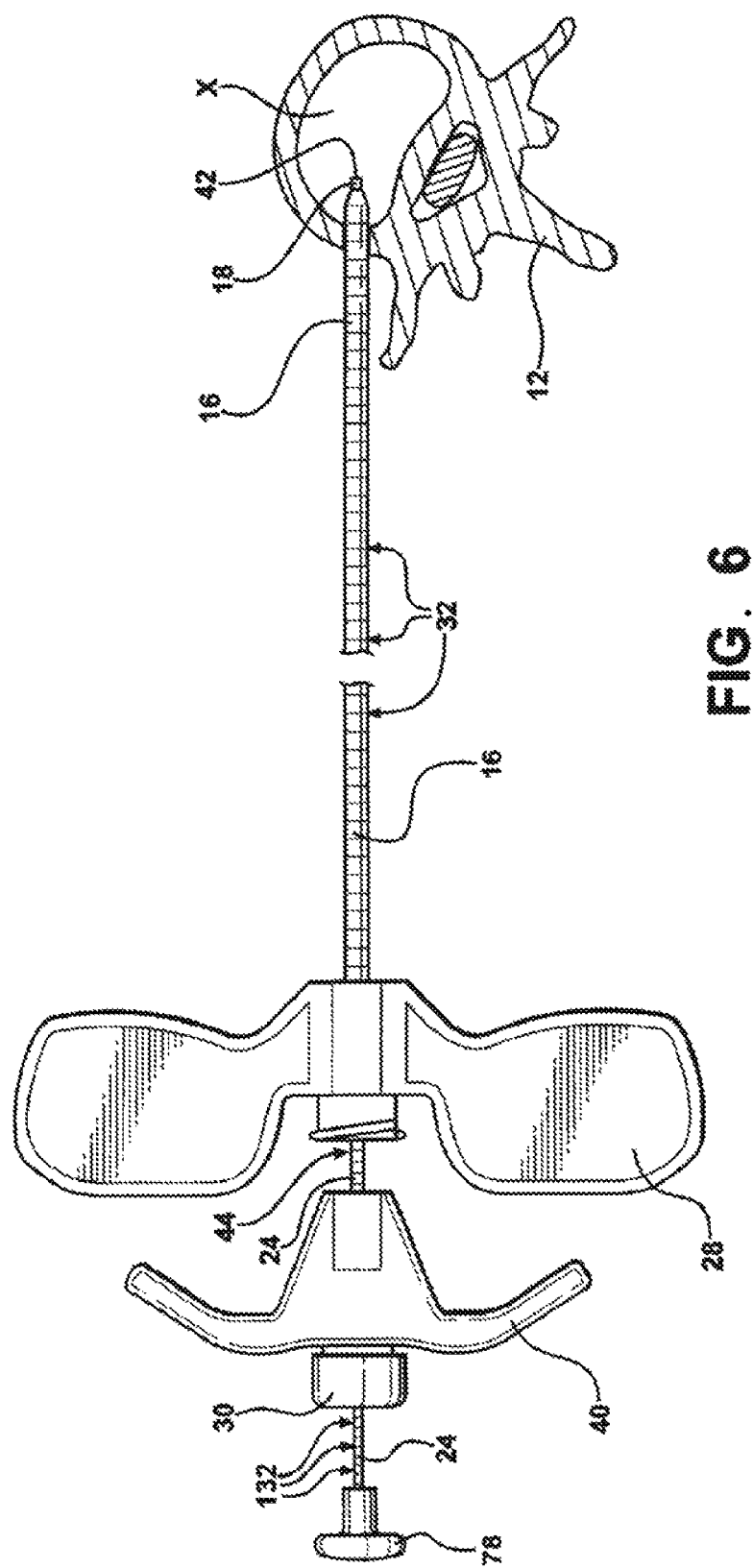
FIG. 6 is a top view of the system showing the access cannula inserted within the vertebral body and the delivery cannula partially inserted within the access cannula and the push rod inserted within the delivery cannula.

Referring specifically to FIGS. 4-6, the access cannula 16 defines an access passage 29 which is cylindrical for accessing the interior of the vertebral body 12. The delivery cannula 18 is sized for insertion in the access passage 29 of the access cannula 16. The access cannula 16 is preferably formed of a biocompatible material and may be fixed to an access handle 28. The biocompatible material used to form the access cannula 16 may be any biocompatible metal or other material. The access cannula 16 is configured to percutaneously enter a target site X without creating major trauma around the target site X. The access cannula 16 is further configured to accommodate any size, shape, or type of delivery cannula 18, described below. The access handle 28 preferably includes a luer-lock connector 30 for connecting to various instruments for drawing materials from the target site X, delivering materials into the target site X, and the like.

The access handle 28, access cannula 16, or portions of the access cannula 16 may be formed of a radiolucent material for use in a fluoroscopic field. Methods for inserting the access cannula 16 into the tissue to access a target site X are well known in the art and will not be described in detail. For instance, the access cannula 16 may be placed in the vertebral body 12 using a solid stylet (not shown) sized to match the access passage 29. The access cannula 16 may have a threaded distal end (not shown) to secure the access cannula 16 to the tissue, e.g., bone. The access cannula 16 may include markings 32 (see FIG. 5) to approximately determine the depth the access cannula 16 is inserted when inserting the access cannula 16 into the patient to access the target site X. It should be appreciated, however, that the access cannula 16 is not required as the delivery cannula 18 can be used to directly access the interior of the vertebral body 12.

Referring specifically to FIGS. 2-6, the delivery cannula 18 defines a delivery passage 34, extending along a delivery axis 36 (see FIG. 2), for providing access to the interior of the vertebral body 12. The delivery passage 34 further defines an exit port 38, open to the delivery passage 34, for allowing the beads 20 and the cement 22 to exit the delivery cannula 18 and enter the interior of the vertebral body 12, as illustrated in FIG. 1. The delivery passage 34 has an inner diameter ID for accommodating the push rod 24, which is movably disposed within the delivery passage 34 of the delivery cannula 18.

The delivery cannula 18 is preferably formed of a biocompatible material and is fixed to a delivery handle 40. The biocompatible material used to form the delivery cannula 18 may be any biocompatible metal or other material. The delivery cannula 18 is configured to accommodate any size or shape of the beads 20 being used. In the case of using spherical beads 20, the delivery cannula 18 is preferably in the shape of a cylindrical tube. Of course, any shape may be used for the delivery cannula 18. The delivery handle 40 preferably includes a luer-lock connector 30 for connecting to various instruments for filling the delivery cannula 18 with the cement 22, drawing the cement 22 from the delivery cannula 18 or target site X, delivering the cement 22 into the target site X, and the like.

The delivery handle 40, delivery cannula 18, or portions of the delivery cannula 18 may be formed of a radiolucent material for use in a fluoroscopic field. For instance, in one embodiment, a distal end 42 of the delivery cannula 18 may be radiopaque for determining a position of the distal end 42, while the remaining portion of the delivery cannula 18 is radiolucent to enable viewing of the beads 20 in the delivery cannula 18 during use. The delivery cannula 18 is configured, e.g., sized, for sliding within the access cannula 16. This allows the delivery cannula 18 to be inserted into the access cannula 16 to access the target site X. The delivery cannula 18 may also include markings 32 for determining the depth of insertion of the delivery cannula 18 in the access cannula 16.

Alternative delivery cannulae 18, defining angled delivery openings, are shown in FIGS. 7A-7F. The angled delivery openings facilitate radial and/or axial delivery of the beads 20 and the cement 22 to a target site X in the interior of the vertebral body 12. With these angled delivery openings, reaction forces between the delivery cannula 18 and the interior of the vertebral body 12 vary and may require less user applied axial force to position the delivery cannula 18 while ejecting the beads 20 from the delivery cannula 18 into the target site X. This allows the user to better control the location of the delivery cannula 18 while delivering the beads 20 from the delivery cannula 18. Thus, the delivery cannula 18 is less likely to be pushed back out of the target site X, which may happen when the delivery axis 36 extends axially along the central axis 50 of the delivery cannula 18. These delivery cannulae 18 can also be rotated during delivery of the beads 20 to steer or direct the delivery of the beads 20 and the cement 22 as desired by the user. When using these angled delivery openings, it is understood that the distal end 42 of the delivery cannula 18 will extend generally beyond a distal end 43 of the access cannula 16 inside the vertebral body 12.

In these embodiments, the exit port 38 opens at a delivery angle 46 of less than 180 degrees to the delivery axis 36 for allowing the beads 20 and the cement 22 to exit the delivery cannula 18 at the delivery angle 46 relative to the delivery passage 34. In one embodiment, the beads 20 and the cement 22 exits the exit port 38 of the delivery cannula 18 perpendicular to the delivery passage 34. In this embodiment, the delivery angle 46 is about 90 degrees to the delivery axis 36. In other embodiments, the delivery angle 46 may range from about 10 degrees to less than 90 degrees. More preferably, the delivery angle 46 ranges from about 25 degrees to about 65 degrees.

Figure 7A:
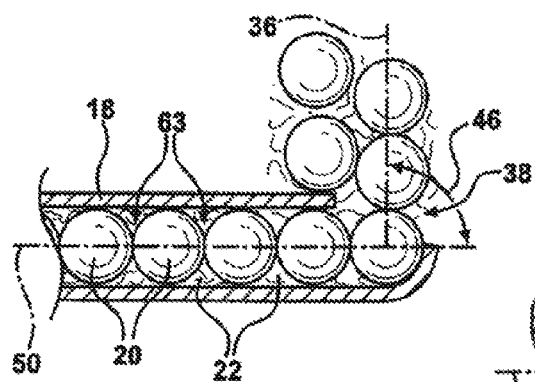
FIGS. 7A-7F are cross-sectional views of the alternative delivery cannulae.
Figure 7D:
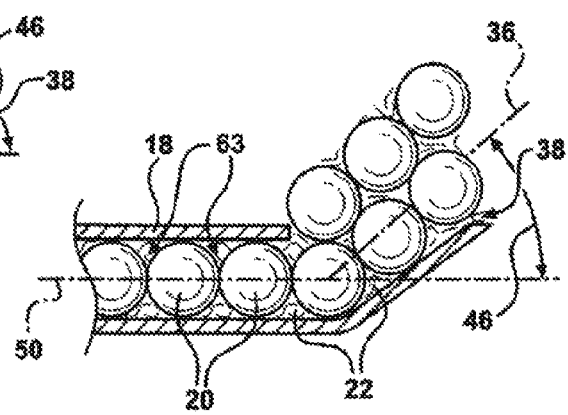
Figure 7B:
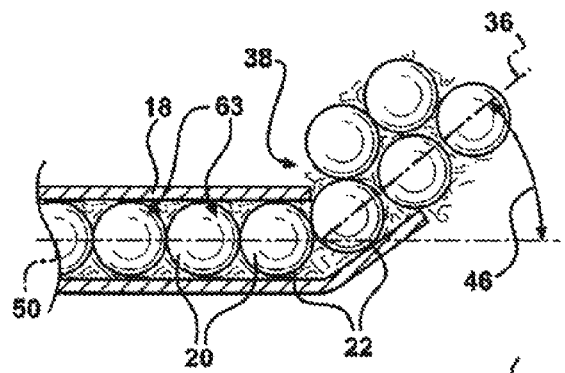
Figure 7E:
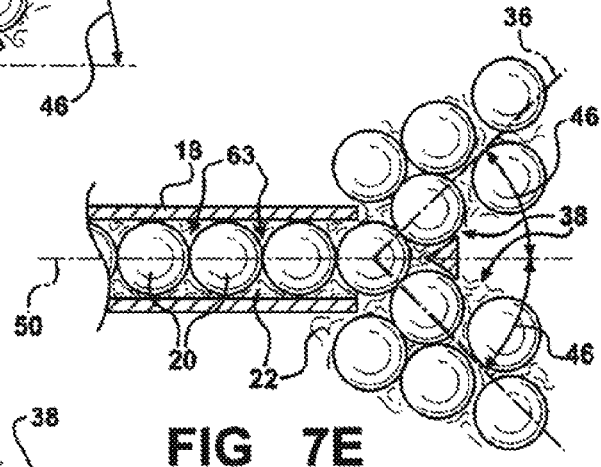
Figure 7C:
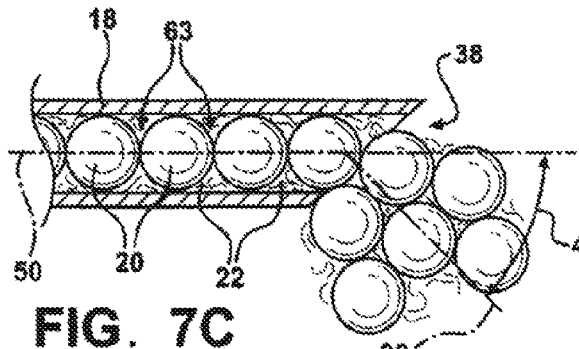
Figure 7F:
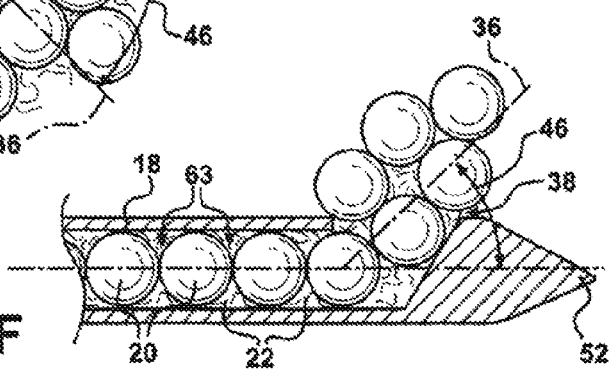

In FIG. 7A, the exit port 38 defines a notch 48 formed in a rounded distal end 42 of the delivery cannula 18 to facilitate delivery of the beads 20 to the target site X in a direction comprising radial and/or axial vectors. In FIG. 7B, one side of the distal end 42 of the delivery cannula 18 is angled inwardly relative to a central axis 50 of the delivery cannula 18 to deflect the beads 20 toward the target site X in a direction comprising radial and/or axial vectors. In FIG. 7C, the distal end 42 of the delivery cannula 18 is beveled such that the exit port 38 facilitates delivery of the beads 20 in a direction comprising radial and/or axial vectors. In FIG. 7D, the delivery cannula 18 has a sharpened, beveled, distal end 42 to penetrate into the tissue at the target site X with a radially oriented exit port 38. The interior surface of the delivery cannula 18 at the distal end 42 is oriented at an acute angle relative to the central axis 50 of the delivery cannula 18 to deflect the beads 20 out through the exit port 38 as they are forced down the delivery cannula 18 by the push rod 24. In this instance, the delivery cannula 18 may be inserted into the target site X with or without the use of the access cannula 16 to deliver the beads 20 into the target site X in a direction comprising radial and/or axial vectors. In FIG. 7E, two openings are provided to deflect the beads 20 in opposite directions to the target site X comprising radial and/or axial vectors.

Alternatively, the delivery cannula 18 may have a sharpened distal end 42 forming a tip 52 for penetrating the tissue at the target site X with a radially oriented exit port 38. As with the embodiment shown in FIG. 7F, the delivery cannula 18 may be inserted into the target site X with or without the use of the access cannula 16 to deliver the beads 20 into the target site X.

Referring to FIGS. 8A-8C, 9, and 10, further embodiments of the delivery cannula 18 are shown. In these embodiments, the delivery cannula 18 has internal guide ribs 61 for spacing the beads 20 from a delivery wall 62 of the delivery cannula 18. This allows the beads 20 to be held in a linear array, centered on the delivery axis 50. This allows the cement 22 to back flow around the beads 20 within the delivery passage 34. The delivery wall 62 surrounds the delivery passage 34 and defines at least one groove 65 open to the delivery passage 34 for holding the cement 22. In this embodiment, the grooves 65 are defined between the ribs 61 to allow the cement 22 to fill the void spaces 63 between the beads 20 for simultaneous delivery to the target site X. The ribs 61 may be any shape or size with multiple variations to control the alignment of the beads 20 and a volume of cement 22 available for delivery to the target site X. The ribs 61 are either part of the delivery wall 62 and define the grooves 65 therebetween, as shown in FIGS. 8A-8C and 9 or the ribs 61 may be a deformed part of the delivery wall 62, as shown in FIG. 10.

FIG. 11 illustrates another alternative delivery cannula 18 of the system 10. The delivery cannula 18 of this alternative embodiment includes an outer sleeve 54 and inner sleeve 56 with an annular space 58 defined therebetween. The beads 20 are loaded into a central lumen 60 defined within the inner sleeve 56, while the cement 22 is loaded into the annular space 58 defined between the outer and inner sleeves 54, 56. The inner sleeve 56 is perforated or slotted to allow the cement 22 to fill the void spaces 63 between the beads 20 for simultaneous delivery.

IV. Beads

Beads 20 are formed from solid material. In some versions of the invention beads 20 have a generally spherical shape. However, as described below, the beads 20 may have alternative shapes. The beads 20 are disposed adjacent to one another in cannula delivery passage 34 in a linear array and include at least three beads 20 and at least two void spaces 63 defined between adjacent beads 20 (see FIG. 3). The beads 20 may have an outer diameter OD (see FIG. 8C) substantially equal to the inner diameter ID of the delivery passage 34. However, it should be appreciated that the outer diameter OD of the beads 20 is not limited to being substantially equal to the inner diameter ID of the delivery passage 34 as any outer diameter of the beads 20 may be used to obtain the performance desired by the implant M. The beads 20 may be interconnected by a connecting member 64, which may be flexible. If the beads 20 are interconnected, the connecting member 64 may require severing if the desired volume of the beads 20 and the cement 22 has been attained within the interior of the vertebral body 12. To accomplish the severing, the distal end 43 of the access cannula 16 includes a cutter 61 for cutting the connecting member 64 as the access cannula 16 is moved relative to the delivery cannula 18. This means that the access cannula 16 is moved deeper within the interior of the vertebral body 12 to sever the connecting member 64.

Figure 14:
FIG. 14 is yet another alternative shape for the beads illustrating a sphere defining holes for receiving the cement.
Figure 13:
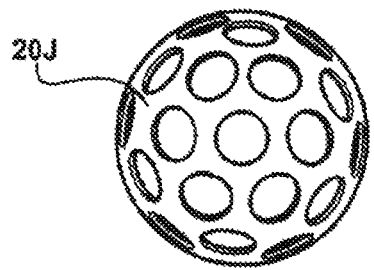
FIG. 13 is an alternative shape for the bead illustrating a whiffle-ball shape defining holes for receiving the cement.

The beads 20 used with the system 10 may be rigid, semi-rigid, or deformable. The beads 20 can be formed into any shape (pellets, beads, oval-shaped, cylinder-shaped, faceted elements, box-shaped, dumb-bell shaped, nestled shapes, which disconnect upon entering the target site X, coils, etc.). In addition to the spherical beads 20, FIGS. 12A-12I, 13, and 14 illustrate various beads 20 for use with the system 10 of the present invention to form the implant M. Other shapes may include rice shaped beads 20A (FIG. 12A), cylindrically-shaped beads 20B (FIG. 12B), box-shaped beads 20C (FIG. 12C), dumb-bell shaped beads 20D (FIG. 12D), interlocking beads 20E (FIG. 12E), springs 20F (FIG. 12F), interconnected spherical beads 20G (FIG. 12G), cross-shaped beads 20H (FIG. 12H), indented spherical beads 20I (FIG. 12I), whiffle-ball shaped beads 20J (FIG. 13), or semi-hollow spherical beads 20K (FIG. 14).

The number of the beads 20 needed to form the implant M varies depending on the procedure and the patient. Any combination of bead 20 sizes and shapes may be used in the implant M to vary packing characteristics of the beads 20 in the target site X. The beads 20 may also be selected to optimize packing to secure the implant M in the target site X. The size of the beads 20 may be selected to optimize delivery to the target site X and use of the system 10. The beads 20 may also be customized for anatomical considerations, i.e., smaller than cancellous bone 14 pores to build on existing strength in the bone, larger than the cancellous bone 14 pores to displace or compress the bone, sized to plug typical fractures, sized to prevent leaking into vascular tissue, and the like.

The beads 20 may be formed of metals, alloys, ceramics, polymers, bone derived material, or combinations of these materials. Metals that may be used in the beads 20 include, but are not limited to, biocompatible metals and alloys, ferrous or non-ferrous metals, such as stainless steels, gold, silver, tantalum, titanium, platinum, and other alloys, combinations, or equivalents thereof. Polymers that may be used in the beads 20 include, but are not limited to, elastomers, polymethyl methacrylate (PMMA), polyetheretherketone (PEEK), polymethymethacrylate (PMMA), polyvinylchloride (PVC), polyethylene (HDPE, UHMWPE, etc.), polystyrene (PS), polyesters (PET), polyamides (Nylons, aromatic polyamides), polypropylene, fluorocarbon polymers (PTFE, PTFCE, PVF, FEP), and other biocompatible materials.

The beads 20 may be formed of bioabsorbable or non-bioabsorbable material. The beads 20 may also include radiopaque materials to enhance visualization. The beads 20 may also be coated with radiopaque materials. Alternatively, the beads 20 may be formed of radiolucent materials or a combination of radiopaque and radiolucent materials. Additionally, the beads 20 may be coated to provide therapeutic properties. Coatings may include a therapeutic or medicinal material, such as an antibiotic, anticoagulants, biologic agents, radioactive agents (local cancer treatment), bone-growth promoting agents, or combinations thereof. In embodiments employing the connecting member 64, the connecting member 64 may be a wire, string, fiber, or other suitable connector. In other embodiments, loose beads 20 are used, with the beads 20 only being connected together by the cement 22 mixed with the beads 20.

V. Cement

The cement 22 is preferably capable of setting to a hardened condition and is disposed within at least a portion of the void spaces 63 defined between adjacent beads 20 in the delivery passage 34. The cement 22 may be a slurry, liquid, paste, or gel that may solidify during or after delivery. In one embodiment, the cement 22 is bone cement, e.g., PMMA bone cement, synthetic bone graft cements, or combinations or substitutions thereof, that solidifies after delivery. The cement 22 may also include therapeutic materials, e.g., bone morphogenic proteins, cells or gene therapies, bone growth factors, radioactive agents for local cancer treatment, or combinations or substitutions thereof. In addition, the cement 22 may have an affinity to attach to the beads 20, which helps keep the beads 20 associated with one another throughout delivery to form the implant M. The beads 20 may be hollow and/or have perforations and/or passages for the cement 22 (see e.g., FIGS. 13 and 14). The beads 20 may have modified surface characteristics, e.g., porous, to better adhere the cement 22 to the beads 20 during delivery, to facilitate tissue in-growth, or to reduce overall element 20 weight.

VI. Push Rod

Figure 15:
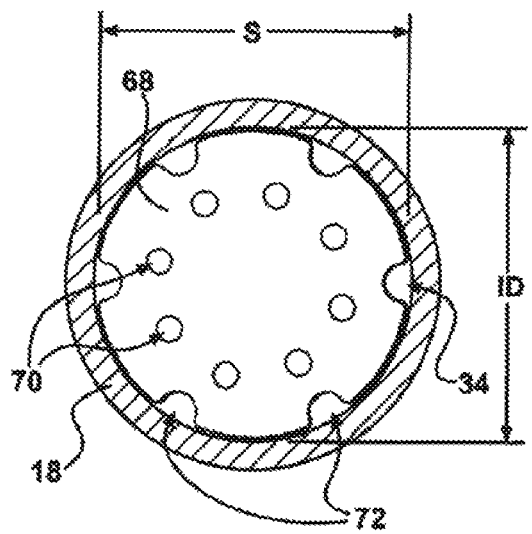
FIG. 15 is a cross-sectional end view of the head end of the push rod disposed inside of the delivery cannula.
Figure 16:
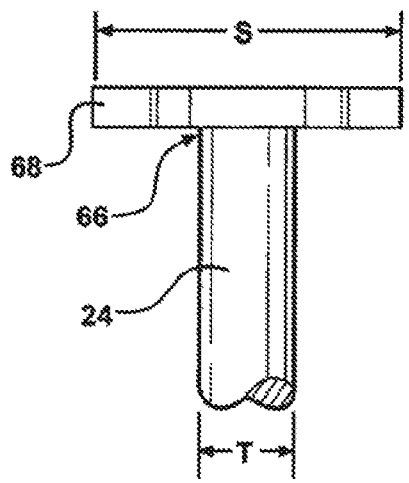
FIG. 16 is a side view of the push rod having the head attached.

Referring to FIGS. 5, 15, and 16, the push rod 24 extends to a distal end 66 and has a minimum dimension T. The push rod 24 is shaped and sized for insertion into the delivery cannula 18. In one embodiment, the push rod 24 is a solid metal rod wherein the minimum dimension T corresponds to a diameter that is slightly smaller than the inner diameter ID of the delivery cannula 18 to provide relatively small tolerances between the push rod 24 and the delivery cannula 18. In other embodiments, the push rod 24 and the delivery cannula 18 may define an annular space 58 therebetween for allowing the cement 22 to back flow through the annular space 58 as the push rod 24 is moved along the delivery passage 34 of the delivery cannula 18. In this embodiment, the minimum dimension T of the push rod 24, e.g., outer diameter, is less than the inner diameter ID of the delivery cannula 18. As the push rod 24 is moved along the delivery passage 34, this allows the cement 22 to backflow around of the beads 20 and into the delivery cannula 18. This further reduces the pressure of the cement 22 within the delivery cannula 18. A head 78 (see FIG. 1) can be fixed to the push rod 24 to facilitate gripping and placement of the push rod 24 into the delivery cannula 18.

Referring specifically to FIGS. 15 and 16, the push rod 24 may include a head 68 fixed to the distal end 66. Head 68 has a maximum dimension S for applying the force to the first element 74. The maximum dimension S of the head 68 is substantially equal to the inner diameter ID of the delivery passage 34. The head 68 and the delivery cannula 18 may define at least one gap 72 therebetween for allowing the cement 22 to backflow through the gap 72 as the head 68 is moved along the delivery passage 34 of the delivery cannula 18. The head 68 may also define a hole 70 for allowing the cement 22 to back flow through the hole 70 as the head 68 is moved along the delivery passage 34 of the delivery cannula 18. However, it should be appreciated that the invention is not limited to using a head 68 as the push rod 24 may be used without the head 68.

When the push rod 24 moves along the delivery passage 34, the push rod 24 applies a force to a first element 74, disposed adjacent the push rod 24, and transfers the force through the first element 74 to a second element 76, disposed adjacent the first element 74, and so on down the linear array of beads 20 to move the beads 20 through the delivery passage 34 and into the interior of the vertebral body 12. The beads 20 simultaneously carry the cement 22 therewith through the delivery passage 34 and into the interior of the vertebral body 12 upon application of the force to the first element 74. As a result, the beads 20 may compress the cancellous bone 14 within the vertebral body 12 and create interstitial gaps between the beads 20 inside the vertebral body 12. New interstitial gaps can be created between the beads 20 inside the vertebral body 12. These interstitial gaps in the vertebral body 12 correspond somewhat in volume to the previous void spaces 63 present between the beads 20 in the delivery cannula 18. Alternatively, the vertebral body 12 already defines the pre-existing cavity and the cancellous bone does not require compressing. The cement 22 is transported by the beads 20 into these interstitial gaps and sets to the hardened condition to lock the beads 20 to one another and form the implant M. As a result, the cement 22 is delivered to the interior of the vertebral body 12 at a low pressure which prevents extravasations of the cement 22 from the vertebral body 12.

Figure 17:
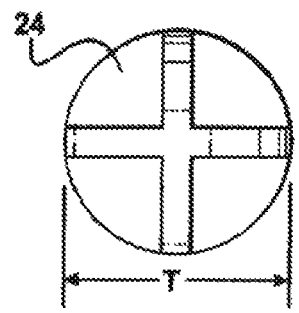
FIG. 17 is a end view of an alternative push rod having a cross shape.
Figure 18:
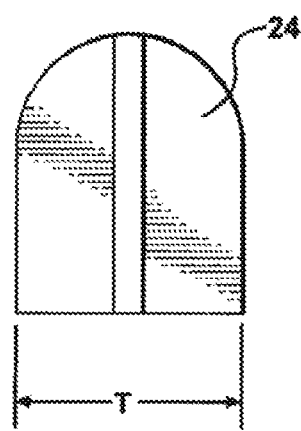
FIG. 18 is a side view of an alternative push rod having a spherical distal end.
Figure 19:
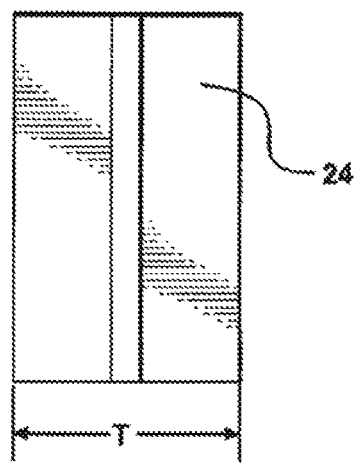
FIG. 19 is a another side view of the alternative push rod having a square distal end.

In other embodiments, shown in FIGS. 17-19, the push rod 24 may have alternative cross-sections, e.g., ribs, or a cross shape, to provide rigidity or stiffness and a tight clearance with the delivery cannula 18, while allowing the backflow of the cement 22, e.g., between the ribs and/or allowing the ribs to lie in the grooves 65 in the delivery cannula 18. The distal end 66 of the push rod 24 may be flat, as shown in FIG. 19, spherical, as shown in FIG. 18, or any other shape that is capable of providing the force necessary to deliver the beads 20 from the delivery cannula 18 into the target site X. This push rod 24 has a cross-section which is shaped to work with the delivery cannula 18 shown in FIGS. 8A-8C or FIG. 10. A shaped push rod 24 can be formed to fit inside of these delivery cannulae 18 with portions of the push rod 24 extending radially beyond the guide ribs 61 and into the grooves 65. As is discussed below, this alternate push rod 24 can be used to dispense the implant materials (e.g. beads 20 and cement 22) within the guide ribs 61 as well as some or all of the cement 22 contained in the grooves 65 of these delivery cannulae 18. This shape of the push rod 24 can provide a way to vary the ratio of the volume of the cement 22 relative to the volume of the elements 33 delivered from the delivery cannula 18.

VII. Delivery Mechanism

As an alternative to manually pushing the push rod 24, system 10 may include the delivery mechanism 26 with a force applying mechanism 84. Force applying mechanism 84 may be any mechanism known to those skilled in the art. Suitable mechanisms are shown in U.S. Pat. No. 5,431,654 to Nic and U.S. Patent Application Publication No. 2005/0128867 to Henniges et al., both of which are hereby incorporated by reference. Otherwise, a manual force, e.g., a hand and/or fingers or surgical hammer, is used to press the push rod 24 into the delivery cannula 18, as shown in FIG. 6, to deliver the beads 20 and cement 22 from the delivery cannula 18 to the target site X.

Figure 20:
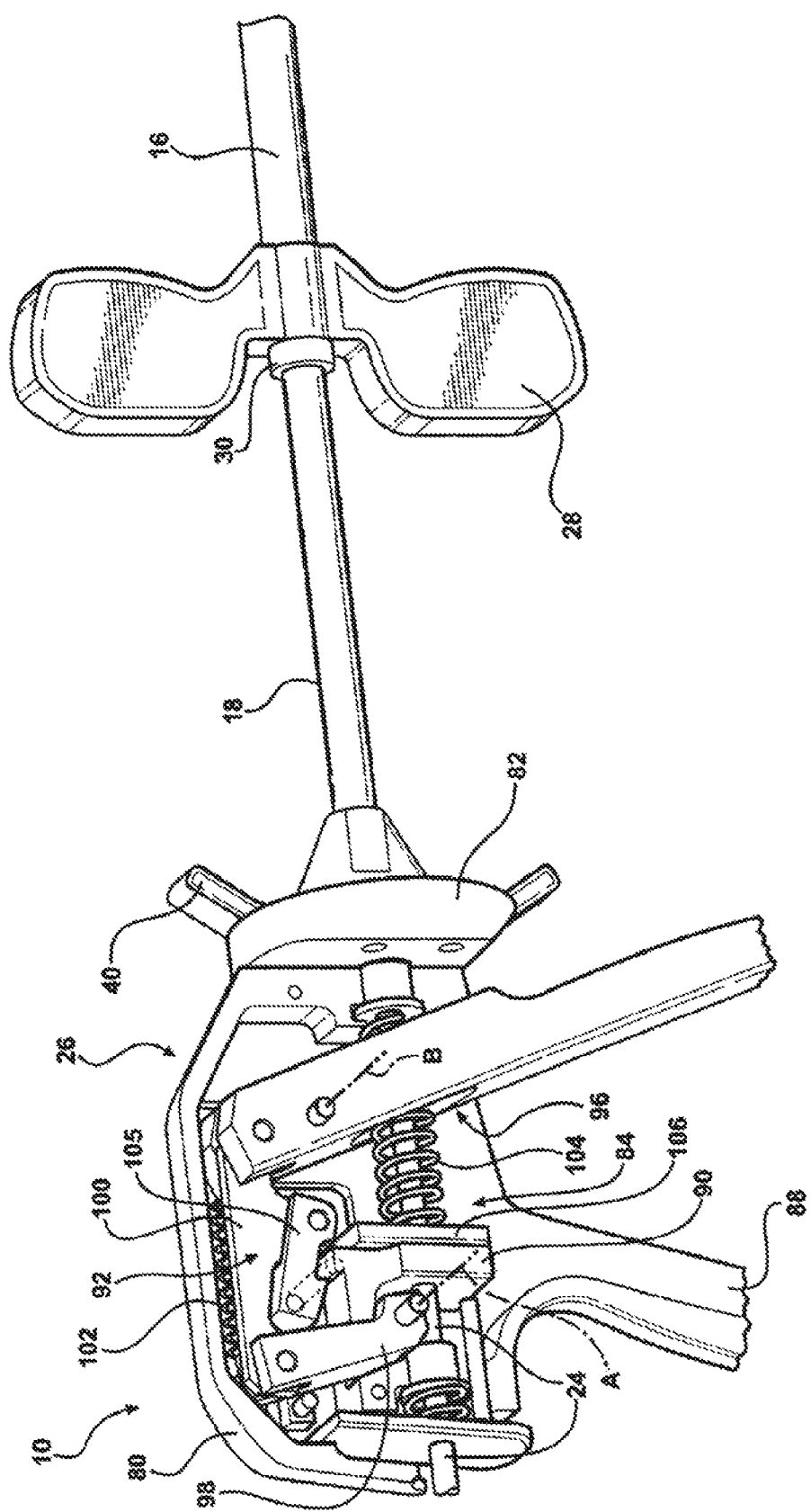
FIG. 20 is a perspective side view of a delivery mechanism having the push rod installed for driving into an attached delivery cannula.

One embodiment of the delivery mechanism 26 is shown in FIG. 20. The delivery mechanism 26 generally includes a housing 80, a connector 82, the force applying mechanism 84, and a trigger 86. A handle 88 is integrally formed with the housing 80 to maneuver the delivery mechanism 26 during use. The connector 82 extends from the housing 80 for engaging the delivery cannula 18.

The force applying mechanism 84 is supported by the housing 80 for applying a force to the push rod 24. The force applying mechanism 84 includes a gripper plate 90 responsive to movement of a linkage system 92 upon actuation of the trigger 86. The gripper plate 90 defines an aperture 96 surrounding the push rod 24. The gripper plate 90 frictionally engages the push rod 24 to advance the push rod 24 along the delivery cannula 18. The gripper plate 90 is urged forward while remaining in frictional contact with the push rod 24 by the linkage system 92 when the trigger 86 is actuated. The gripper plate 90 thereby advances the push rod 24 relative to the housing 80 and the delivery cannula 18 to drive the push rod 24 and force the beads 20 and the associated cement 22 from the delivery cannula 18. The trigger 86 is pivotally supported by the housing 80 and operatively connected to the force applying mechanism 84 to advance the force applying mechanism 84 upon actuation of the trigger 86.

The linkage system 92 includes a first link 98, which is pivotally mounted to the housing 80 about a pivot axis A adjacent to the gripper plate 90. The first link 98 is adapted to engage the gripper plate 90 when the first link 98 pivots about the pivot axis A. A second link 100 pivotally interconnects the trigger 86 to the first link 98 via support pins. The links and the trigger 86 are interconnected to move in unison upon rotation of the trigger 86 about a second pivot axis B. When the trigger 86 is pulled, the second link 100 rotates the first link 98 about the pivot axis A, which engages the gripper plate 90 and urges the gripper plate 90 forward while the gripper plate 90 remains in frictional engagement with the push rod 24 thereby advancing the push rod 24. A return spring 102 returns the links and the trigger 86 to an initial position upon release of the trigger 86. At the same time, a first spring 104 momentarily disengages the gripper plate 90 from the push rod 24 to slide the gripper plate 90 back to an initial position to await the next pull of the trigger 86. The housing 80 pivotally supports the first link 98 and the trigger 86 about the pivot axes A and B via support pins.

A release pin 105 disengages the gripper plate 90 to allow a user to freely move the push rod 24 by hand. The release pin 105 is connected to a retainer plate 106 and is adapted to engage the gripper plate 90. When the retainer plate 106 is pushed by the user, the release pin 105 engages the gripper plate 90 which forces the gripper plate 90 to tilt back against the bias of the first spring 104 thus releasing the push rod 24. As should be appreciated, pushing the retainer plate 106 also pivots the retainer plate 106, releasing its engagement with the push rod 24. With both the retainer plate 106 and the gripper plate 90 released, the push rod 24 is free to move. This allows the user to manually move the push rod 24 with respect to the housing 80.

The delivery mechanism 26 is adapted to engage the push rod 24 and the delivery cannula 18 and provides the force of the push rod 24 while holding the delivery cannula 18 to allow relative movement between the push rod 24 and the delivery cannula 18. This means that the delivery cannula 18 is mounted to the delivery mechanism 26, by the connector 82, and the push rod 24 is coupled with the force applying mechanism 84. This relative movement between the push rod 24 and the delivery cannula 18 moves the beads 20 and the cement 22 along the delivery passage 34 and into the interior of the vertebral body 12.

Figure 21:
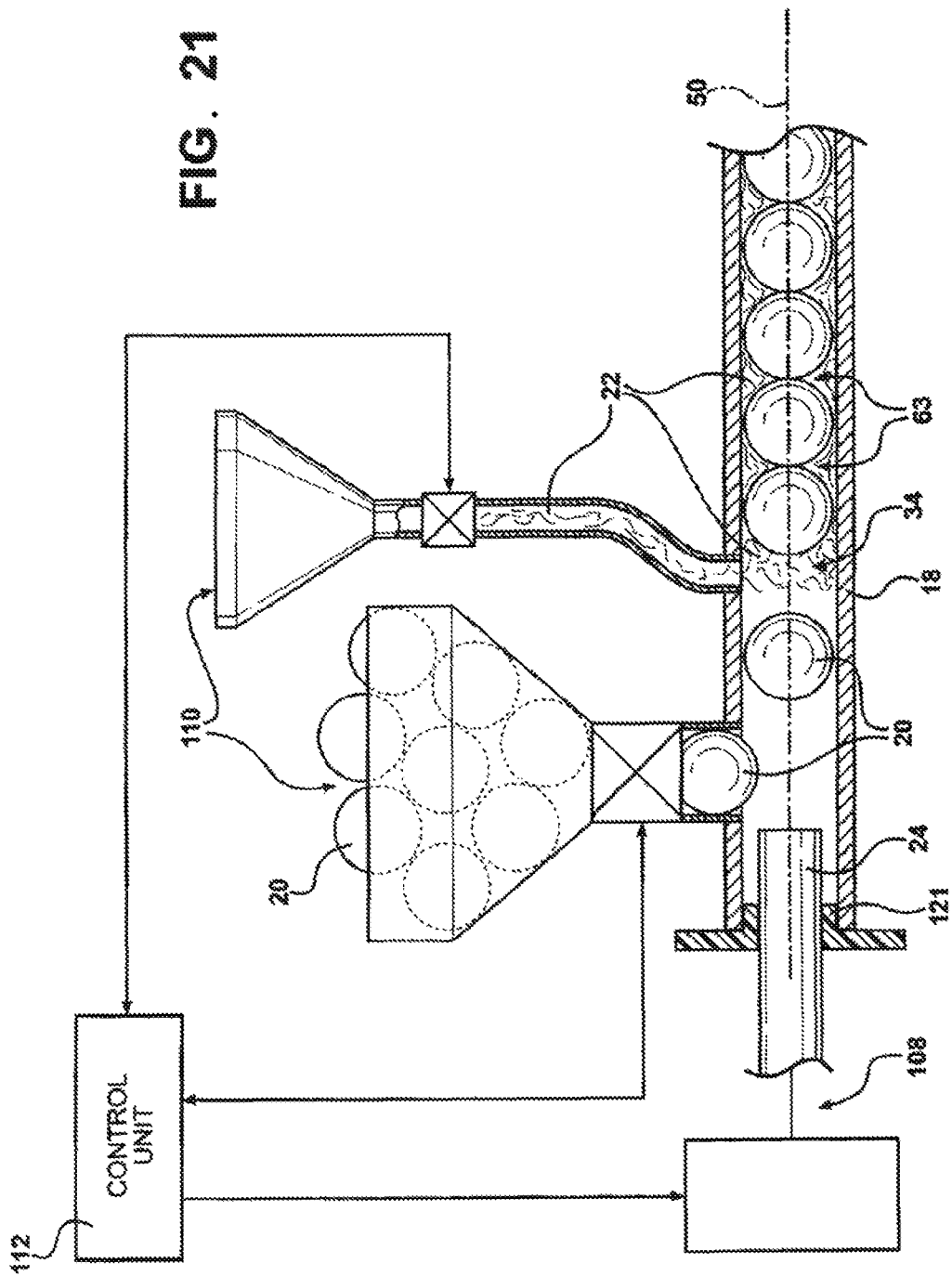
FIG. 21 is a another embodiment for filling the delivery passage of the delivery cannula with the beads and the cement.

Referring to FIG. 21, in an alternative system 10 of the present invention, the force used to deliver the beads 20 and the cement 22 can be replaced by an automatic system comprising a reciprocating driver 108 with the push rod 24 used with a modified delivery cannula 18. In this embodiment, the beads 20 and the cement 22 are stored within hoppers 110 or other suitable containers 124 for feeding to metering units that can be set by a controller 112 to adjust the relative amounts of the beads 20 and the cement 22 dispensed from the hoppers 110 into the delivery cannula 18 for delivery to the target site X. The reciprocating driver 108 is controlled by the controller 112, as set by the user, to customize delivery of the beads 20 and the cement 22 to the target site X to form the final implant M. This system 10 may be set to deliver a fixed or variable volume of the cement 22 based on a fixed or variable volume of the beads 20 dispensed into the delivery cannula 18.

VIII. Kits

Figure 22:
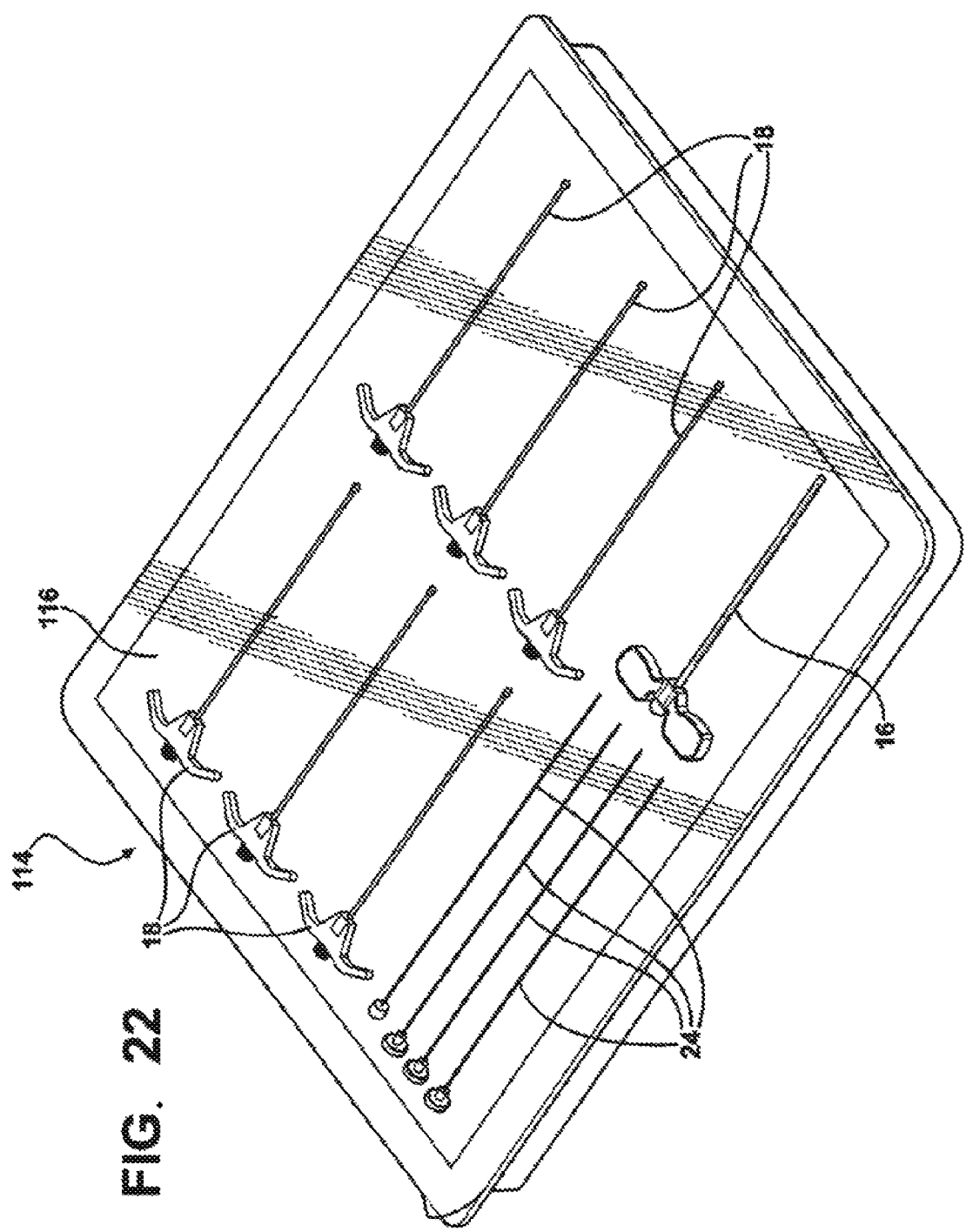
FIG. 22 is a kit for the system.
Figure 23:
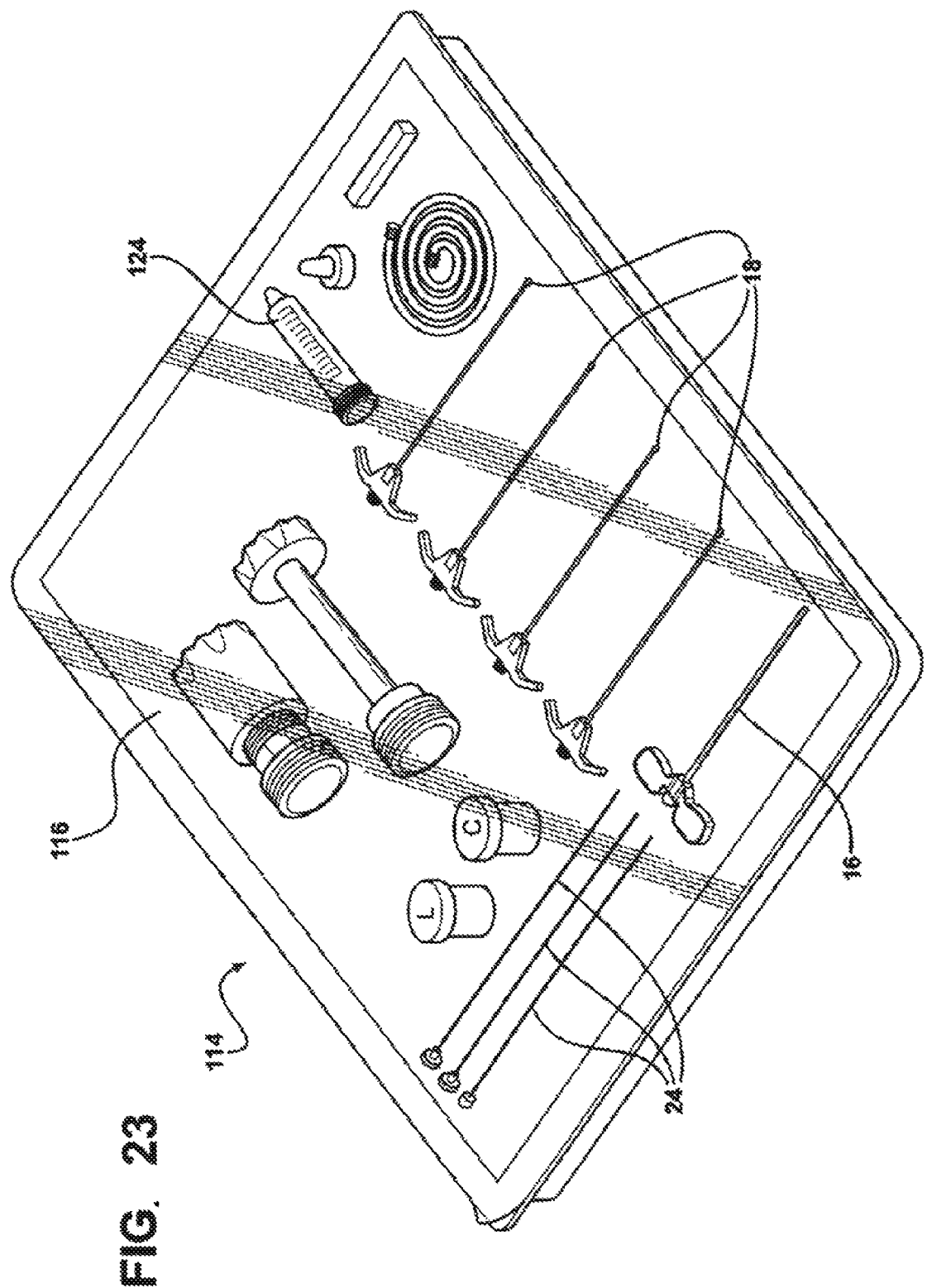
FIG. 23 is an alternative kit for the system.

Referring to FIGS. 22 and 23, various kits 114 may be provided with selected components of the system 10. In one exemplary kit, a sealed tray 116 or other type of package may include the access cannula 16, delivery cannula 18, and push rod 24, with the delivery cannula 18 being pre-loaded with the beads 20 and sealed with end caps 118, 120. Optionally, the delivery cannula 18 is pre-loaded with the cement 22, when the cement 22 is of a type that does not set in storage. A stylet (not shown) or other suitable device, used with or without a guide wire, may also be provided in the kit 114 for introducing the access cannula 16 into the target site X. As shown in FIG. 23, a bone cement delivery device may also be provided in the kit 114 for filling the delivery cannula 18 with the cement 22 in the void spaces 63 between the beads 20, such as a PCD® Precision System available from Stryker Corporation of Kalamazoo, Mich. The kit 114 may further include a liquid monomer L and powdered copolymer C for mixing together to form the cement 22 to be loaded into the delivery cannula 18 prior to use. Each of the kits 114 may be sterilized using techniques known to those skilled in the art. The delivery mechanism 26 may or may not be provided with this kit 114 depending on the particular needs of the user.

IX. System Operation

A. Loading the Delivery Cannula

To form an implant M using system 10 the delivery cannula 18 is loaded with an agglomeration, a mixture comprising the beads 20 and the cement 22 in an uncured state. The delivery cannula 18 may be preloaded with the beads 20 during shipping to facilitate use. In this instance, the distal end cap 118 is fitted onto the distal end 42 of the delivery cannula 18 and the proximal end cap 120 is luer-locked onto the luer-lock connector 30 mounted on the delivery handle 40. These end caps 118, 120 or other containment members can be used to hold the beads 20 in the delivery cannula 18 between a proximal end and the distal end 42. The end caps 118, 120 may have vents 119 to allow air to pass while filling the cement 22 into the delivery cannula 18. The proximal end cap 120 may include a seal 121, e.g., wiper, which allows insertion of the push rod 24 into the proximal end cap 120, while securing the beads 20 in the delivery cannula 18. The seal 121 may also retain the cement 22 within the delivery cannula if a viscosity of the cement 22 is low and/or to manage the pressure of the cement 22. The distal end cap 118 is removed prior to delivery of the beads 20 and cement 22 to the target site X.

Loading the beads 20 and the cement 22 can be facilitated by the geometry or configuration of the delivery passage 34 of the delivery cannula 18. As discussed above, the delivery passage 34 of the delivery cannula 18 may define grooves 65 and have ribs 61 for allowing the cement 22 to flow around the beads 20. This can provide better coverage of the beads 20 and/or improve the filling of the delivery cannula 18 with the cement 22.

Referring to FIGS. 24A and 24C, loading the beads 20 and the cement 22 can also be facilitated by placing the beads 20 in a staggered configuration in the delivery passage 34 such that gaps G are defined between the beads 20 and the delivery cannula 18, as shown in FIG. 24C. A 2-stage fill system 122 may be used to fill the delivery cannula 18 with the fluent material. The fill system 122 includes a container 124, defining a loading chamber 126, and a mover 128 for inserting into the loading chamber 126. In one embodiment, the fill system is a conventional syringe with plunger. The cement 22 is disposed in the loading chamber 126 of the container 124. The mover 128 is then inserted in the loading chamber 126 and the container 124 is coupled to the delivery cannula 18. The mover 128 is manually or mechanically pressed to force the cement 22 from the loading chamber 126 into the delivery passage 34 of the delivery cannula 18. The cement 22 flows around the beads 20 in the delivery passage 34 to at least partially fill the void spaces 63 by flowing or moving through the gaps G and into the void spaces 63. Furthermore, because the beads 20 are staggered within the delivery passage 34, adjacent beads 20 align along a wedge axis 123 with a wedge angle W defined between the wedge axis 123 and the central axis 50. After the delivery cannula 18 is loaded with the beads 20 and the cement 22, as the force is applied to the beads 20 by the push rod 24, the force is transferred through the adjacent beads 20 along the respective wedge axes 123. This may result in an increase in the overall force which is required to move the beads 20 and the cement 22 from the delivery cannula 18 and into the target site X.

Referring to FIG. 24B, as an alternative, the beads 20 and the cement 22 are loaded into the delivery cannula 18 using the 2-stage fill system 122 where the beads 20 and cement 22 are disposed in the loading chamber 126 of the container 124. Preferably, the container 124 is sized accommodate the beads 20 and sufficient spacing between and around the beads 20 such that the cement 22 easily flows through the beads 20 to fill spaces between the beads 20 and to surround the beads 20. The mover 128 is then inserted in the loading chamber 126 and the container 124 is coupled to the delivery cannula 18. The mover 128 is manually or mechanically pressed to force the beads 20 and the cement 22 from the loading chamber 126 into the delivery passage 34 of the delivery cannula 18. As a result, the beads 20 and cement 22 are now loaded into the delivery cannula 18 and define the void spaces 63 between adjacent beads 20 with the cement 22 at least partially filling the void spaces 63 in the delivery passage 34. This allows the beads 20 to be placed in a tight fitting linear array within the delivery passage 34 while still allowing the cement 22 to be sufficiently filled in the void spaces 63 between the beads 20. By aligning the beads 20 more linearly, the wedging of the beads 20 during delivery is reduced. As the wedging angle W increases, more friction builds between beads 20 and the delivery cannula 18.

Referring to FIG. 25, as another alternative, a parallel system 130 simultaneously delivers the beads 20 and the cement 22 to the interior of the vertebral body 12. The beads 20 and the cement 22 are preloaded into the delivery cannula 18 in separate delivery passages 34A, 34B. An alternative push rod 24A is inserted in the delivery passage 34 of the delivery cannula 18. The push rod 24A consists of two interconnected push rod portions 24B, 24C, extending in tandem. Each of the push rod portions 24B, 24C applies an equal force on the respective cement 22 and the beads 20. Alternatively, two independent push rods (not shown) may be used. The push rod portion 24C is moved along the delivery passage 34B to apply the force to the beads 20 to move the beads 20 through the delivery passage 34 and into the interior of the vertebral body 12. At the same time, the push rod portion 24B is moved along the delivery passage 34A to apply the force to the cement 22 to move the cement 22 into the delivery passage 34B and into the void spaces 63 between the beads 20. As a result, the cement 22 is introduced within at least a portion of the void spaces 63 in the delivery cannula 18 as the beads 20 move through the delivery passage 34, but before the beads 20 exit the delivery cannula 18 and enter the interior of the vertebral body 12. This allows the beads 20 and the cement 22 to be loaded into the parallel system 130 into separate delivery passages 34A, 34B while still allowing the beads 20 and the cement 22 to be delivered to the interior of the vertebral body 12 simultaneously.

Figure 8A:
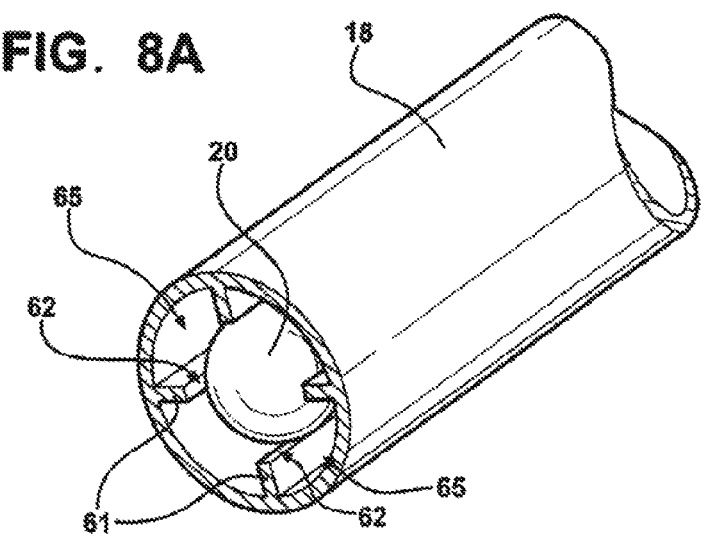
FIG. 8A is a cross-sectional perspective view of another alternative delivery cannulae.
Figure 8B:
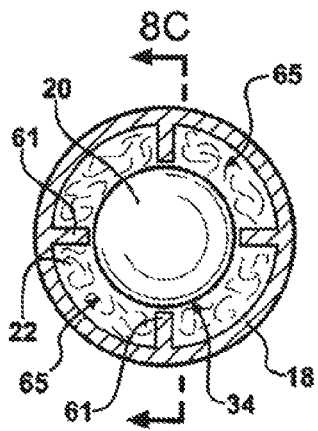
FIG. 8B is a cross-sectional end view of the delivery cannula of FIG. 8A.
Figure 8C:
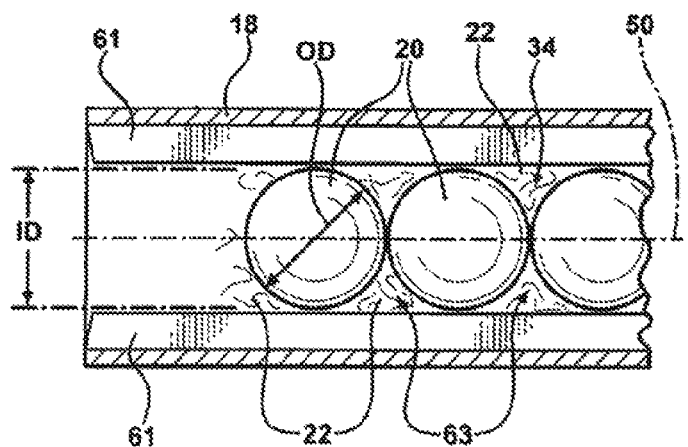
FIG. 8C is a cross-sectional side view of the delivery cannula of FIG. 8A.
Figure 12F:
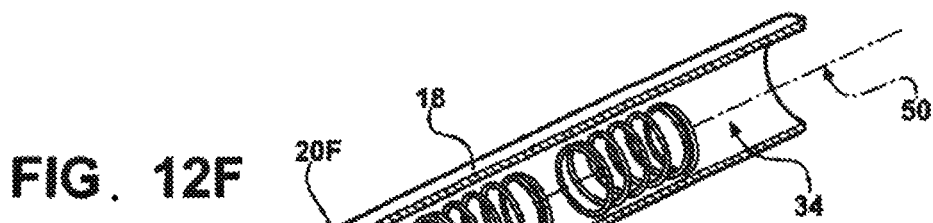
Figure 12G:
Figure 12H:
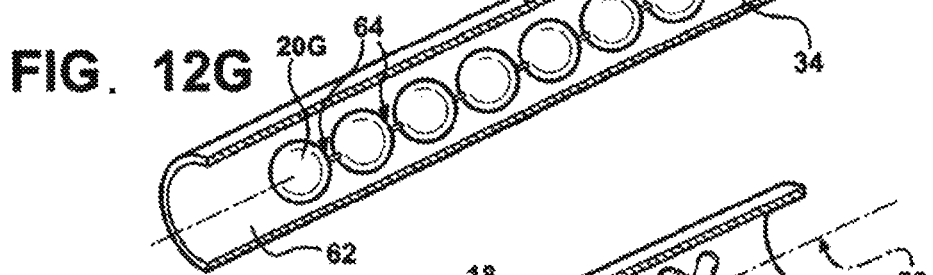
Figure 12I:
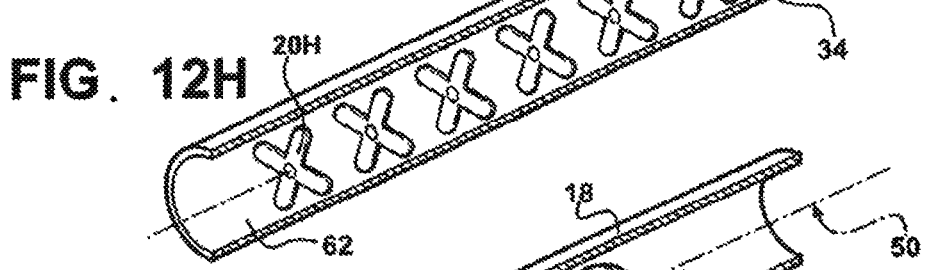

When working with relatively viscous mixed bone cement, it can be difficult to load the cement 22 into the void spaces 63 between the beads 20 when the gap G defined between the beads 20 and the delivery cannula 18 is small. An alternate method of loading the cement 22 into the void spaces 63 between the beads 20, but prior to delivery into the target site X is a 3-stage delivery system. A loading cannula with a cross-section as shown in FIGS. 8A-8C or FIG. 10, or a similar cross-section, can be loaded with appropriate sized beads 20, for example, spherical beads 20 with an outer diameter OD which fits within the inner diameter ID of the guide ribs 61, as shown in FIGS. 8A-8C. This loading cannula can then be connected to a fluent material source, such as a syringe-like device. The syringe can be used to create a pressure on the cement 22 so that the cement 22 flows down a passage in the loading cannula to exhaust the air from the passage of the loading cannula, filling the void spaces 63 between the beads 20. This loading cannula can then be connected to an empty delivery cannula 18. For example, a cylindrical delivery cannula 18 with an inner diameter ID that fits snugly to the outer diameter OD of the elements. A loading push rod can be inserted into the loading cannula and used to transfer the beads 20 and a portion of the cement 22 (e.g. cement 22 residing in the void spaces 63 defined between the beads 20). The transfer can occur through the application of a force on the first element 74 where that force acts through all subsequent adjacent beads 20 in order to move the mixture into the delivery cannula 18. The loading cannula and loading push rod can then be removed and a push rod 24 can be inserted into the delivery cannula 18 to deliver the implant mixture 20, 22 to the target site X as earlier described.

One advantage in this alternate loading method is when a delivery cannula 18 needs to fit into a smaller access cannula 16 or a smaller delivery cannula 18 is needed to fit into a limited anatomical bone space, the delivery cannula 18 described above would not be burdened with the additional radial size needed to load the relatively viscous cement 22. In other words, a delivery cannula 18 with a smaller diameter containing a mixture of cement 22 and beads 20 can be made available when needed. Another advantage of this 3-stage loading method is that when the beads 20 are constructed of a material which needs a larger surface area to support and align the beads 20 to be successfully delivered without lodging or wedging the beads 20 in the delivery cannula 18, a delivery cannula 18 without ribs 61 can be used. The delivery cannula 18 without ribs 61 would have a larger surface area to support and align the beads 20 as compared to a similarly sized delivery cannula 18 with ribs 61. This may allow the beads 20 to be delivered to the target site X and overcome resistance of the bone or tissue at the target site X, which may require a higher delivery force to dispense the implant mixture 20, 22.

B. Injecting the Agglomeration into the Vertebral Body

The beads 20 and the cement 22 are disposed in the interior of the vertebral body 12 by first inserting the access cannula 16 into the vertebral body 12 to provide access to the interior of the vertebral body 12. However, as noted above, the access cannula 16 is not required as the delivery cannula 18 may provide access to the interior of the vertebral body 12. Several known methods could be used to place the access cannula 16 in position. One such method includes using a stylet (not shown) inserted into the access cannula 16 to penetrate the tissue. Once in position, the stylet is removed from the access cannula 16, leaving the access cannula 16 in place.

Once the access cannula 16 is in place, the delivery cannula 18 is inserted through the access passage 29 in the access cannula 16 and into the interior of the vertebral body 12, as shown in FIG. 6. If used, the delivery mechanism 26 is attached to the push rod 24 and the delivery cannula 18, as shown in FIG. 1. The delivery mechanism 26 is attached to the delivery cannula 18 to hold the delivery cannula 18 relative to the push rod 24. The push rod 24 will apply the force on the beads 20 that are disposed in the delivery passage 34. When the delivery mechanism 26 is attached to the delivery cannula 18, the beads 20 and/or the cement 22 may already be loaded in the delivery passage 34 using, for example, the 2-stage fill system 122 discussed above. This depends on the type of loading system being employed. The trigger 86 mechanism of the delivery mechanism 26 is then actuated to move the push rod 24 along the delivery passage 34 of the delivery cannula 18 to apply the force on the beads 20 disposed in the delivery passage 34 of the delivery cannula 18.

As the beads 20 are forced from the delivery cannula 18 via the force applied by the push rod 24, the beads 20 are forced into the interior of the vertebral body 12 at a low pressure (discussed in more detail below). Additionally, the beads 20 simultaneously carry the cement 22 through the delivery passage 34 and into the interior of the vertebral body 12 upon application of the force to the beads 20 by the push rod 24. As a result, the beads 20 may compress the cancellous bone 14 within the vertebral body 12 and the cement 22 sets to a hardened condition to lock the beads 20 to one another and form the implant M. The cement 22 may also interdigitate with the cancellous bone 14 to further provide strength to the vertebral body 12.

During the procedure, the user may gauge the volume of the cement 22 delivered to the interior of the vertebral body 12 by measuring a linear distance the push rod 24 travels along the delivery passage 34 of the delivery cannula 18. From the linear distance, the volume of the beads 20 and the cement 22 can be calculated or estimated. This allows the user to better understand the volume of the beads 20 and the cement 22 already delivered and to estimate the volume of the beads 20 and the cement 22 still to be delivered to the interior of the vertebral body 12. Alternatively, the push rod 24 may include a gauge 132, such as markings along the push rod 24, indicating the volume of the cement 22 and the beads 20 delivered or the volume of the cement 22 and the beads 20 remaining in the delivery passage 34.

The user may perform the procedure using a fluoroscope (not shown). When using the fluoroscope, the beads 20 and/or the cement 22 are preferably radiopaque. This allows the user to gauge not only the volume of the beads 20 and the cement 22 delivered, but also to assess where the beads 20 and the cement 22 are entering and filling the interior of the vertebral body 12.

As an alternative, sensors (not shown) may be used for registering implant M, element, and system, parameters. In one embodiment, the system 10 includes a sensor or transducer for indicating the force applied to the beads 20 and/or the pressure applied to the cement 22 during delivery of the beads 20 and the cement 22 to the target site X. Closed loop feedback mechanisms may also be used to regulate the actions of the system 10, based on detector readings. For instance, such sensors may be used with the automatic system shown in FIG. 21 to provide closed loop feedback control of the system 10 based on force, pressure, or other parameters. Sensors may also be used to indicate the construct of the implant M. For example, a sensor may indicate the volume of the beads 20 delivered to the target site X, the volume of the beads 20 left in the delivery cannula 18, and/or the position of the implant M within the target site X. In one embodiment, the push rod 24 includes a force gauge (not shown) to detect a force applied by the push rod 24 on the beads 20 and the cement 22 being delivered.

The system 10 may also include a display capable of indicating any status measured by such sensors. Examples of the information that the display could indicate includes, but is not limited to, force applied, total volume, linear feed rate, volume feed rate, volume of beads 20 and/or cement 22 inserted, and/or volume of beads 20 and/or cement 22 remaining in the delivery cannula 18.

As the beads 20 are delivered to the target site X in the vertebral body 12, reaction forces transfer through the system 10 back to the user. The user manually controls and reacts to the reaction forces by delivering the beads 20 under the force to deform or displace the tissue, e.g., bone, at the target site X, to construct the implant M. The reaction forces are transferred as follows: (1) tissue resistance force, (2) beads 20 force, (3) push rod 24 force, and (4) driver force and/or manual force. The beads 20, when delivered to the target site X, define the interstitial gaps between the beads 20 inside the vertebral body 12. The cement 22 is transported by the beads 20 into these interstitial gaps and preferably sets to the hardened condition to lock the beads 20 to one another and form the implant M. Since the void spaces 63 defined between the beads 20 in the delivery cannula 18 correspond somewhat to the interstitial gaps between the beads 20 in the final implant M, pressure of the cement 22 can be controlled. As a result, the cement 22 can be delivered to the interior of the vertebral body 12 at a low pressure.

Furthermore owing to the nature of the cement, the cement that is immediately adjacent the beads, adheres to the beads themselves. This process can be considered the adhesion of the boundary layer cement. Owing to the cohesive nature of the cement to itself, the cement beyond the boundary layer cement remains bound to the boundary layer cement. These processes in addition to the fact that the gaps between the beads are relatively small, serve to minimize the extent to which the cement flows extravasatially from the vertebral body 12.

C. Pressure Control

Pressure in the system 10 can be controlled and/or modified by varying a volumetric ratio of the beads 20 to the cement 22. Consider the following three examples.

Example 1

If the volume of the cement 22 delivered from the delivery cannula 18 is equal to the final volume available for the cement 22 in the interstitial gaps provided by the beads 20 in the final implant M, then cement 22 does not have to be delivered by displacement (pressure), but is transported or carried solely by the beads 20. Therefore, the cement 22 experiences no pressurization in the final implant M. In this instance, the likelihood of the cement 22 leaking outside of the implant M is reduced. This condition is illustrated in FIG. 26A. This is advantageous for percutaneous treatment of vertebral compression fractures since the likelihood of cement 22 leaking from the vertebral body 12 due to pressurization in the cement 22 would be minimized.

Example 2

If the volume of the cement 22 delivered from the delivery cannula 18 is greater than the final volume available for the cement 22 in the interstitial gaps provided by the beads 20 in the final implant M, then at least a portion of the cement 22, i.e., the volume of the cement 22 equal to the volume difference, must be delivered by displacement and/or transported by the beads 20. Therefore, the cement 22 experiences a positive pressure and it would be expected that this pressure in the cement 22 will attempt to move until it finds a state of equilibrium within its surroundings at the target site X. As illustrated in FIG. 26B, when there is a positive pressure on the cement 22 the cement 22 moves to an outer boundary or periphery of the implant M. In some cases, it may be desirable to provide some of the cement 22 at the outer boundary of the implant M to better secure the implant M in the target site X, to bond with cancellous bone 14 outside of the implant M, and the like. Therefore, some pressure in the cement 22 may be advantageous if controlled, such as by the system 10 of the present invention. It should be noted that the volume of the cement 22 delivered in excess of the interstitial spaces between the beads 20 is a small percent of the total volume delivered. Therefore, it is expected that the cement 22 finds a state of equilibrium by displacing only a small volume of bodily fluids present in the vertebral body 12. This reduces the chances of extravasation.

Example 3

If the volume of the cement 22 delivered from the delivery cannula 18 is less than the final volume available for the cement 22 in the interstitial gaps provided by the beads 20 in the final implant M, then the cement 22 does not have to be delivered by displacement, but may be transported solely by the beads 20. Therefore, the cement 22 experiences a theoretical negative pressure and not all of the interstitial spaces between the beads 20 in the target site X are filled with the cement 22, as illustrated in FIG. 26C. It may be desirable to provide an implant M that is loosely packed in the target site X such that a volume of interstitial spaces between the beads 20 is greater than the amount of the cement 22 delivered to the target site X. This may be advantageous to facilitate tissue in-growth in the void spaces.

Examples 1, 2, and 3 may be desirable for different applications. Each of the examples can be achieved by using the disclosed low pressure design principles to select the volume of cement 22 delivered versus the volume of the beads 20 delivered and by analyzing the packing factors of the geometries of the selected beads 20. Thus, the system 10 can be designed to achieve desired delivery pressures of the cement 22 in the vertebral body 12.

The volumetric ratio may be modified by varying the outer diameter OD of the beads 20, the inner diameter ID of the delivery passage 34 and/or the minimum dimension T of the push rod 24. Additionally, the volumetric ratio may be controlled by controlling the volume of the cement 22 disposed within the void spaces 63.

Therefore, the system 10 may be customized to change the volumetric ratio of the beads 20 to the cement 22 delivered to the target site X to create the final implant M, as shown in FIGS. 26A-26C. Additionally, the user can control advancement of the beads 20, while the cement 22 is supplied in a dependent relationship to the advancement of the beads 20, as illustrated in FIG. 25. This relationship may also be variable, selectable, or independent of element 20 advancement to allow user input to control the volume of the cement 22 delivered relative to the volume of the beads 20 delivered, as illustrated in FIG. 21.

FIGS. 27A-27E illustrate different methods of varying a volumetric ratio of the beads 20 to the cement 22. It should be appreciated that the beads 20 and the cement 22 are preferably delivered to the interior of the vertebral body 12 at a volumetric ratio of the beads 20 to the cement 22 of from about 0.1:1 to about 10:1. More preferably, the beads 20 and the cement 22 are delivered at a volumetric ratio of about 2:1 to about 5:1. Most preferably, the beads 20 and the cement 22 are delivered at a volumetric ratio about 2:1. This occurs, for example, when the outer diameter OD of the beads 20 and the outer diameter of the push rod 24 is substantially equal to the inner diameter ID of the delivery cannula 18 and the cement 22 has a high viscosity, as shown in FIG. 27A.

Referring again to FIG. 27A, the beads 20 fit tightly within the delivery cannula 18. Additionally, the beads 20 are disposed adjacent one another and define the void spaces 63 therebetween. The volumetric ratio of 2:1 is achieved because the volume of beads 20 is twice the volume of the void spaces 63.

Using spherical beads 20 for illustration, the three primary variables involved in controlling these ratios include the outer diameter OD of the beads 20, the minimum dimension T of the push rod 24, and the volume of the cement 22 disposed in the void spaces 63, as discussed above. By varying one or more of these variables, the volume of the beads 20 delivered to the target site X, relative to the volume of the cement 22 delivered to the target site X, to form the implant M can be controlled. The variables and calculations used to customize the final implant M geometry will vary depending on the geometry of the delivery cannula 18, the push rod 24, and the beads 20. The following three examples assume a cylindrical push rod 24 and delivery passage 34 and a spherical element 20 where the inner diameter ID of the delivery cannula 18 and the outer diameter OD of the spherical element 20 are held constant with only the minimum dimension T of the push rod 24 being varied. Also, these examples are approximations and assume that a unit length movement of the push rod 24 displaces an equal volume of the mixture of the beads 20 and the cement 22 that are disposed in the path of the push rod 24. Therefore, the cement 22 that is carried by the beads 20 through surface tension may not be accounted for. For the purposes of these examples, assume the inner diameter ID of the delivery cannula 18 is 0.114 inches and the outer diameter OD of the spherical beads 20 are 0.083 inches. Thus, in each example, the volume of one element 20 is 2.994 (10E-4) in^3. Each of the following examples is calculated on a section that is equal in length to one element diameter. For purposes of illustration, the embodiment of the delivery cannula 18 shown in FIGS. 27B-27D correspond to the delivery cannula 18 shown in FIGS. 8A-8C.

Example 4

As illustrated in FIG. 27B, the minimum dimension T of the push rod 24 is 0.083 inches, which is equal to the outer diameter OD of the spherical beads 20. Thus, the push rod 24 volume per section is 4.491 (10E-4) in^3. The volume of the cement 22 delivered per section would be 1.497 (10E-4) in^3 and the ratio of the beads 20 to the cement 22 is 2:1.

Example 5

As illustrated in FIG. 27C, the minimum dimension T of the push rod 24 is 0.073 inches, which is smaller than the outer diameter OD of the spherical beads 20. Thus, the push rod 24 volume per section is 3.474 (10E-4) in^3. The volume of the cement 22 delivered per section would be 4.8 (10E-5) in^3 and the ratio of the beads 20 to the cement 22 is 6.25:1. This means that the volume of the cement 22 is much less than the volume of the beads 20.

Example 6

As illustrated in FIG. 27D, the push rod 24 extends into the grooves 65 and has an effective diameter of 0.098 inches (the cross-section of the push rod 24 is not circular), which is larger than the outer diameter OD of the spherical beads 20. The push rod 24 may be similar to the types shown in FIGS. 15-19. Thus, the push rod 24 volume per section is 6.261 (10E-4) in^3. The volume of the cement 22 delivered per section would be 1.497 (3.267E-4) in^3 and the ratio of the beads 20 to the cement 22 is 0.91:1. This means that the volume of cement 22 is almost equal to the volume of the beads 20.

In FIG. 27E, an example showing beads 20 that have an outer diameter OD which is less than one-half of the inner diameter ID of the delivery cannula 18 is shown. This example merely shows that multiple variations of the minimum dimension T of the push rod 24 and the outer diameter OD of the beads 20, as compared to the inner diameter ID of the delivery cannula 18, may be used to control the volumetric ratio of the beads 20 to the cement 22.

Referring again to FIGS. 8A-8C, another method of varying the volumetric ratio of the beads 20 to the cement 22 delivered is illustrated. Ideally, the grooves 65 are provided, as discussed above, to fill the voids spaces between the beads 20 and allow for simultaneous delivery of the beads 20 and the cement 22 and to also allow the cement 22 to backflow around the beads 20 such that pressurization of the cement 22 does not occur due to insufficient clearance between the spherical beads 20 and the delivery wall 61. However, it should be appreciated that the grooves 65 are not required for low pressure delivery as the geometry of the beads 20 may be selected to allow backflow, e.g., grooves or passage on the beads 20, or lesser amounts of cement 22 may be delivered. Additionally, as discussed above, if the head 68 is used, the head 68 may define the holes 70 or the gaps 72 between the head 68 and the delivery wall 61. Another variable to control (based on the previously defined variables), is the spacing between the push rod 24 and the delivery wall 62 of the delivery cannula 18, noted by "P" on FIGS. 27A-27E. This spacing P, the holes 70, and/or the gaps provide a volume available for the cement 22 to backflow into the delivery cannula 18 during use. As a result, this volume can also be used as storage for excess cement 22 to further control whether the cement 22 is delivered under pressure.

This configuration of internal guide ribs 61 and grooves 65 provides at least two benefits for this system. One benefit is a larger flow area for the cement 22 to pass in order to fill the void spaces 63 between the beads 20. When using a cement 22 with a relatively high viscosity, loading the cement 22 into the void spaces 63 can be difficult when the area between the beads 20 and the delivery wall 62 is small. Another benefit of this configuration is the guide ribs 61 can provide radial support to the beads 20, keeping the beads 20 more axially aligned along the delivery axis 36 in order reduce a radial component of the force transferred to the delivery walls 62. The frictional losses between certain element shapes (e.g. spherical elements) and the delivery cannula 18 would be reduced with better axial alignment and the likelihood of spherical or similar shaped elements to wedge or lodge in the delivery cannula is also reduced.

X. First Alternative Delivery Handpiece

Figure 28:
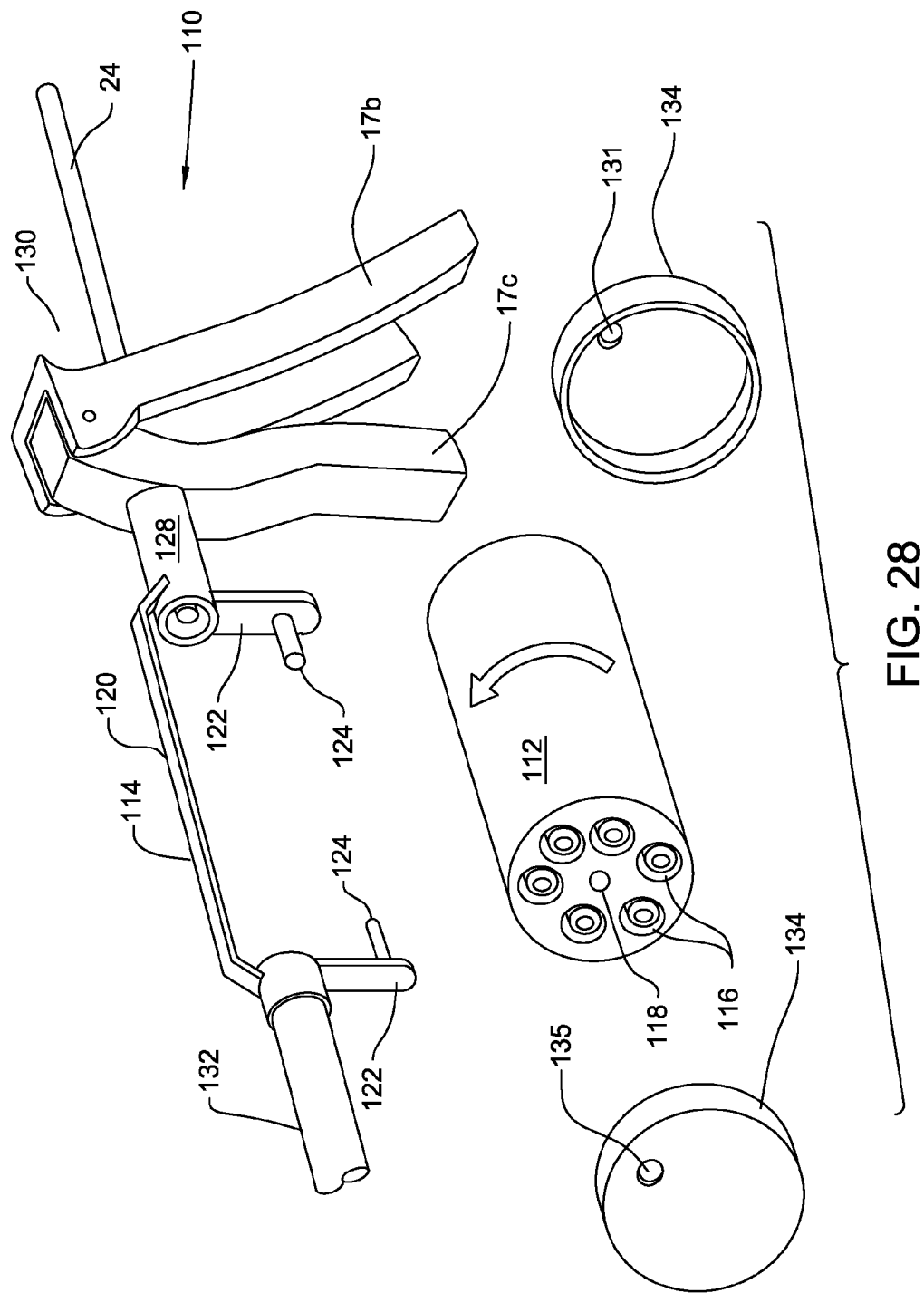
FIG. 28 is a perspective view of an alternative assembly for delivering the bead and cement (fluent) agglomeration into a bone.

FIG. 28 illustrates an alternative handpiece 110 for delivering the bead 20 and cement 22 agglomeration into the bone or other tissue. Handpiece 110 includes a cylindrical barrel 112 that is rotating suspended from a bracket 114. Barrel 112 is formed with a number of elongated bores 116 that extend the length of the barrel. Bores 116 are disposed in a circle that is located inward of the outer surface of the barrel. Each bore 116 contains a bead and cement agglomeration. Barrel 112 is further formed so that at the opposed ends there is a center located closed end bore 118.

Bracket 114 is generally in the form a U-shaped structure. There is a longitudinal bar 120 that has a length slightly greater than that of barrel 112. Extending downwardly from the opposed ends of bar 120 are two legs 122 that are parallel with each other. A pin 124 extends inwardly from the end of each leg 122 such that the pins are axially aligned and directed inwardly toward each other. When the handpiece 110 is assembled, barrel 112 is mounted to bracket 114 by the seating of the bracket pins 124 seat in the barrel bores 118.

Bracket 114 is further formed so that, extending proximally from the more proximal of the two legs 122 is guide tube 128. Guide tube 128 is dimensioned to receive the push rod 24. Attached to the proximal end of guide tube 128 is a drive unit 130. Drive unit 130, which may be similar to delivery mechanism 26, is constructed to advance the push rod through the guide tube 128 and the barrel bore 116 in alignment with the guide tube. Not identified are the tubular hubs between bars 120 and legs 122 in which the guide tube 128 and delivery cannula 132 are seated.

Extending distally from the proximal of the two legs 122 is the delivery conduit 132. Collectively, handpiece 110 is shaped so that guide tube 128 and delivery conduit 132 are aligned. Further, these conduits are positioned so that a barrel bore 116 can be placed in registration between them.

In handpiece 110 of this version of the invention the individual barrel bores 116 are loaded with bead and cement agglomerations. If necessitated by the particular procedure, the individual barrels can be loaded with agglomerations that have different: volumes; bead:cement mixture ratios; agglomerations with different types of beads; or agglomerations formed from cements having different properties.

Handpiece bracket 114 is formed from plastic or metal with the flexibility that allows the legs 120 to be flexed to facilitate the snap fitting of the barrel 112 to the bracket.

Once barrel 112 with the loaded bead and cement agglomerations is fitted to bracket 114, handpiece 110 is ready for use. A push rod 24 is inserted into an opening in the proximal end of drive unit 130. Drive unit 130 is actuated to cause the distal advancement of the push rod through, first the guide tube 128 and then through the aligned barrel bore 116. The advancement of the push rod 24 results in the rod forcing the bead and cement agglomeration out of the barrel 120, through the delivery cannula 32 and into the bone in which the implant M is to be formed. Once the agglomeration in one barrel bore 116 is discharged, the barrel can be rotated to place another bore 116 in registration with the delivery assembly so that the agglomeration contained in the second bore can be so delivered.

To so rotate the barrel 112 in order to place a new bore in registration with the delivery cannula 32, the push rod must be positioned so as to not inhibit barrel rotation. In some versions of the invention, the push rod is retracted from the barrel bore 116 in which the rod is seated. In these versions of the invention a disk-shaped head 136 is disposed in each barrel bore, as seen in FIG. 28A, is slidably disposed in the proximal end of each of the barrel bore 116. An O-ring 137 disposed around the perimeter of the head provides a seal between the head and the inner wall of the barrel defining the bore. When the push rod is actuated, the push rod abuts this head. The head 136 is the actual component that urges the bead and cement agglomeration out of the barrel bore 116. When the push rod 24 is retracted, to advance the barrel, the head 136 remains in the distal position. This arrangement prevents the push rod from coming into contact with the cement forming the agglomeration.

Alternative versions of the invention include distal and proximal push rods that are arranged in tandem with one another. When the discharge of an agglomeration in a particular barrel bore 116 is desired, a distal push rod is first inserted in the guide tube 128. This push rod may be selected based on diameter or length. Then, the proximal push rod is inserted. The drive unit works directly on the proximal push rod to advance it. The proximal push rod, in turn, urges the distal push rod forward to cause the discharge of the agglomeration. When the barrel bore is empty, the proximal push rod is retracted out of the barrel; the distal push rod is allowed to remain in the barrel bore 116.

In other versions of the invention, the push rod 24 is formed with frangible sections that break upon rotation of the barrel.

Handpiece 110 of this invention is designed so that that the length of the delivery cannula 32 from the proximal end of the barrel 112 to the point where the agglomeration is discharged inside the bone can be relatively short, 10 cm or less. This means the agglomeration only has to travel a relatively short distance before delivery into the bone. Furthermore, by using push rods of different diameters or lengths, the volume of the agglomeration discharged from each barrel bore can be controlled. These features, in combination with the fact the barrel bores 116 can be loaded with different types of agglomerations, means that the practitioner can construct an implant M that is formed out of agglomeration sections that have different bead or cement characteristics.

In some embodiments of the above version of the invention front and rear end caps 134 are fitted over the opposed distal and proximal ends of the barrel 112. These end caps seal the barrel bores 116 so as to both contain the agglomeration in the bore and slow the curing of the cement. Each end cap 134 is formed with a through opening 135. The end caps are mounted to the bracket 114 so as to remain static when the barrel 112 is rotated. The opening 135 associated with the rear end cap 134 allows the push rod 24 to be inserted into the aligned barrel bore. The opening 135 internal to the front end cap 134 functions as the through port through which the agglomeration is discharged through the delivery cannula 132.

In other versions of the invention, the cartridge formed with the multiple bores each for containing a portion of the bead and cement for delivery, may not be barrel shaped. In some versions of the invention, this cartridge for example could be rectangular. This cartridge is displaced linearly in order to place each agglomeration-filled bore inline with the pus rod.

XI. Second Alternative Delivery Handpiece

FIG. 29 illustrates a second alternative delivery handpiece 140 of this invention. Handpiece 140 includes a delivery cannula 142. Delivery cannula 142 can have the features of any of the previously described delivery cannulae. Removably attached to the proximal end of the delivery cannula is a cement charge tube 144. In one version of the invention, a circular coupling head 146 is fitted to the proximal end of the delivery cannula 142. The distal end of cement charge tube 144 is provided with a circular coupling foot 148. Cannula coupling head and Tube coupling foot 146 and 148, respectively, are formed with complementary features, (not illustrated) for releasably engaging the two components together.

A duck-billed valve or other valve (not illustrated) may be fitted in the proximal end of the lumen extending through the delivery cannula 142. This valve allows material to be inserted into this end of the cannula but prevents the beads from exiting the cannula through this end.

Handpiece 140 of this invention is used by first loading beads 20 into delivery cannula. The cement charge tube 144, with a volume of cement contained therein, is then coupled to the delivery cannula 142. Push rod 24 is then advanced through the cement charge tube 144. The advancement of the push rod 24 forces the cement into the delivery cannula lumen so as to form the bead and cement mixture. In some versions of the invention, in order to prevent the discharge of the beads through the distal end of the delivery cannula 142, prior to the injection of the cement 22, a cap or retainer (not illustrated) is fitted over the distal end opening formed in cannula. Also, the delivery cannula may be formed with internal ribs 61 (FIG. 8A). The cement, upon injection into the delivery cannula 142, will first flow into the arcuate spaces between the ribs 61. A fraction of the cement will then flow between the beads.

Once bead and cement agglomeration is formed. the cement charge cannula 144 is decoupled from the delivery cannula. The distal end of the delivery cannula is uncapped/unplugged and inserted into the bone in which the implant M is to be formed. Push rod 24 is inserted in the proximal end of the delivery cannula 142 in order to advance the agglomeration into the bone.

Handpiece 140 of this invention is constructed so that the bead and cement agglomeration is formed inside the delivery cannula. This eliminates both the need to provide a larger mixing chamber and an assembly for transferring the agglomeration into the delivery cannula.

In an alternative version of the invention, a push rod of sufficient length that it extends through both the charge tube 144 and delivery cannula 142 is provided. With this version of the invention, by actuating the single push rod, the cement is first forced into the delivery cannula 142 in order to form the agglomeration. The continued advancement of the push rod results in the rod forcing the agglomeration out of the delivery cannula into the bone. In these versions of the invention, the delivery cannula 142 and cement charge tube 144 can be formed as a single unitary structure.

XII. Third Alternative Handpiece

Figure 30:
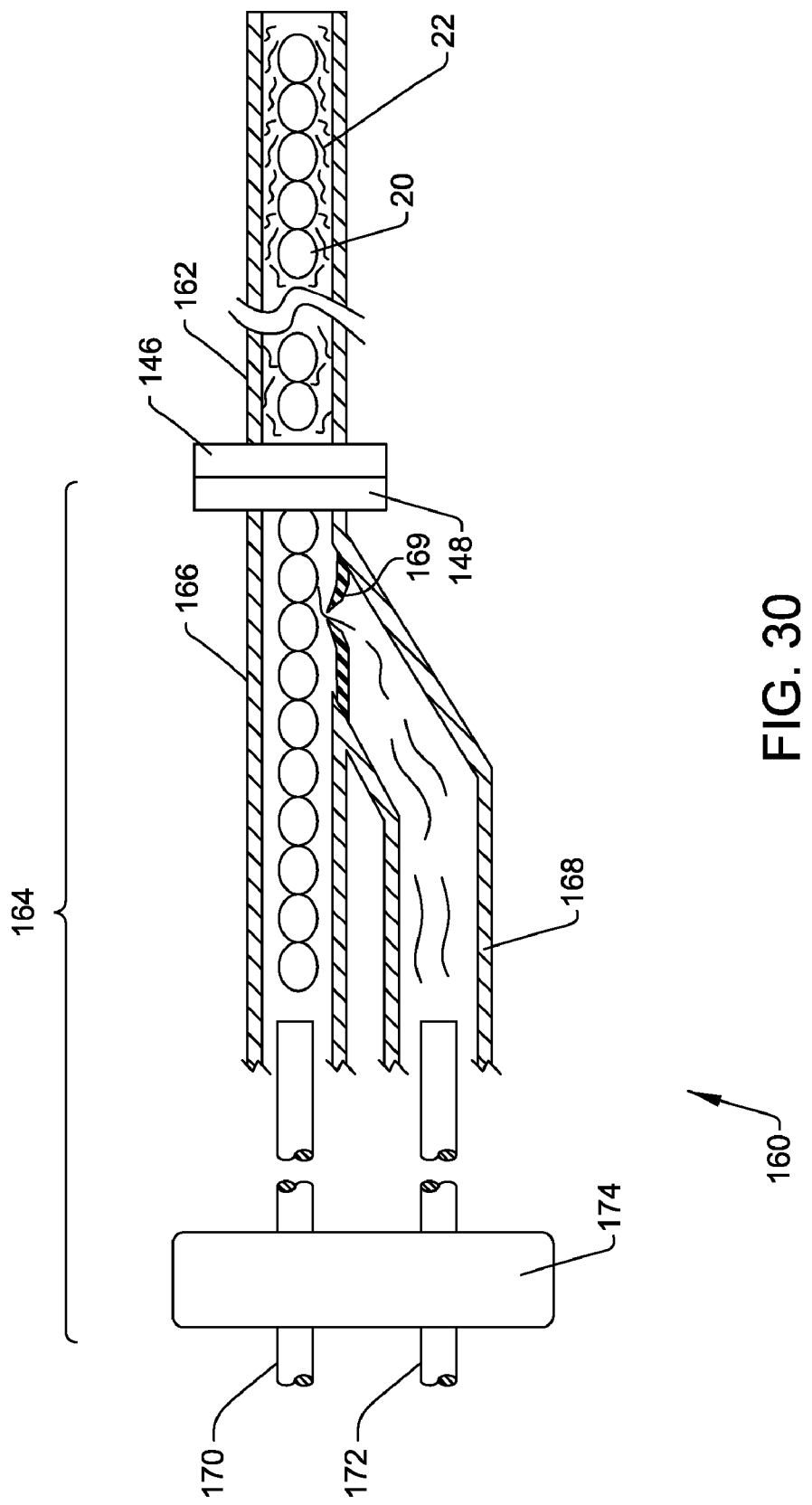
FIG. 30 is a cross sectional view of an alternative assembly of this invention capable of mixing the beads and cement together to form the agglomeration and thereafter delivering the agglomeration to the bone.

FIG. 30 illustrates another alternative handpiece 160 of this invention. Handpiece 160 includes a delivery cannula 162. Attached to proximal end of delivery cannula 162 is a mixing unit 164. In the illustrated versions of the invention, delivery cannula 160 is provided with the previously described coupling head 146. A coupling foot 148 at the distal end of the mixing unit 164 removably holds the mixing unit to the delivery cannula 162.

Mixing unit 164 includes two tubes. A first tube is the bead storage tube 166. A second tube is the cement charge tube 168. At their proximal ends, tubes 166 and 168 are parallel. Slightly rearward of the forward distal end of the mixing unit 164, cement charge tube 168 angles towards and intersects with the bead storage tube 166. Bead storage tube 166 extends forward from the point where the two tubes 166 and 168 intersect. Coupling foot 148 is attached to the distal end of the bead storage tube. Consequently, when the mixing unit 164 is coupled to the delivery cannula 162, the bead storage tube 166 is in axial alignment with the delivery cannula 162.

A valve 169 is disposed in bead storage tube 166. Valve 169 is seated in the side opening into tube 166 where cement charge tube 168 opens into the bead storage tube 166. Valve 169 is duck billed valve or other valve that allows flow from the cement charge tube 168 into the bead storage tube 166 but not in the opposite direction.

Handpiece 160 includes two separate push rods 170 and 172. Push rod 170 is positioned to be inserted in the proximal end of the bead storage tube 166. Push rod 172 is positioned to be inserted in the cement charge tube 168. Both push rods 170 and 172 are shown extending through a drive block 174. Drive block 174 including clamping mechanisms, (not illustrated) that allow the push rods to each slide relative to the block 174 or move with the block. When both push rods 170 and 172 are clamped to the drive block 174, the rods move in unison.

Handpiece 170 of this version of the invention is prepared for use by filling the bead storage tube 166 with beads 20 and filling the cement charge tube 168 with cement 22. Once the delivery cannula 162 is fitted to the bone which the implant is to be formed, the mixing unit 164 is coupled to the cannula 162.

The bead and cement agglomeration is then formed and then almost immediately after formation, ejected into the bone. Specifically, push rods 170 and 172 first advance the cement into the bead storage tube 166 to form the agglomeration and then deliver the agglomeration into the bone. To perform these processes, the push rods 170 and 172 are advanced in a series of steps. These steps may involve both sequential and simultaneous advancement of the push rod. For example, in one method of using handpiece 160, push rod 172 is initially advanced. This causes an initial head of cement to flow into the bead storage tube 166. This initial cement flow coats the beads located in the distal end of the tube 166 so as to form the initial head of the agglomeration. Both push rods 170 and 172 are then locked to the drive block 174. Drive block 174 is then advanced distally. The resultant simultaneous advancement of the push rods 170 and 172 results in the simultaneous injection of the agglomeration into the bone and the continued formation of the agglomeration at the point when the contents of the cement charge tube 168 feed into the bead supply tube 166.

The above version of the invention is thus constructed so that, almost immediately after the agglomeration is constructed, it is injected into the bone in which the implant is to be formed. Thus, handpiece 160 of this version of this invention is well suited for use with cement that is fast curing or quick to bind or otherwise interact with the beads 20. This is because the mixing of the agglomeration followed by its near simultaneous delivery, both in the handpiece 160, substantially reduces the likelihood the cement may bind so quickly to the beads that agglomeration will not form into an implant M having the desired shape. This near simultaneous forming and delivery of the agglomeration likewise substantially eliminates the agglomeration will harden in, and therefore clog, the delivery cannula 162.

In an alternative version of this invention the cement charge tube comprises a cannula that is disposed around the delivery cannula (version not illustrated). In these versions of the invention, the annular space between the two tubes functions as the space in which the cement is stored prior to agglomeration mixing. The delivery cannula is formed with openings located within the portion of the cannula surrounded by the cement charge tube. The cement is discharged through these openings to mix with the beads.

XIII. Implant Formed with a Containment Shell

Figure 31A:
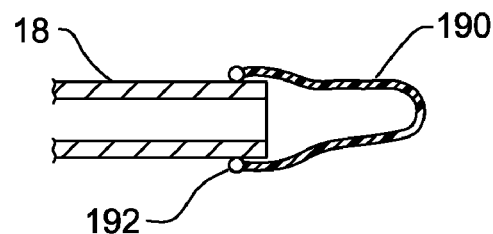
FIG. 31A is a side view of how a membrane is fitted over the end of a delivery cannula.

This invention may also be used to form an implant M that includes a containment shell. In order to form such an implant, a membrane 190, seen in FIG. 31A, formed of expandable material such as silicon rubber (impermeable) or woven PMMA fibers (permeable), woven silk (permeable) or urethane (impermeable). is fitted on the end of the delivery cannula 18. A small collar 192 formed of elastomeric material such as silicon rubber is disposed over the open end of the balloon. Ideally, the material forming collar 192 is such that, were the ring not expanded, it would contract to the position wherein it would substantially close the membrane 192. The tendency of collar 192 to want to contract serves to hold the ring and, by extension, the membrane 190 to the cannula 18.

Figure 31B:
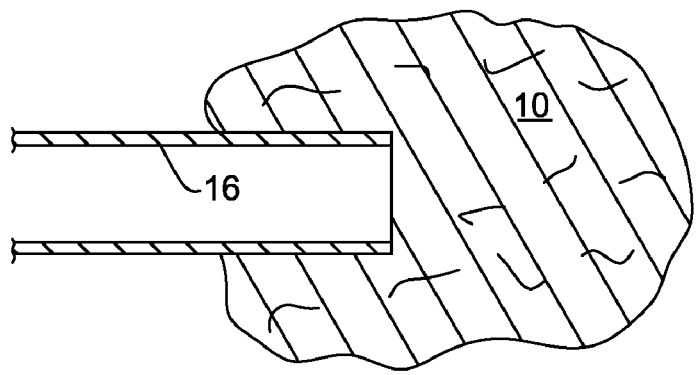
FIGS. 31B-31H are a series of cross sectional views illustrating how an implant comprising an agglomeration contained within a membrane is formed according to this invention.
Figure 31C:
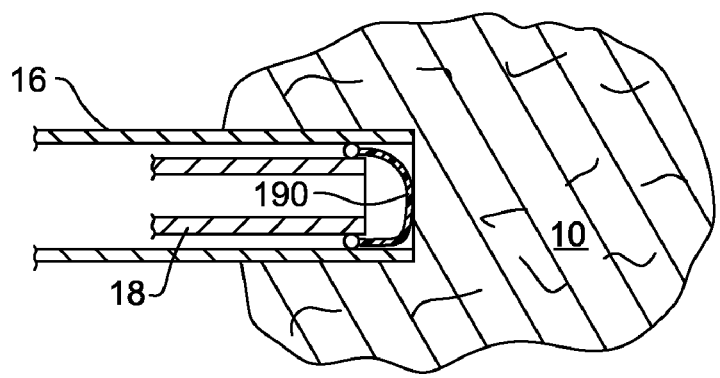

An implant with membrane 190 is formed by first inserting the access cannula 16 into the bone in which the implant is to be formed, FIG. 31B. The delivery cannula 18, with membrane 190 attached is then inserted into the distal end of the access cannula 16, FIG. 31C. In this version of the invention, cannulae 16 and 18 are dimensioned so that there is a sufficient annular gap therebetween through which membrane collar 192 can transit. In FIG. 31C and the additional Figures, membrane 190 is shown as single layer structure. In actuality, upon insertion, the membrane may be folded over on itself a number of times to facilitate insertion into the bone. Membrane 190 may also be housed in the open distal end of the delivery cannula.

Figure 31D:
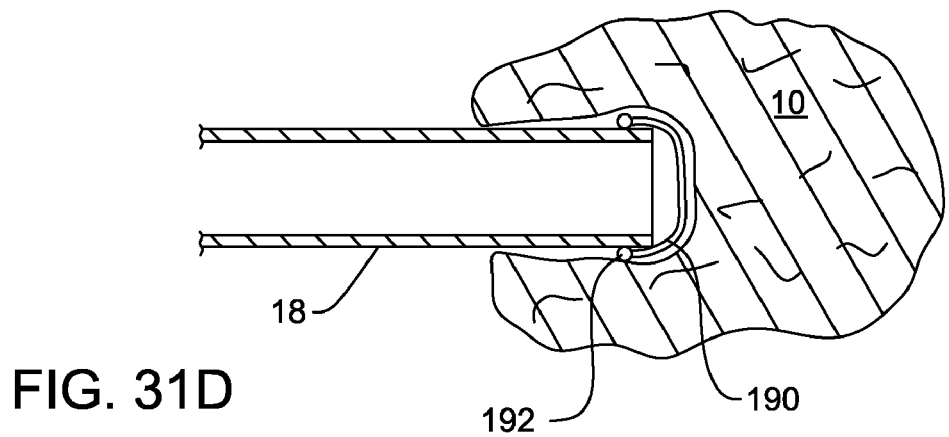

Access cannula 16 is then withdrawn from the bone, FIG. 31D. This method of inserting membrane 190 reduces the likelihood of the membrane hanging up or snagging on tissue in its initial placement.

Figure 31E:
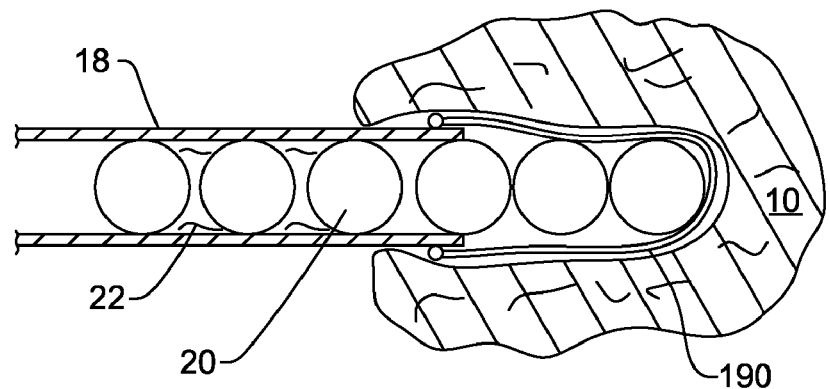
Figure 31F:
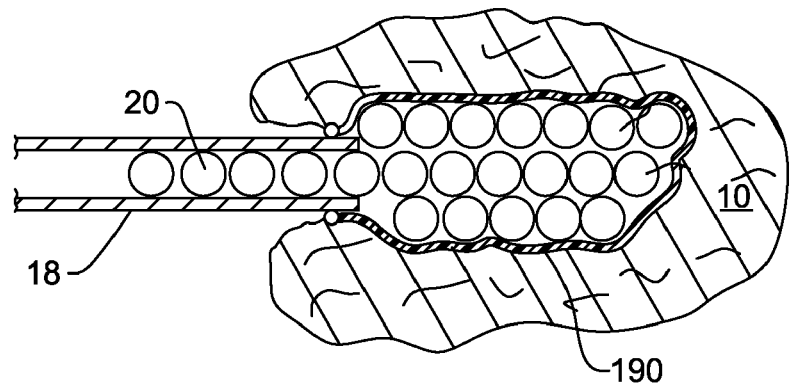

The bead and cement agglomeration is then injected into the bone. More particularly, as seen by FIG. 31E, the bead and cement agglomeration is injected out of the delivery cannula 18 into the membrane 190. The beads forming the agglomeration both expand the membrane and compress the surrounding cancellous bone tissue so as to form a space for receiving the implant, FIG. 31F. Eventually, the implant has the desired size.

Figure 31G:
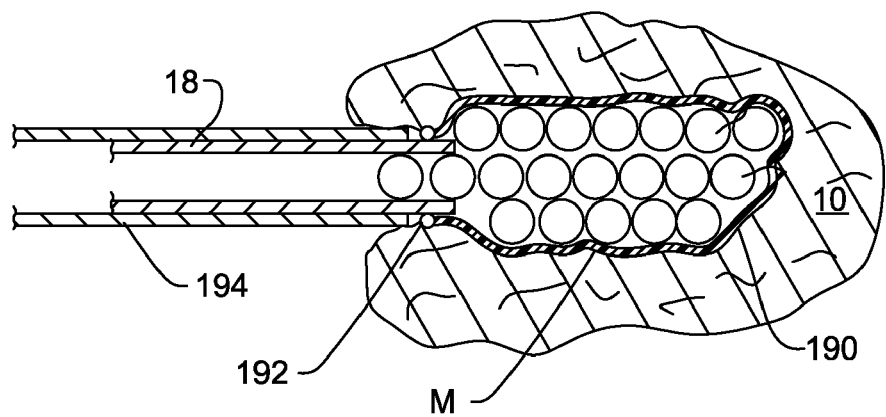

Upon the implant reaching the desired shape, an extraction tube 194 is slide over delivery cannula 18, FIG. 31G. Extraction tube 194 has an inner diameter selected to allow the tube 194 to closely slip fit over the delivery cannula 18. Consequently, when the extraction tube 194 reaches the distal end of the delivery cannula 18, the tube 18 pushes membrane collar 192 off the cannula 192. Owing to the nature of the material forming collar 192 to contract inwardly, the collar 192, once off the cannula 18 substantially closes the opening into the membrane 190. The discharge cannula 18 and extraction tube 194 are then removed from the bone.

Figure 31H:
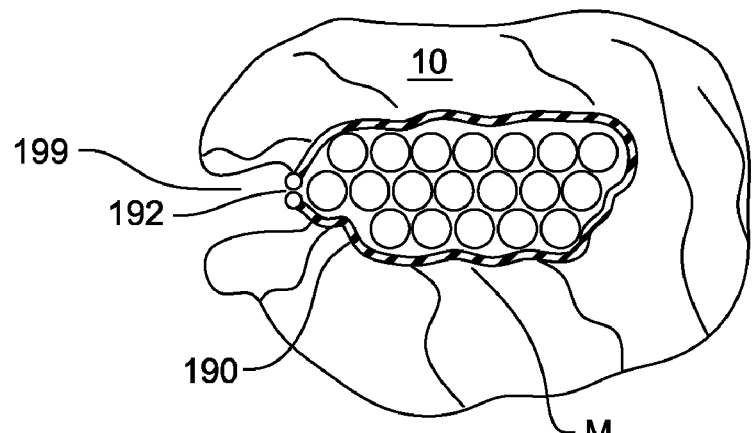

Once the discharge cannula 18 and extraction tube 194 are so removed all that remains is an implant 198 comprising the encased in membrane 190 bead and cement agglomeration, FIG. 31H. It should be appreciated that in this version of the invention as well as other versions of the invention, once the agglomeration forming the implant is delivered and the delivery cannula is formed, a small opening 199 is left in the outer cortical layer of the bone. Over time, there is some regrowth of this tissue so as to close off this opening. Some practitioners at the conclusion of performing a vertebroplasty are known to pack bone cement in the opening 199 in order to plug it.

Thus, in this version of the invention, membrane 190 forms a shell around the fluid component of the implant, the cement 22. This shell, if liquid impermeable, blocks flow of the cement into the bone. If the material forming the shell is porous, the cement may flow into the pores. Owing to the viscous nature of many cements as they cure, the material forming the shell initially at least slows the extravasation away from the implant. Then, as the cement hardens in the pores, further flow of the cement away from the implant is blocked. further, if the material forming the shell is porous, the hardened cement causes the shell to likewise harden. The resultant implant with the hardened shell is then less likely to suffer fracture.

XIV. Second Implant Formed with a Containment Shell

FIGS. 32A, 32B and 32C illustrate an alternative balloon 210 for forming an implant with a shell. Balloon 210 include an inner liner 212 encased within an outer liner 214. A set of webs 216 extend between the liners 212 and 214. Webs 216, for reasons that are apparent below are not continuous. In other words, the webs do not extend as solid walls between the liners 214 and 216. Inner liner 212 is formed to have an inlet neck 218. Outer liner 214 has an inlet neck 220. Inner tube inlet neck 218 is disposed within the outer tube inlet neck 220.

In this version of the invention, inner liner 212 and the webs 216 may be formed from porous material. The outer liner 214 may be formed from impermeable material.

Figure 32D:
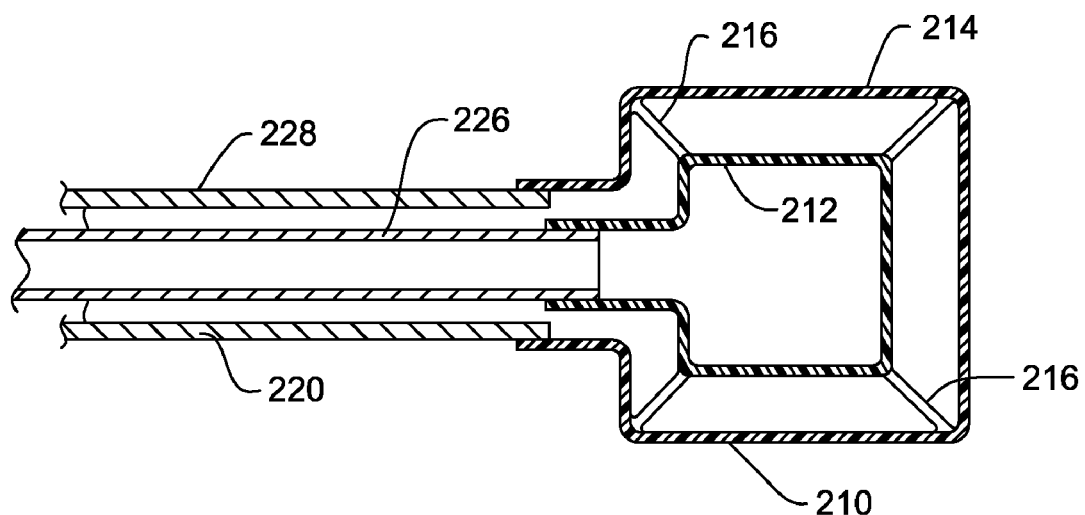
FIG. 32D is a cross sectional view of a delivery assembly constructed to deliver both cement and the bead-and-cement agglomeration into the balloon of FIGS. 32-32C.

In this version of the invention, balloon 210 is attached to the distal end of a cannula 224, seen in FIG. 32D. Cannula 224 is constructed to have concentric inner and outer tubes 226 and 228, respectively. Inner tube 226 has an inner diameter sufficient to allow the cement and bead agglomeration to be flowed through the tube. The outer diameter of the inner tube 226 is such that the balloon inner liner neck 218 can tightly fit over the distal end of the tube. The outer tube 228 is shaped to have an inner diameter of sufficient size that there is annular gap between the two tubes 226 and 228. Not shown but present in some versions of the invention are spars that extend between the tubes 226 and 228 to stabilize the inner tube 226 within the outer tube 228. Outer tube 228 has an outer diameter such that balloon outer liner neck 218 tightly fits over the distal open end of the tube.

In the depicted version of the invention, balloon 210 is constructed so that outer liner neck 220 extends forward of the underlying inner liner neck 218 Cannula 224 is constructed so that inner tube 225 extends a slight distance forward of outer tube 228. This arrangement facilitates the fitting of the liner necks 218 and 220 over the respective tubes 226 and 228.

Balloon 210 is initially lodged in the bone using the same method used to lodge membrane 190 (FIGS. 31B and 31C). A bead and cement agglomeration is then flowed through the delivery cannula inner tube 226 into the balloon inner liner 214. Cement is flowed in the annulus between the two tubes 226 and 228 into the space between the liners 214 and 216.

In the method of forming the implant of this invention, one or a combination of methods may be employed to ensure that the cement flows into the space between the liners. In one method, after the agglomeration at least partially expands the balloon to compress the surrounding bone the cement is delivered to the balloon under relatively high pressure. In an alternative method, after the agglomeration is used to expand the balloon/compact the bone a slight suction is drawn on the proximal end of the inner tube. This suction results in a partial draw of the cement out of the balloon. However, the cavity created by the compaction of the bone remains present. At this stage, a small amount of cement is injected into the balloon so as to flow between the inner and outer liners 212 and 216, respectively.

Owing to the permeable nature of the inner liner 212 some cement extends across and hardens in the liner 212. The impermeable nature of the outer liner prevents leakage of the cement outside of the cavity in which the implant is to be formed.

The implant formed using balloon 210 thus has a core formed of the hardened bead and cement agglomeration. This implant also has a shell formed of cement. An advantage of this arrangement is that since the shell is formed from a substantially uniform material, the cement, this material has a substantially constant deformation characteristics. Consequently, when the implant is subjected to surface loading, the material forming the shell, will not, due to unequal delaminate from itself.

In an alternative version of the invention, inner liner 212 is formed from impermeable material and outer liner 214 is formed from permeable material. In an implant formed with this type of balloon the small fraction of the cement contained between the liners is forced out of the outer liner 214 to bond with the surrounding bone. The material forming the inner liner 212 holds the cement internal to the agglomeration in place to prevent its leakage from the implant.

Alternatively, both balloon liners are formed with impermeable or permeable material.

XV. Third Implant Formed with a Containment Shell

Figure 33A:
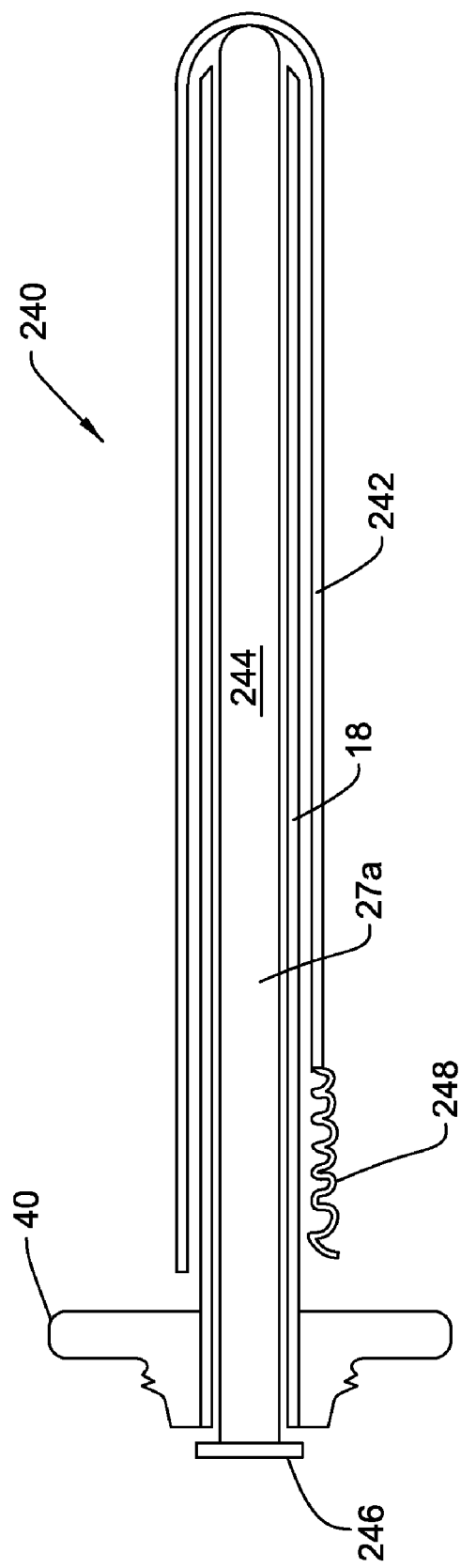
FIG. 33A is a side view of the sock employed as containment member for the implant constructed in accordance with this invention.
Figure 33B:
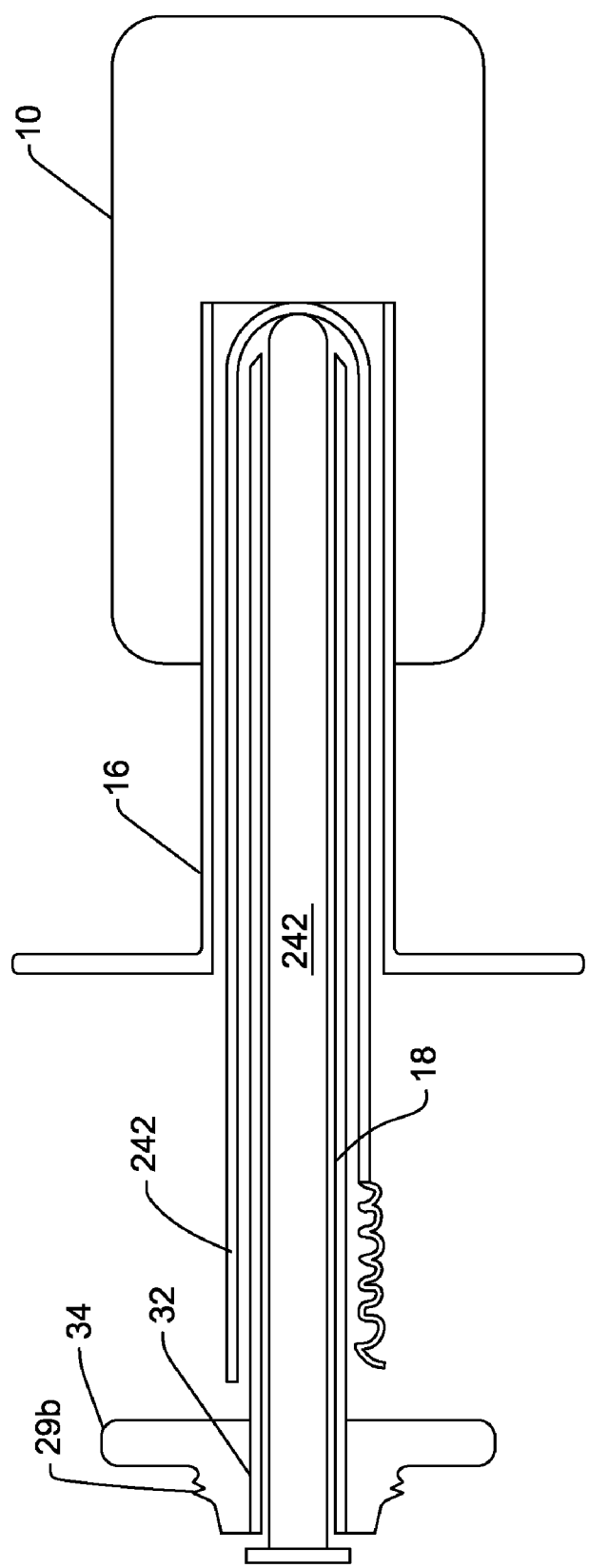
FIG. 33B-33I are a series of cross sectional views illustrating an alternative means of forming an implant consisting of an agglomeration within a membrane according to this invention.

Assembly 240, now described with respect to FIG. 33A is also used to form an implant with a containment shell according to this invention. Assembly 240 includes the previously described delivery cannula 18. Fitted over the delivery cannula 18 and extending along a substantial length of the cannula is sock 242. Sock 242 is formed from one of the materials from which the previously described membrane 190 or balloon 210 are formed. Disposed inside the delivery cannula 240 is a rod like stylet 244. The distal end of the stylet 244 is rounded. This geometry minimizes the likelihood of tearing of the overlapping section of sock 242. Stylet 244 is shaped so that the proximal end extends rearward of the delivery cannula 18. A handle 246 is attached to the exposed proximal end of the stylet to facilitate the removal of the stylet from the delivery cannula 18.

In FIG. 33A the proximal end of sock 242 is shown as having pleats 248 at one end. This is to represent that the sock may have an excess section that is allowed to expand as the sock forms the bone implant.

Figure 33C:
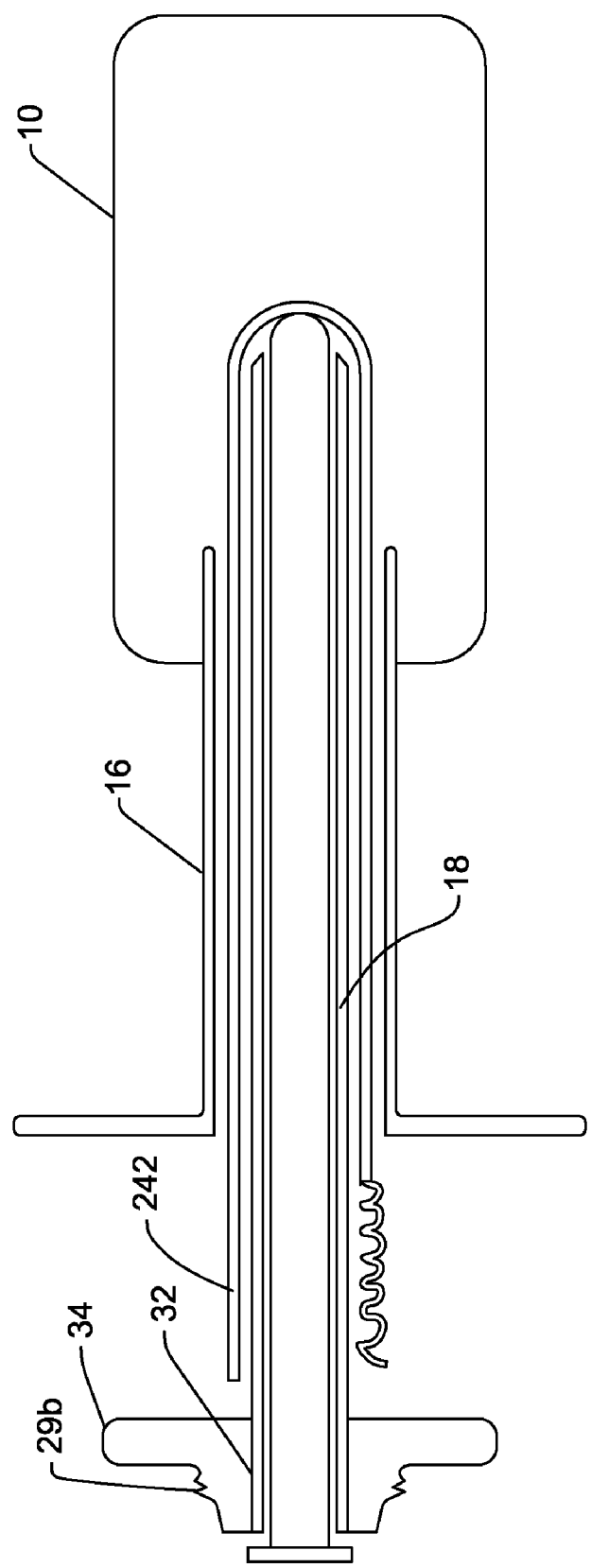
Figure 33D:
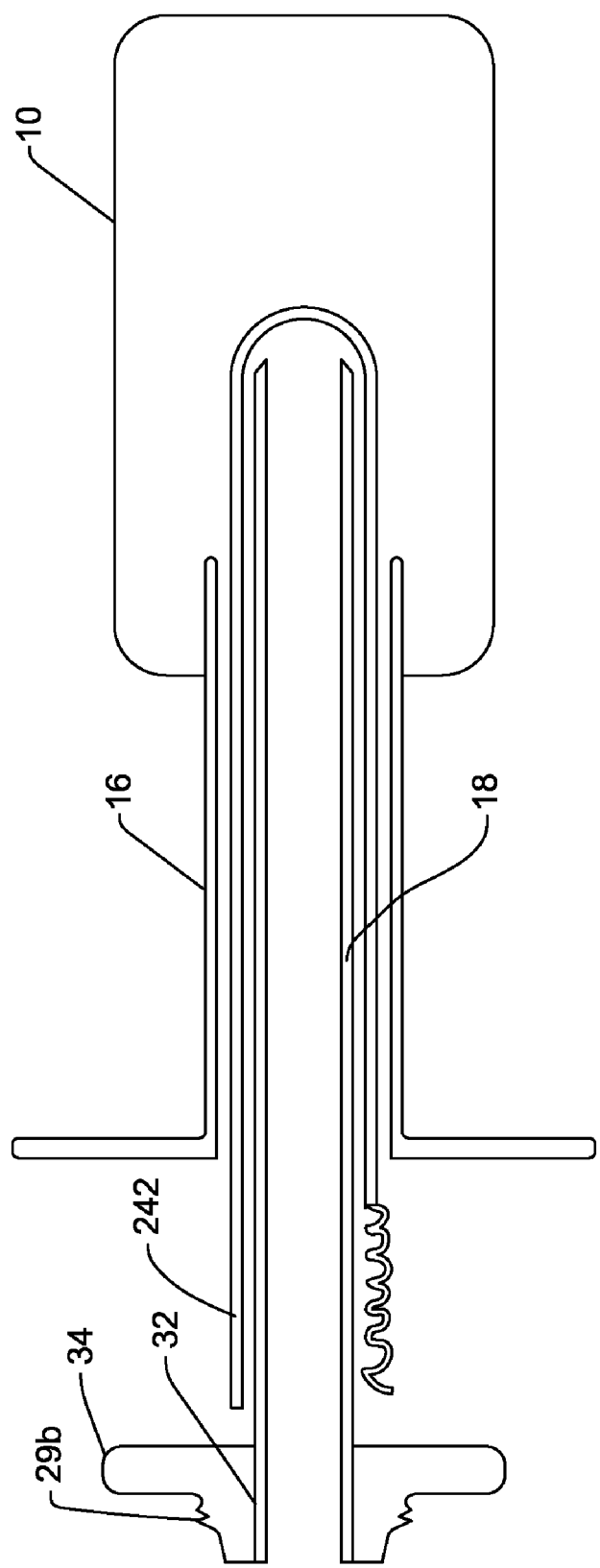

In order to use assembly 240 to form an implant the access cannula 16 is first inserted in the bone 10. The access cannula 16 is shaped so as to have sufficient inner diameter that the assembly 240, the sock 242 over the delivery cannula 18, can be fitted into the cannula lumen. Once the access cannula 16 is properly positioned, assembly 240 is inserted down the lumen of the cannula 16, FIG. 32B. The access cannula is then at least partially withdrawn from the bone, FIG. 33C. Stylet 244 is completely removed from the central lumen of the delivery cannula, FIG. 33D.

Figure 33E:
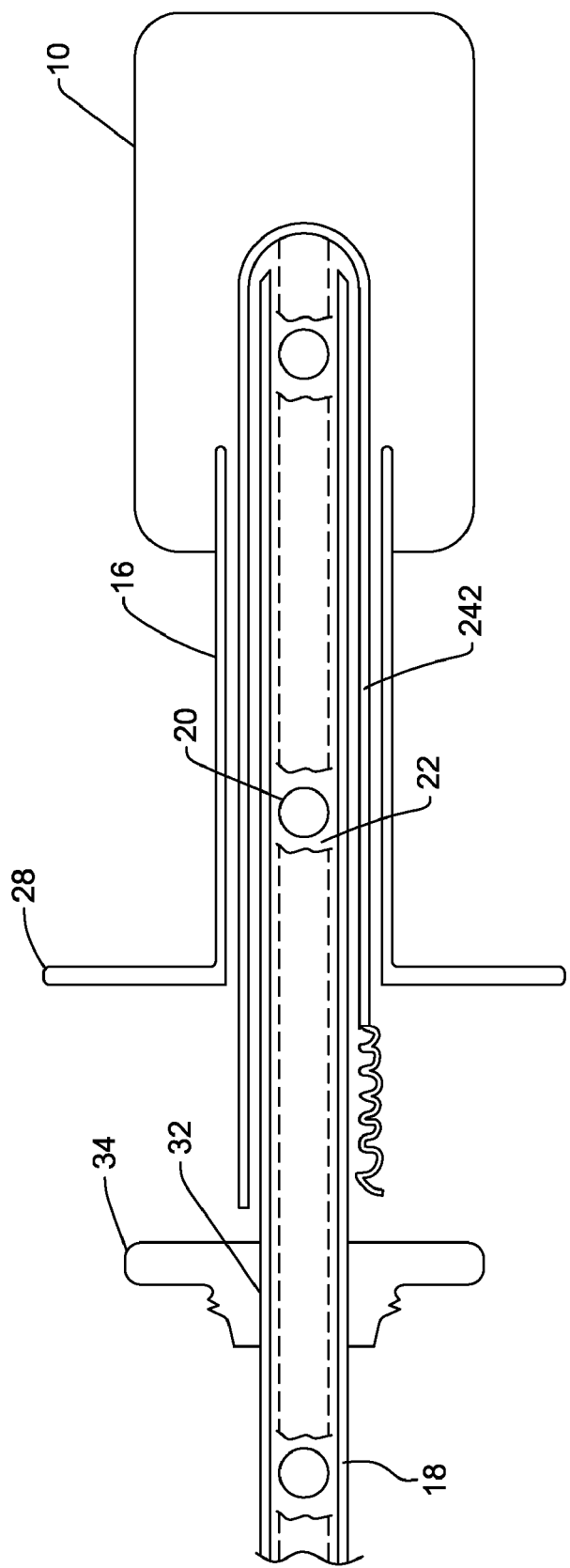
Figure 33F:
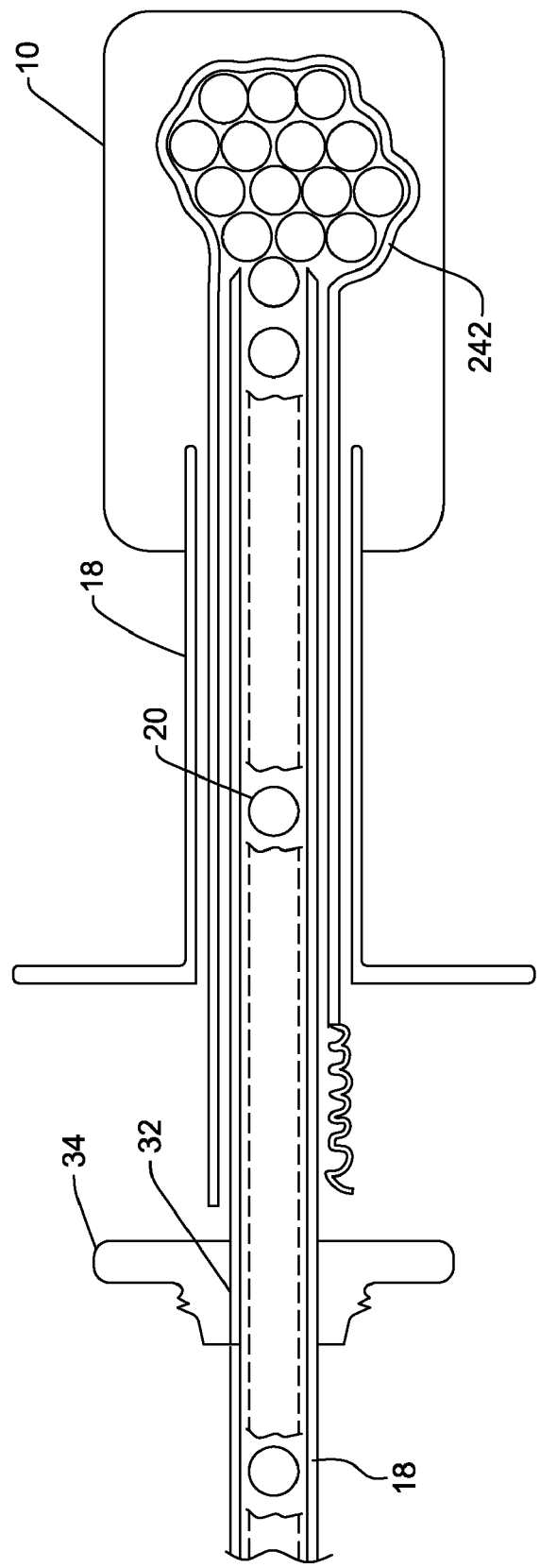

The actual formation of the implant can then begin. this process involves using any of the foregoing methods to advance a bead and cement agglomeration out the distal end of the discharge cannula 18. From the discharge cannula, the beads compress the cancellous bone to form the cavity in which the implant is disposed. The agglomeration also expands and remains contained in the sock 242, FIGS. 33E and 33F. As in versions of this invention wherein the implant is encased in a membrane 190 or 210, the sock 242 contains the material forming the implant so as to prevent its extravasation outside of the bone.

Figure 33G:
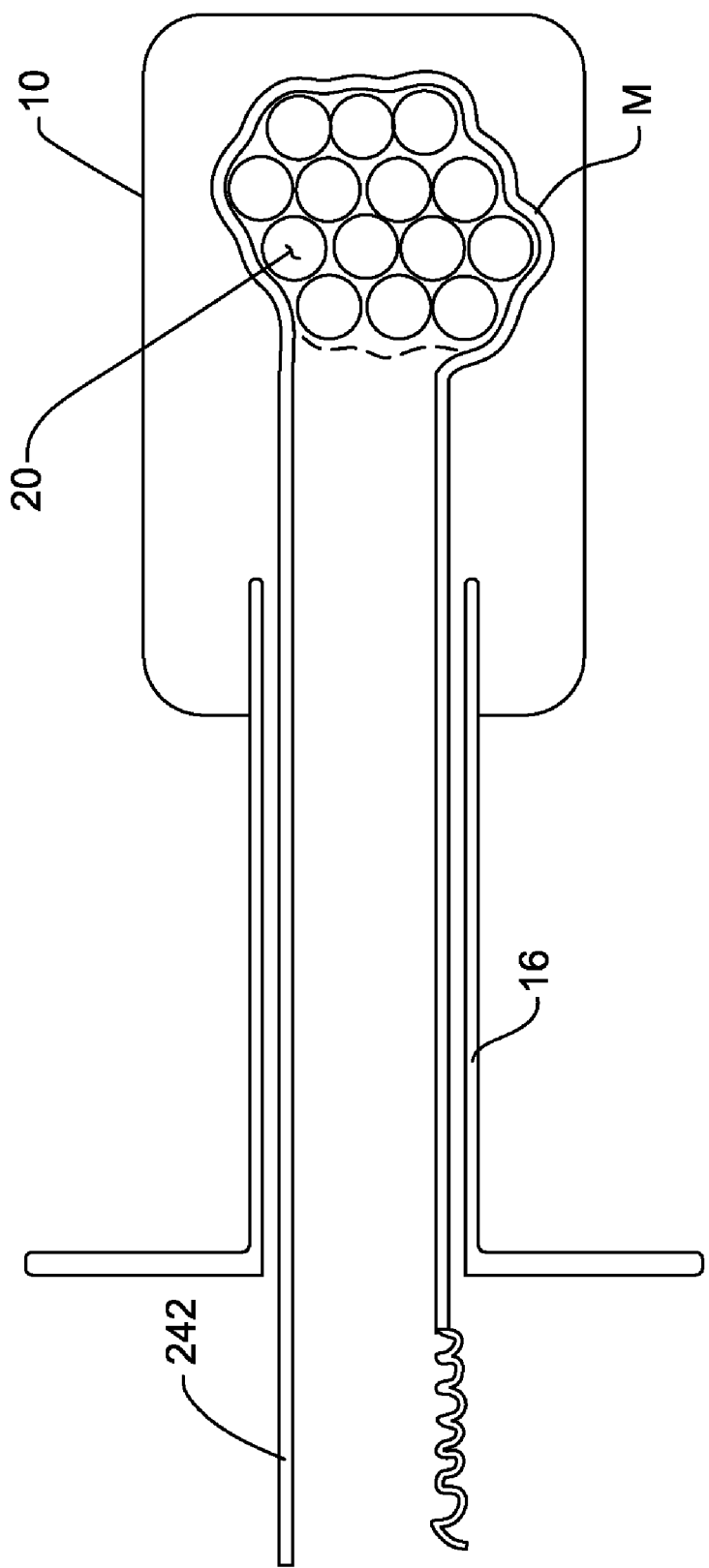
Figure 33H:
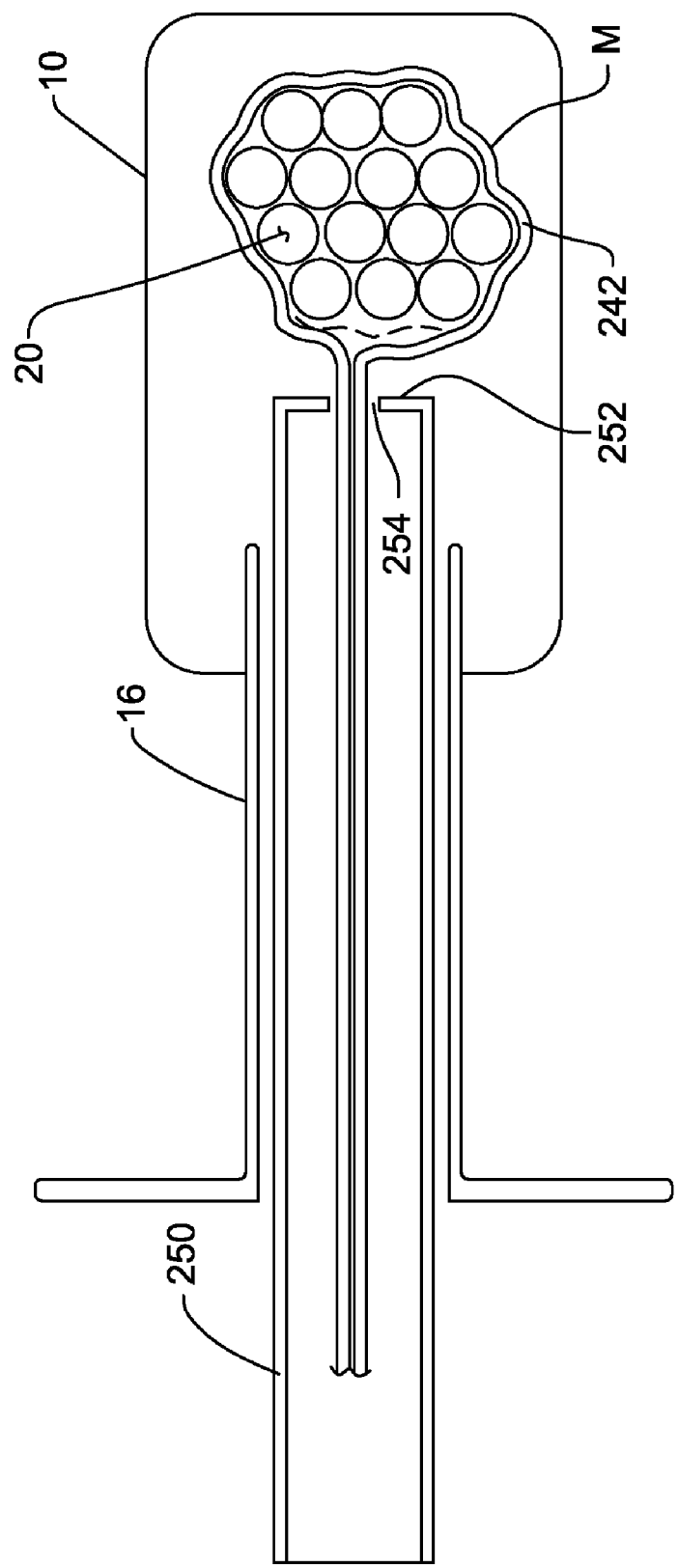

Eventually an implant of desired size and shape is formed. Once this occurs, the sock is closed. This portion of the procedure begins with the withdrawal of the delivery cannula 18 from the bone 10, FIG. 33G. A cut-off tube 250 is then inserted down the access cannula 16, FIG. 33H. Tie off tube 250 has a elongated tubular shaft 252. At the distal end of the shaft is a disk shaped head 252. An opening 254 extends through head 252. While not illustrated it should be understood that at least one portion of the inner circumferential edge of head 252 that defines opening 254 may be formed with a beveled profile. This portion of the head functions as a knife edge for purposes to be discussed below.

One of the initial steps of inserting the cut-off tube 250 down the access cannula comprises compressing the proximal end of the sock 242 into a narrow diameter strand 256. This strand is then inserted in tube opening 254. The continued advancement of the cut-off 252 tube toward the implant results in the continued compression of the section of portion of the sock spaced from the implant.

Figure 33I:
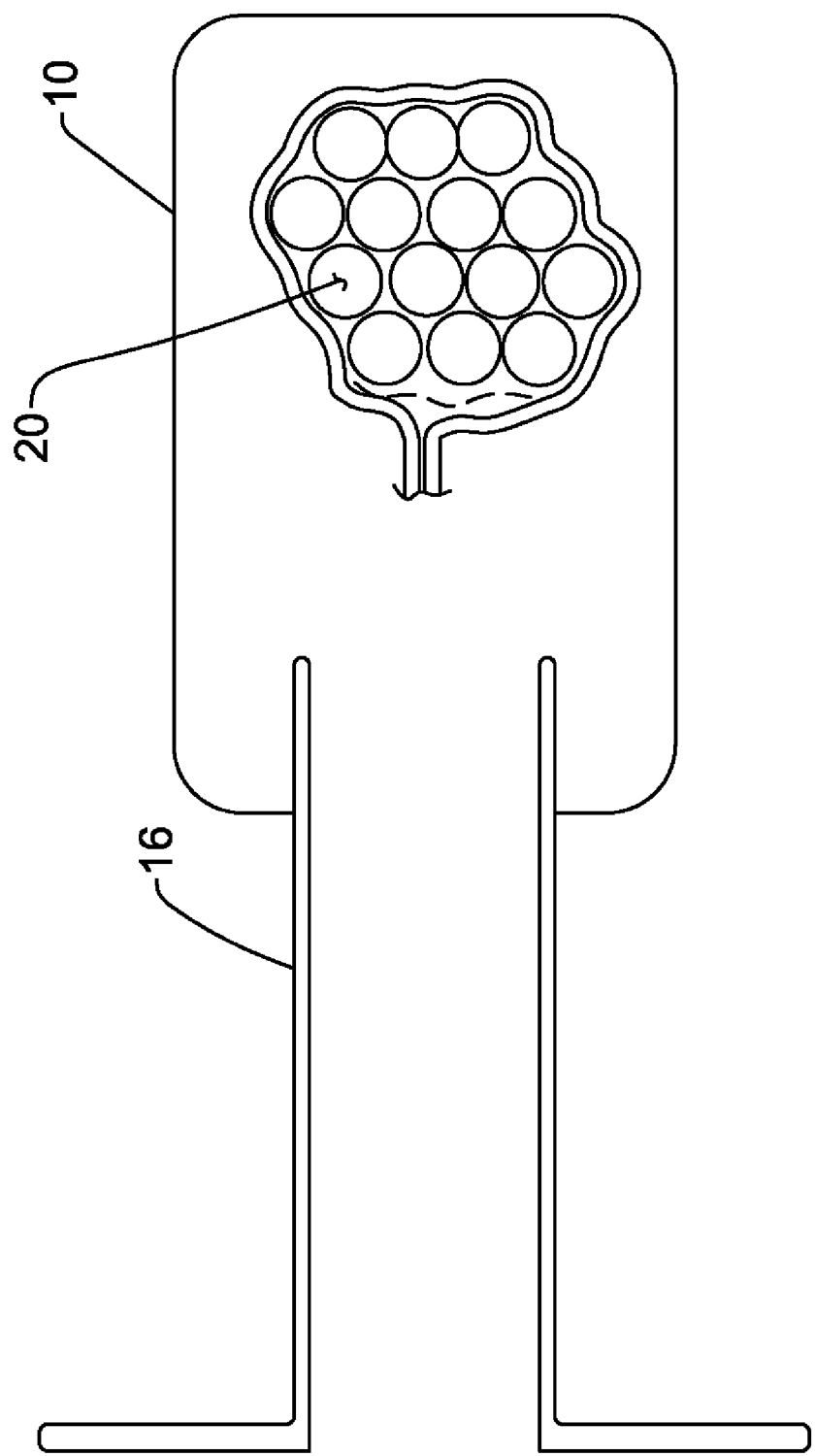

Cut-off tube 250 is advanced until it is relatively close proximity to the implant. The tube 250 may be at least momentarily held in this position so as to give the cement within the sock 242 immediately adjacent the tube opening 250 time to cure. The strand of compressed sock 242 proximal to the head may be twisted in order to close off the sock. In other versions of the invention a small heating element is fitted to the tube head 252 (not illustrated). Typically, this heating element is located on the face of the head 252 adjacent opening 254. This heating element is further positioned so as to be located around the perimeter of the opening opposite the beveled surface This heating element is actuated to seal the sock to itself. Once the sock is so sealed, the compressed strand proximal to the seal is forced against the beveled edge around tube opening 254. This edge thus serves as a knife edge that cuts the strand away from the implant, FIG. 33I.

The above assembly provides an alternative means for forming a contained implant within a bone.

In an alternative method of forming the above implant, once the cut-off tube is positioned adjacent the implant, a forceps-like tie off tool (not illustrated) is inserted in the cut-off tube. The tines of this tool have a distal located heating element and a proximal located cutting edge. When the tines of this tool are compressed together, the heating element closes the compressed portion of the sock immediately proximal to the tube head 252. At the same time the cutting edge serves the rest of the sock from the portion left behind as an implant.

XVI. Alternative Push Rod Drive Assembly

Figure 34:
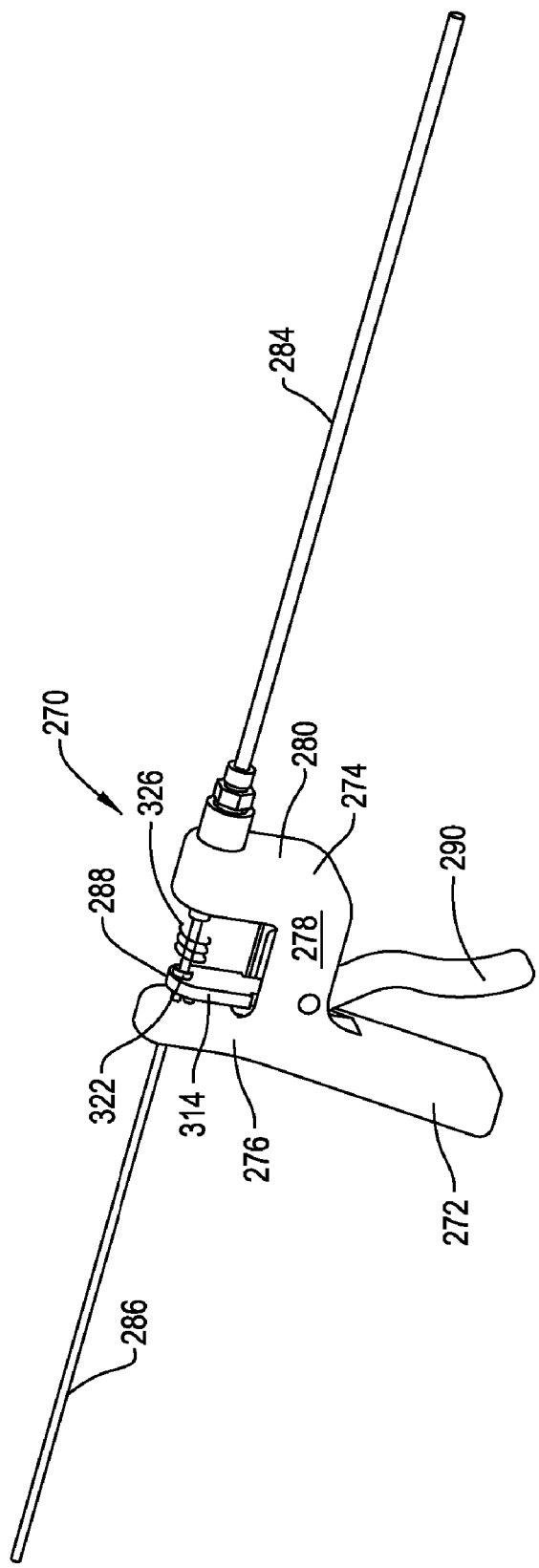
FIG. 34 is a perspective of an alternative assembly of this invention for delivering an agglomeration into the bone.
Figure 35:
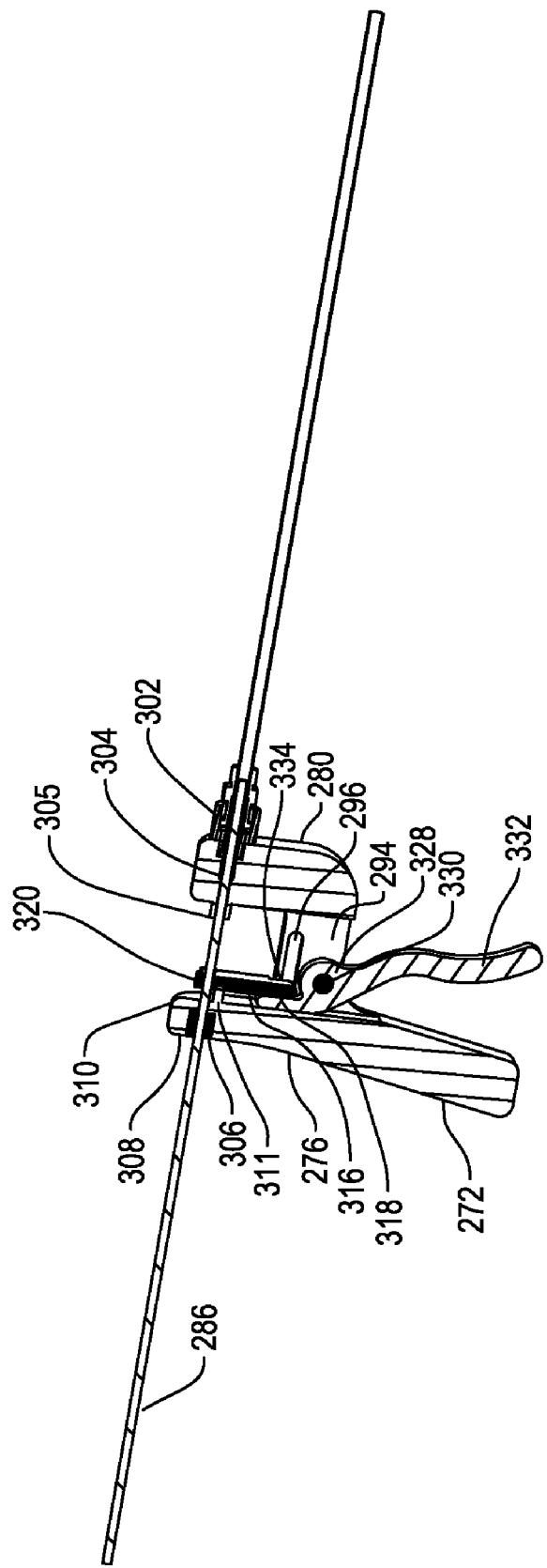
FIG. 35 is a cross sectional view of the assembly of FIG. 34.

FIGS. 34 and 35 illustrate an alternative push rod driver 270 of this invention. Push rod driver 270 as a gun shaped body such that there is a grip 272 from the top of which a barrel 274 forwardly extends. A delivery cannula 284 is releasably attached to the driver barrel 274. A push rod 286, for advancing the bead and cement agglomeration out of the cannula 284, enters the driver through the proximal rear end of the barrel 274. Push rod 286 is advanced forwardly, through the delivery cannula 284 by a pawl 288 slideably mounted to the barrel 274. The pawl 288 is manually advanced by a trigger 290 that is pivotally mounted to and extends downwardly from barrel 274

More specifically, driver 270 is formed so that barrel 274 is U-shaped such that it has two spaced apart parallel legs 276 and 280 separated by base 278. The more proximal of the two legs, leg 276, extends upwardly from the top of grip 272. The barrel base 278 extend generally perpendicularly distally away from the top of the grip 272. The distal most leg, leg 280 extends upwardly from the distal end of the barrel base 278.

The driver 270 is further formed so that barrel base 278 has two slots 294 and 296. Slot 294 extends top-to-bottom through the base 278. Thus in the center of barrel slot 294 defines a void space between the two legs 276 and 280. Slot 296 is an oval shaped, horizontally extending slot located in the side of the barrel base 278. Slot 296 intersects slot 294 a short distance below the top of the barrel base 296. In the illustrated version of the invention driver barrel 274 is shown such that slot 296 is formed on only one side of the barrel. In some versions of the invention, slot 296 extends completely through the barrel base 296.

A cylindrical head 302 is mounted to the top front face of the driver barrel leg 280 so as to extend distally forward. Concentric with head 302, barrel leg 280 is formed with a longitudinally extending bore 304. Bore 304 is dimensioned so that push rod 286 will slip fit therein. Head 280 has an inner diameter larger than the that of bore 304. The inner surface of head 302 is formed with threading (not illustrated). The threading, as described below, facilitates the releasable attachment of the delivery cannula 284.

Barrel leg 280 is also formed to have rearwardly facing circular flange 305. Flange 305 is centered around the proximal open end of bore 304.

A friction bushing 306 formed from rubber, is fitted in the proximal rear face of barrel leg 276. Bushing 306 is seated in bore 308 that extends forward from the rear face of leg. A bore 310 extends coaxial forward from the base of bore 308. Bore 310 is smaller in diameter than bore 308. More particularly, bore 310 has a diameter similar to that of front leg bore 304. The bushing 306 is formed with a bore 312. Bore 312 is sized so that when the push rod 286 is inserted therein, there is slight interference fit between the push rod and the bushing. Bushing 306 and bore 310 are located in leg 276 so as to be axially aligned with bore 304 internal to barrel leg 280.

Barrel leg 276 is further formed to have a forward extending pin 311. Pin 311 extends forward from the distally directed face of the leg 276 at a position below bore 310.

Pawl 288 is generally in the form of a plate with planar parallel front and rear faces, (not identified). The pawl 288 has a main section 314 with a side-to-side width approximately equal to the width of the barrel base 278. Below and integral with the main section 314, pawl 288 is shaped to have tab 316. Tab 316 has a width that allows the tab to fit and slidably move in barrel base slot 294. The pawl is held to the driver barrel by a pin 318 that extends through tab 316 along the lateral, side-to-side, perpendicular to, the axis of push rod 286. More particularly, pin is seated in the slot 296 formed in the barrel base 278.

The pawl 288 is shaped so that the main section 314 extends upwardly a slight distance above bores 304 and 310. Pawl main section 314 is formed with a bore 320 dimensioned to receive the push rod 286. More particularly, bore 320 has a diameter slightly greater than that of the push rod for reasons to be explained below. The pawl is formed so that that a circular flange 322 extends forward from the main section. Flange 322 is concentric with bore 320. The inner diameter of flange 322 is larger than the diameter of bore 320. Pawl 288 also has in the rear face thereof an opening 323. Opening 323 is dimensioned to receive barrel leg pin 311.

Not identified is a closed end bore that extends forward from the rear face of the pawl main section 314. When the pawl 288 is disposed adjacent the barrel rear leg 276, barrel pin 311 seats in this bore.

A helical spring 326 extends between barrel leg 280 and the pawl 288. The distal end of the spring 326 is disposed over leg flange 305. The proximal end of the spring 326 is disposed over pawl flange 322. Spring 326 normally urges the pawl 288 towards the barrel leg 276.

Trigger 290 advances pawl 288 forward. The trigger 290 includes a center hub 328 located in barrel base slot 294. Trigger center hub 328 is rotatably mounted in base slot 294 by a pin 330 that extends through the hub and the walls of the barrel base 278. An elongated finger grip 332 extends diagonally downwardly and forward from the center hub 328. Also part of trigger 290 is a lever arm 334. the lever arm 334 is integral with and extends upwardly from the center hub 328. Lever arm 334 is located between the proximal barrel leg 276 and pawl. The lever arm 334 is shaped to extend over the pawl tab 316 and the bottom of the pawl main section 314.

Figure 36:
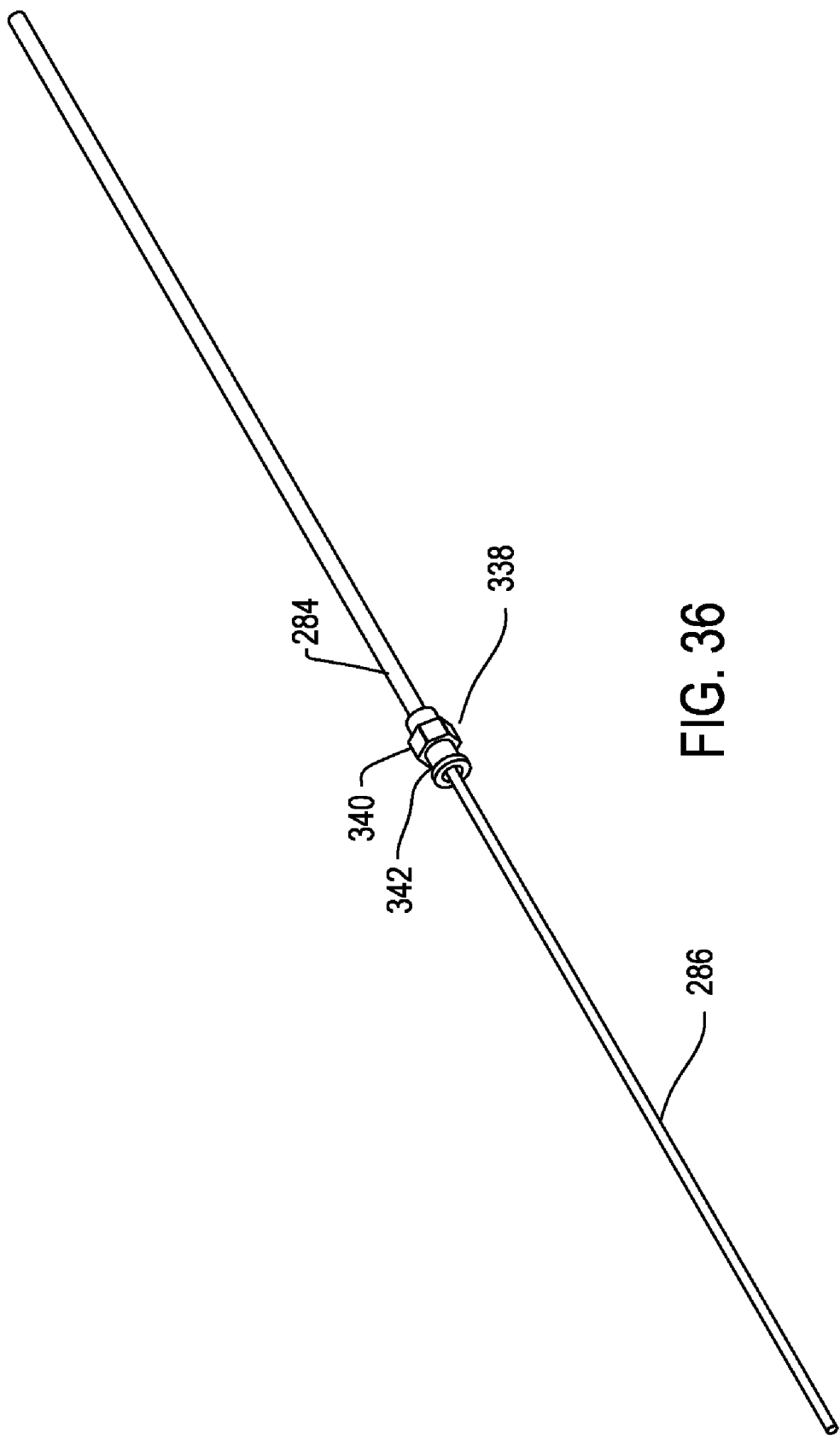
FIG. 36 is a perspective view of the delivery cannula and push rod of the assembly of FIG. 34.

FIG. 36 illustrated how in this version of the invention, a connector 338 is attached to the distal end of the delivery cannula 284. Connector 338 has a large diameter head 340. Extending proximally from the head 340, connector 338 has a tubular boss 342. Boss 342 is formed with threading to facilitate the screw securement of the cannula 284 to the head 302 integral with driver 270.

Driver 270 of this invention is used to advance push rod 286 through delivery cannula 284 in order to cause the discharge of the bead and cement agglomeration in the delivery cannula. The driver 270 is used by screw securing the delivery cannula 284, with the agglomeration already loaded, to the driver head 302. Push rod 286 is then coupled to the assembly. Specifically, the push rod is inserted through barrel bushing 306, barrel bore 310, pawl bore 320, the center of spring 326, barrel bore 304 and driver head 302 into the delivery cannula 284.

The push rod 286 is advanced by manually pivoting the trigger finger grip 332 towards the driver grip 272. The movement of the finger grip 332 results in the pivoting of the trigger lever arm 334 towards the distal end of the barrel 274, (the force applied by spring 326 is overcome.) This forward movement of the lever arm serves to cause a like movement of the pawl 288. As the pawl 288 pivots forward, tab 316 moves forward of the main section 314. This angular displacement of the pawl 288 traps the portion of the push rod 286 in the pawl bore 320. Consequently, the continued forward movement of the pawl causes the push rod to overcome the resistive force imposed by friction bushing 306. Thus, with the forward movement of the pawl 288, the push rod 286 engages in a like advancement into delivery cannula 284. The push rod thus provides the mechanical force that urges the bead and cement agglomeration in the delivery cannula into the adjacent bone.

Upon release of the trigger finger grip 332, spring 326 is able to push the pawl 288 back to its static state. As the pawl moves rearwardly, friction bushing 306 imposes a resistance on the push rod 286. This resistance is sufficient to prevent rearward force the pawl 288 may impose of the push rod 286 from moving the rod rearwardly.

Driver 270 of this invention is assembled that the exposed section of push rod subjected to forward loading, the section between the pawl 288 and the distal barrel leg 280, is relatively short in length, typically 10 cm or less and, more preferably, 5 cm or less. Thus in the event, this section of the push rod is subjected to an appreciable amount of force as it is advanced into the delivery cannula, it will likely result in the rod advancing into the cannula before it causes the rod to bend. Therefore, the driver of this invention is designed to minimize the likelihood that the push rod used to advance the bead and cement agglomeration will bend during its advancement into the delivery cannula 284. Thus, when delivery forces are high, the use of assembly 240 minimizes the likelihood of push rod buckling.

Still another feature of this driver is that push rod is a separate component from the driver itself and is easily attachable to the driver and delivery cannula. Thus, after the single of the push rod, where it becomes in contact with the beads and cement forming the agglomeration, the push rod can be advanced forward for discharge from the rest of the assembly and disposal. This forward advancement of the push rod substantially eliminates the possibility that the drive itself will be coated in the cement covering the push rod. There is no need to engage in the costly process of sterilizing this component or removing cement. Since a new push rod can easily be coupled to the driver, this component can be replaced for use in a subsequent procedure.

XVII. Second Alternative Push Rod Drive Assembly

Figure 37:
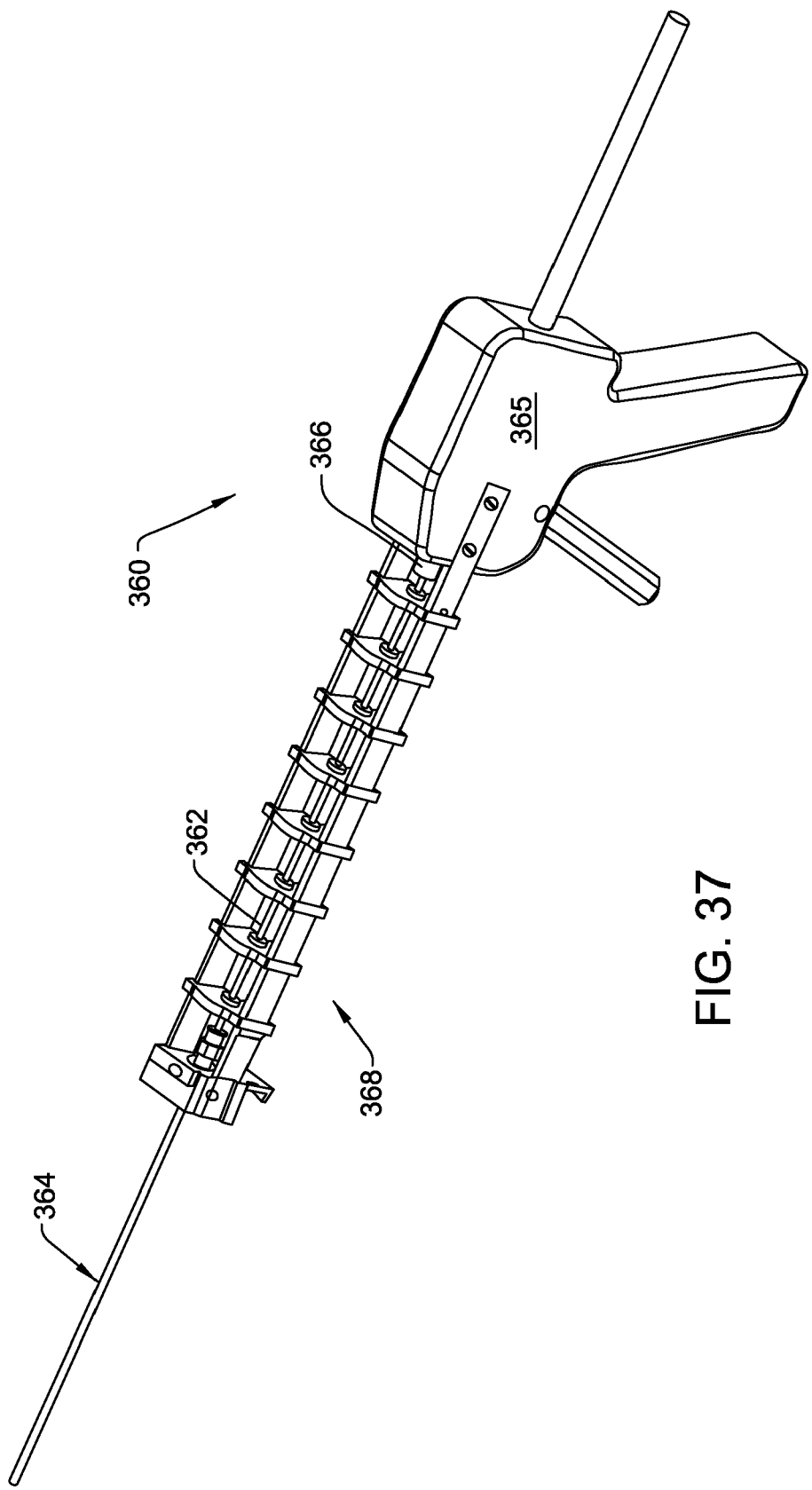
FIG. 37 is a perspective view of an alternative agglomeration delivery assembly of this invention, the assembly having an anti-buckling assembly to reduce the instance of push rod bending.

FIG. 37 illustrates another alternative driver 360 of this invention for advancing a push rod 242 into a delivery cannula 364. Driver 360 includes a drive gun 365. Drive gun 365 advances a ram 366 forward against the proximal end of the push rod 242. The push rod 242 is slidably mounted in an elongated anti-buckling assembly 368. The drive cannula 364 extends forward from the distal end of the anti-buckling assembly 384.

Drive gun 365 is an assembly for imposing a forward force on ram 366. Delivery assembly 26, described with respect to FIG. 20, can function as the drive gun. In this version of the invention however, the delivery assembly does not directly apply forward motion to the push rod. Instead, the delivery assembly advances the cylindrical ram 366. The front face of the ram 366 abuts the proximal end of the pus rod. To deliver the bead and cement agglomeration to the bone so that it can compress the cancellous tissue in order to form the implant it has been known to require forces in excess of 200 pounds. Therefore, drive gun 365 should be selected so that it can apply forces in this range.

Figure 38:
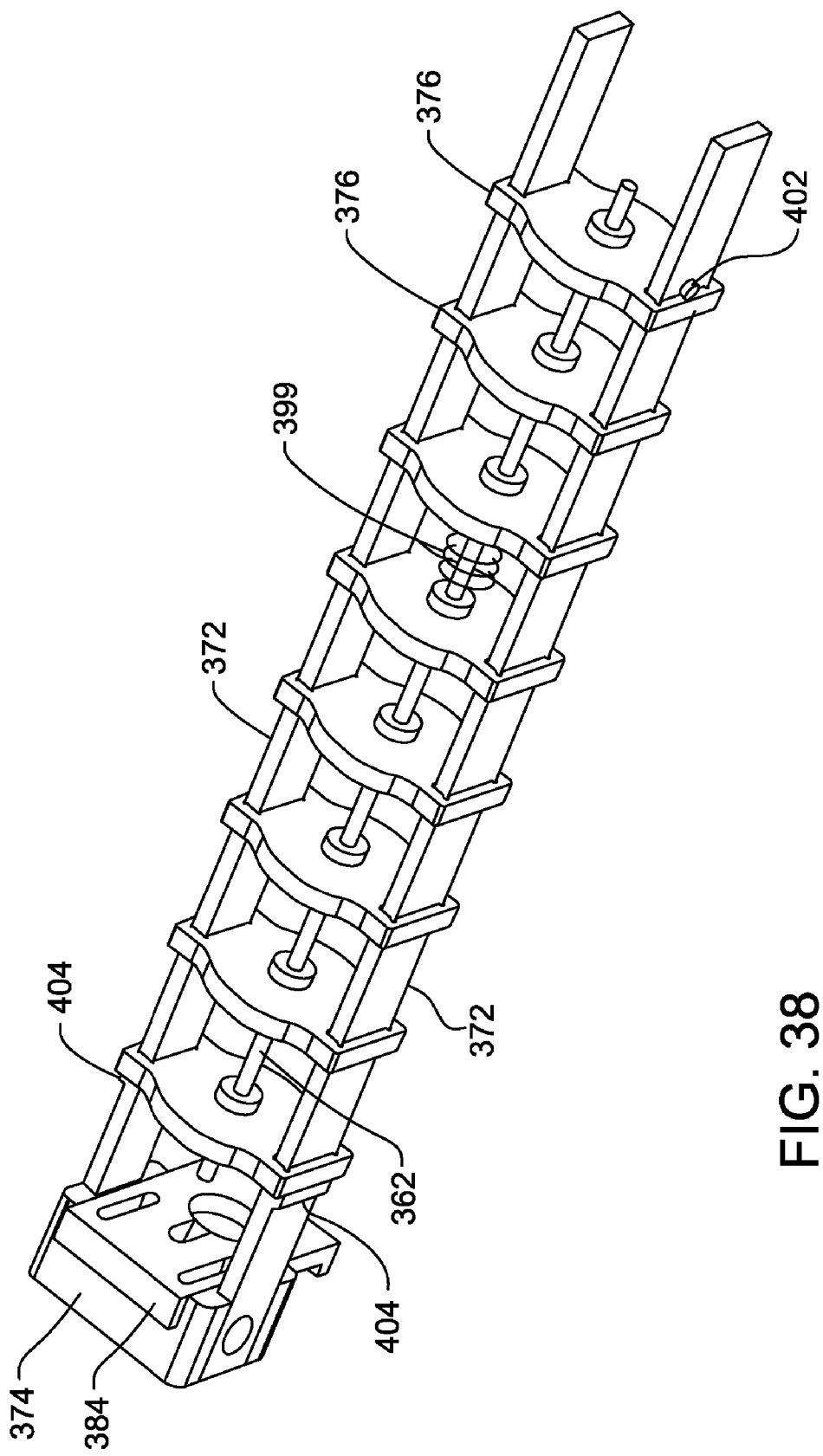
FIG. 38 is a perspective view of the anti-buckling assembly of the delivery assembly of FIG. 36 wherein the guide plates are in the expanded position.
Figure 39:
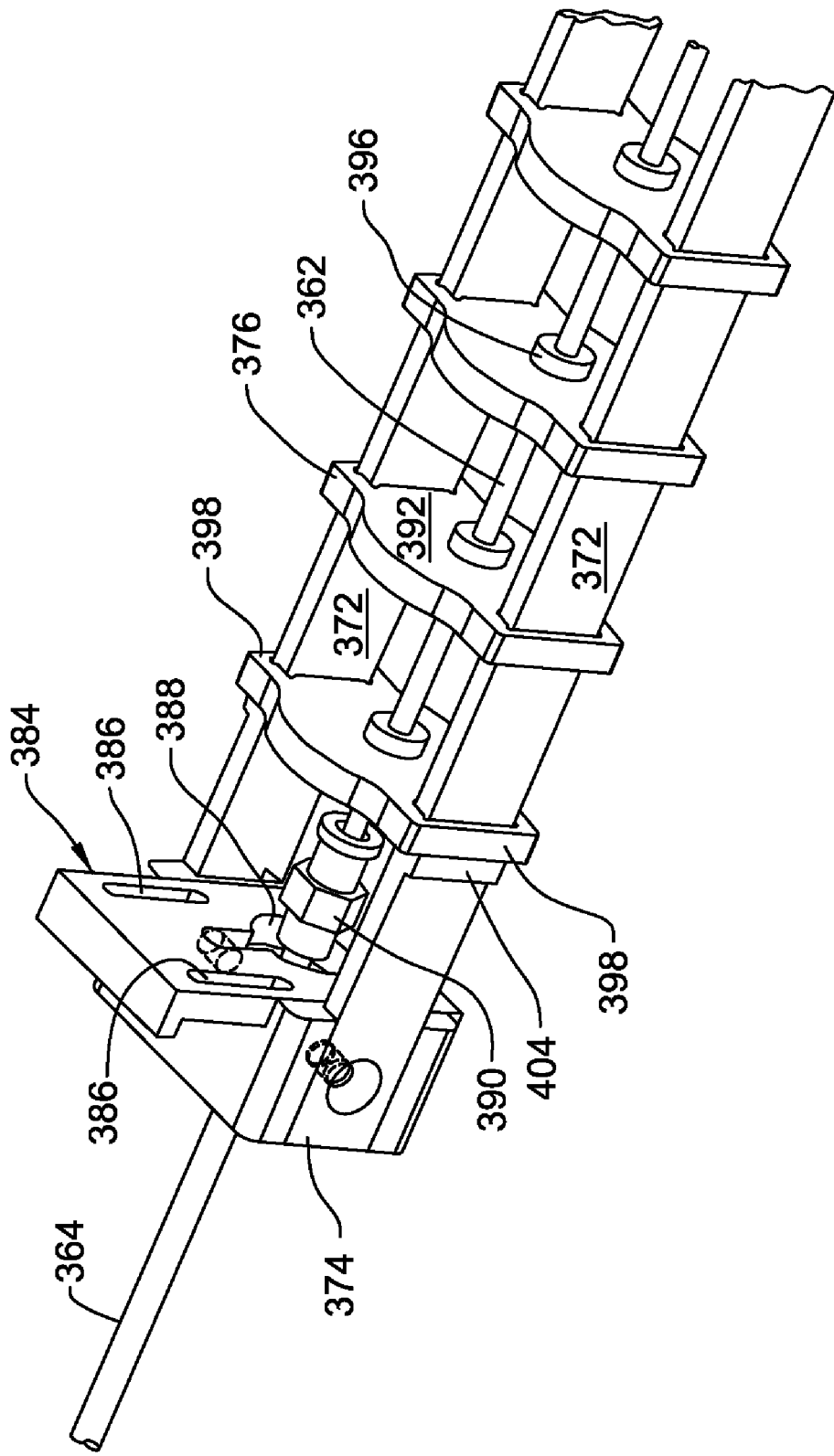
FIG. 39 is an enlarged perspective view of the distal end of the anti-buckling assembly of FIG. 38.

The anti-buckling assembly 368, seen best in FIGS. 38 and 39, is mounted to and extends forward from the drive gun 365. The anti-buckling assembly includes two elongated parallel guide rails 372. The proximal ends of the guide rails 372 are mounted to the outer body of the drive gun 364 so as to extend forward from the gun. A head 374 is extends between and is secured to the front ends of the guide rails 372. The anti buckling assembly also has a number of parallel guide plates 376. The guide plates 376 are slidably mounted to the guide rails 372. Each guide plates 376 is formed with a center located opening 378. The push rod 242 extends slidably extends through the guide plate openings 378.

As seen in FIGS. 37 and 38, head 374 is in the form of a rectangular block. Fasteners, (not illustrated) secure the head 374 to the opposed inner surfaces of the guide rails 372. Head 374 is formed with a center through bore 382, seen in phantom in FIG. 40, that is axially aligned with guide plate openings 378. Bore 382 is dimensioned to allow the delivery cannula hub 390 to extend therethrough.

Attached to the head 374 is an assembly for releasably holding the delivery cannula 364 to the anti-buckling assembly 368. In the illustrated version a gate 384 performs this function. Gate 384 is in the form of a rectangular plate that is slidably mounted to the rearwardly directed face of head 374. In the Figures, gate 384 is shown to have on the opposed sides thereof opposed parallel oval shaped slots 386. Slots 386 extend partially along the top-to-bottom length of the gate. Not illustrated are the posts with heads attached to the head that extend through the slots 386. The posts are the components that slidably hold the gate 384 to the head so that the gate can be moved up and down as described below.

The gate 384 is formed with a keyhole-shaped opening 388. The longitudinal axis of gate opening 384 intersects the axis of head bore 382.

The delivery cannula 364 is attached to driver 360 by sliding gate 384 so that the large diameter section of keyhole opening 388 is in registration with head bore 382. The proximal end of the delivery cannula 364 is passed through both the head bore 382 and the keyhole opening 388. More particularly a large diameter head 390 is mounted to the proximal end of the cannula 364. Head 390 and adjacent portion of the narrow diameter body of the cannula are the portions of the cannula that are inserted through head bore 382 and the keyhole opening 388. Once the cannula 364 is so positioned, gate 384 is slid downwardly. This action results in the portion of the gate around the narrow diameter section of the gate keyhole opening 388 extending of the narrow diameter portion of the cannula immediately adjacent the head 390. As long as the gate 384 remains in this position, forward movement of the delivery cannula 364 is blocked.

Each guide plate 376 is shaped to have an approximately circularly shaped head 392. Openings 378 extend through the centers of the guide plate heads 392. Each guide plate 376 is further formed so that on the distally directed side, head 392 is formed with a circular recess 394, seen in phantom in FIG. 40. Each recess 394 subtends the majority of the surface area of the guide plate head face with which it is associated. The opposed, proximally directed sides of the guide plates are provided with cylindrical bosses 396. Each guide plate 376 has a single boss 396. Each boss 396 is centered around the center axis of the guide plate head 392 from which the boss extends. The opening 378 formed in the head 392 extends through the associated boss 396.

A pair of ears 398 extend outwardly from the head 392 of each guide plate 376. The ears 398 extend from the opposed sides of the head 392 with which they are integral. Each ear 398 is generally rectangularly shaped. Ears 398 are generally coplanar with the guide plate head 392. Each ear 398 has a rectangular opening (not identified).

Figure 40:
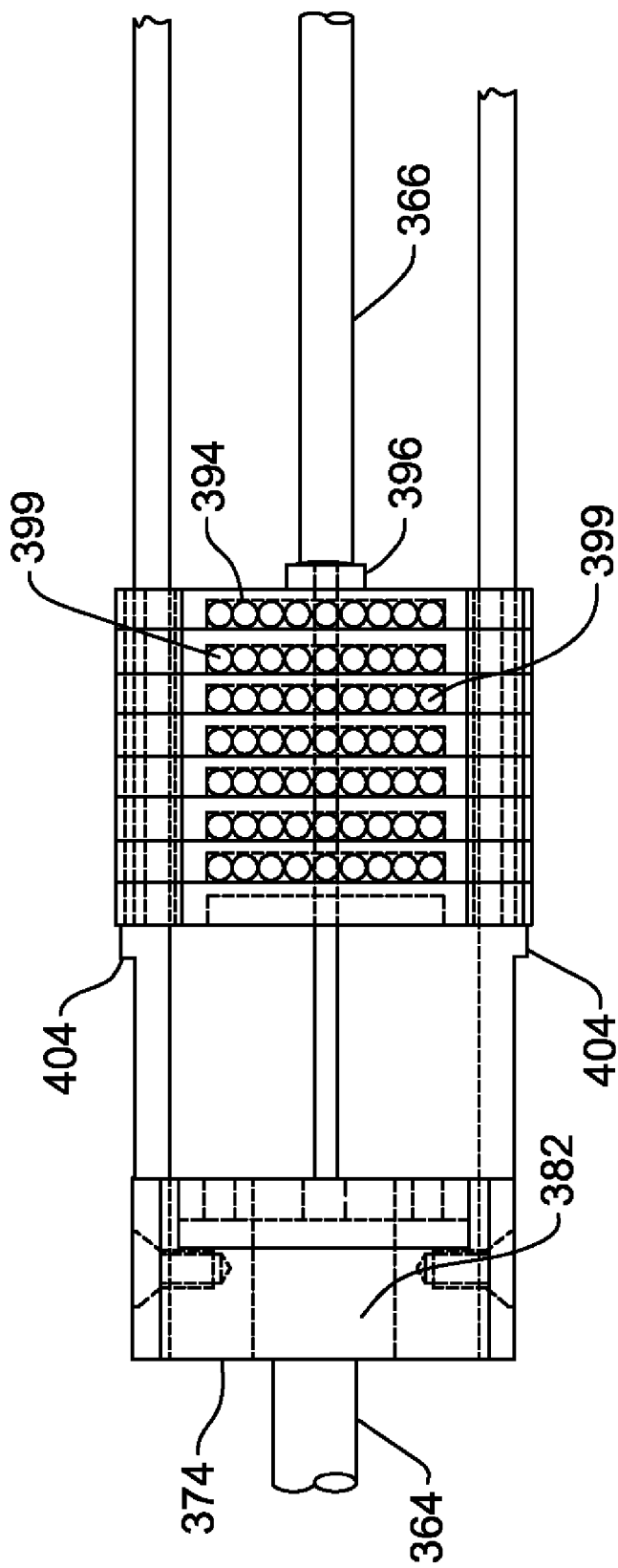
FIG. 40 is a top view of the anti-buckling assembly of FIG. 38 wherein the guide plates are in their forward, compressed position.

A conical compression spring 399 extends between each guide plate 376 (One spring 399 shown expanded in FIG. 38 a number of compressed springs 399 shown in phantom in FIG. 40). Springs 398 are arranged so that their wide diameter ends are proximally directed. Each spring 399 is positioned so that the proximally facing wide end of the spring is seated in the recess 394 of a first one of the guide plates 376. The opposed distally directed narrow end of the spring 399 is seated over the boss 396 of an adjacent second plate 376.

Plate stops 402 and 404 integral with guide rails 372 limit longitudinal movement of the guide plates 376. The plate stops 402 and 404 extend outwardly from the side surfaces of the guide rails 376 so as to abut the ears 398 integral with the adjacent guide plate 376. Each guide rail has a guide stop 402 and a guide stop 404. Guide stops 402 are located forward of the proximal end of the guide rails 372. Stops 402 thus limit rearward movement of the most distal of the guide plates 376. Stops 404 are located rearward of the assembly head 374. In some versions of the invention stops 402 are pins that are press fit into rails 376. Stops 404 thus limit forward movement of the most forward of the guide plates 376. In the illustrated version of the invention guide stops 402 are in the form of cylindrical heads. Stops 404 are in the from of bars that extend laterally across the outer surfaces of the associated guide rails 376. Both shapes are exemplarily, not limiting.

Guide stops 402 and 404 do more than limit movement of the guide plates 376. Stops 402 and 404 are spaced apart from each other a select distance so that springs 398 place a small pre-load force on each of the guide plates 376. As a result of this pre-loading and the selection of the springs 398, the guide plates 376 are generally spaced apart a common distance from each other.

One step in preparing driver 360 for use is the mounting of the delivery cannula to the anti-buckling assembly head 374. The ram 366 is fully retracted, in its proximal most position. The guide plates 376 may be compressed together to provide a space in which the push rod 242 can be coupled to the driver 360. When the guide plates 376 are so displaced, the inner turns of the springs 398 seat in the guide plate recesses already occupied by their outer turns. The push rod 242 is then passed through the guide plate openings 378.

Once the push rod 242 is so positioned, the guide plates 376 are released. Springs 398 return the guide plates 376 to their static locations. In many versions of the invention, the maximum spacing of the guide plates 376 when fully spaced apart from each other is 4 cm or less between adjacent plates.

Drive gun 365 is then actuated to move ram 366 forward. Initially, the ram 366 strikes the proximal end of the push rod so as to cause a like displacement of the rod. The push rod enters the delivery cannula 364 to force the bead and cement agglomeration outwardly, into the bone in which the implant is to be formed.

Ram 366 has an outer diameter greater than that of the push rod 242. Thus, eventually the ram abuts more than the proximal end of the push rod. The ram start to abut the outer surface of the boss 396 integral with the most proximal guide plate 376. The continued movement forward movement of the ram results in the like movement of the proximal guide plate. Eventually, as seen in FIG. 40, the distal end of the ram 366 strikes the proximal most guide plate boss 366. The continued action of the ram 366 results in this guide plate 376 likewise being pushed forward. The motion of this guide plate 376 is, through springs 398, transferred sequentially through to the most forward guide plate. Consequently, the displacement of the most rearwardly located guide plate results in a proportional displacement of all but the most distal of the guide plates.

Driver 360 is able to deliver 200 pounds or more of force. The push rods are of relatively thin diameter, diameter of 3 mm or less. However, as discussed above, the guide plates 372 are generally no more than 4 cm apart from each other. This spacing prevents the push rods 376, when subjected to high forces, from buckling or otherwise bending. It should further be appreciated that as the driver ram advances 366, the guide plates engage in a like forward advancement. Thus, the anti-buckling assembly of the driver of this invention, while minimizing the likelihood of push rod bending, does not inhibit the advancement of the push rods.

Moreover, both the push rod 242 and the delivery cannula 364 are removably attachable to the driver 360 of this invention. There is no requirement to use supplemental fasteners to attach either of these components to the driver 360. Therefore, the push rod and delivery cannula can both be provided as use-once items and the driver provided as a reusable device.

Also, a combined delivery cannula with push road contained there can be mounted to the front end of the anti-buckling assembly 368.

XVIII. Alternative Bead Assemblies

FIG. 41 illustrates an alternative bead 420 of this invention. Bead 420 has an elongated body 422. In the illustrated version of the invention, the ends of the bead body 422 are curved. In alternative versions of the invention, the ends of the body 422 have a flat profile.

Bead 420 is further formed to have three (3) fins 424 that are integrally formed with and extend radially outwardly from the body 422. Specific, the fins 424 lie on planes that project radially from the center longitudinal axis of the body 422. Fins 424 are equangularly spaced apart from each other.

As seen by reference to the cross section view of FIG. 42, when the beads 420 are loaded in the delivery cannula 18, the fins 424 suspend the bead body 422 so that body is spaced inwardly from the inner wall of the cannula 18. In the methods of this invention wherein the cement 22 is loaded into the cannula after the beads 422, the above arrangement ensures that there are spaces between the cannula inner wall and the bead bodies 422 through which the cement can flow.

The above described flow paths are provided even if the cannula inner wall has a completely circular cross sectional profile. Thus, the beads of this invention eliminate the need to provide the cannula with more costly structural features that are most costly to provide, such as stand off ribs, to ensure there are flow paths to facilitate mixing of the cement with the beads.

FIGS. 43 and 44 illustrate a bead 430 having still another alternative shape. Bead 430 has a body 432 that is generally cylindrical. However, bead body 432 is further formed to have opposed end surfaces 434 with flat faces that are parallel to each other. Bead 430 is further shaped so to have coplanar fins 436. Fins 436 are in a plane that is perpendicular to and extends between the planes along which end surfaces 434 lie.

Bead 430 may be injected into a bone through a cannula 440 as illustrated in FIGS. 43 and 45. Cannula 440 is shaped so as to have along the inner surface thereof opposed grooves 442. When the beads 430 are loaded in cannula 440, the opposed fins 436 seat in the opposed grooves 442. Fins 436 thus prevent side-to-side movement of the beads. Accordingly if the cannula inner diameter is larger than the maximum diameter of the bead body 432 this arrangement ensures that on the sides of the beads body 432, between the fins 436 there will be space through which cement can flow.

The flat end surfaces 434 ensure that when the beads abut they abut flat-to-flat as seen in FIG. 45. Thus should the cannula 440 be constructed so as to have top-to-bottom height that is greater than the diameter of the bead body 432, one bead will not wedge under or below an adjacent bead. Such wedging if allowed to occur, while the agglomeration is under pressure, could inhibit downline advancement of the beads and cement entrained therewith. Instead the flat-too-flat abutment of the beads 430 ensures that each bead transfers the longitudinal distal force applied to it to the immediately proximally adjacent bead.

Figure 46:
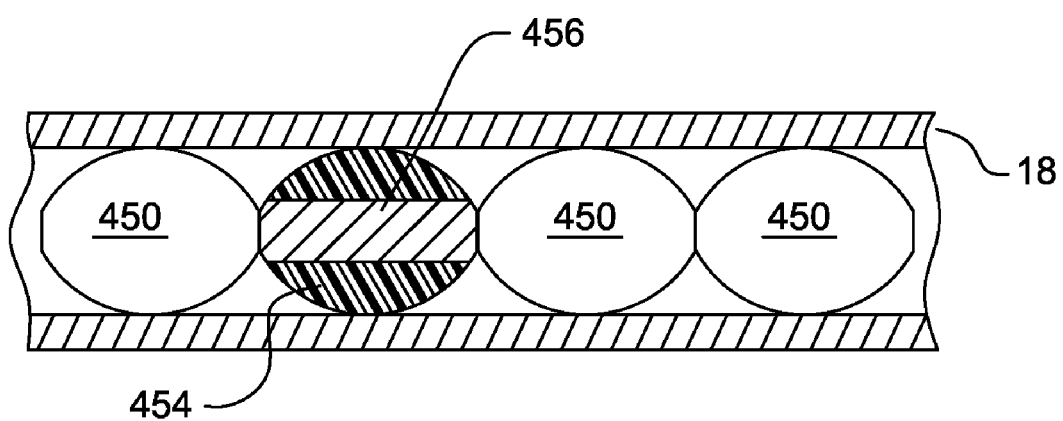
FIG. 46 is a longitudinal partial cross sectional view of an array of another type of alternative beads of this invention disposed in a cannula.

Another alternative bead 450 that can be used to form the bead and cement agglomeration is now described by reference to FIG. 46. Here a linear array of beads 450 are shown disposed in a delivery cannula 18 surrounded by cement 22. As seen by the bead 450 shown in cross section, each bead 450 includes a core 452 formed from metal. Often the core 452 is in the form of a cylinder with parallel ends that are perpendicular to the longitudinal axis of the core. The core 452 is encased in a shell 454 also part of the bead 450. The shell 454 is formed from plastic. In the illustrated in FIG. 46, shell 46 has an oval cross-sectional profile. The shell 454 is, however, formed with an opening 458 in which the bead core 452 is seated.

The components forming bead 450 perform different functions. When the beads 450 are loaded into the cannula to form the agglomeration, the oval profile of the shells 454 causes the beads to line up core end-to-core end. Consequently, when pressure is applied to the beads to discharge the agglomeration from the cannula, the longitudinal moment is transferred from metal core-tom-metal core to the most distal bead 450. Then when the pressure pushes the beads against the surface of the surrounding bone, since the cores are only subjected to minimal deformation, the force applied to the beads is applied through the cores to the bone. This force is able to compact the tissue in order to form a space in which the implant can form.

When the cement around the beads 450 to form the implant, the cement primarily adheres to the surface of the shell 454. In relative relationships, the modulus of deformation of the plastic forming the shell 454 is closer to the modulus of deformation of the hardened cement than the module of deformation of the metal core 452. Thus, when the implant is exposed to the loading forces, the forces to which bone is normally exposed, the deformation of the bead shells 454 will be relatively close to the deformation of the cement. The closeness of these deformations minimizes the extent that the bead 430 will delaminate from the cement so as to cause the components forming the implant to separate.

Figure 47:
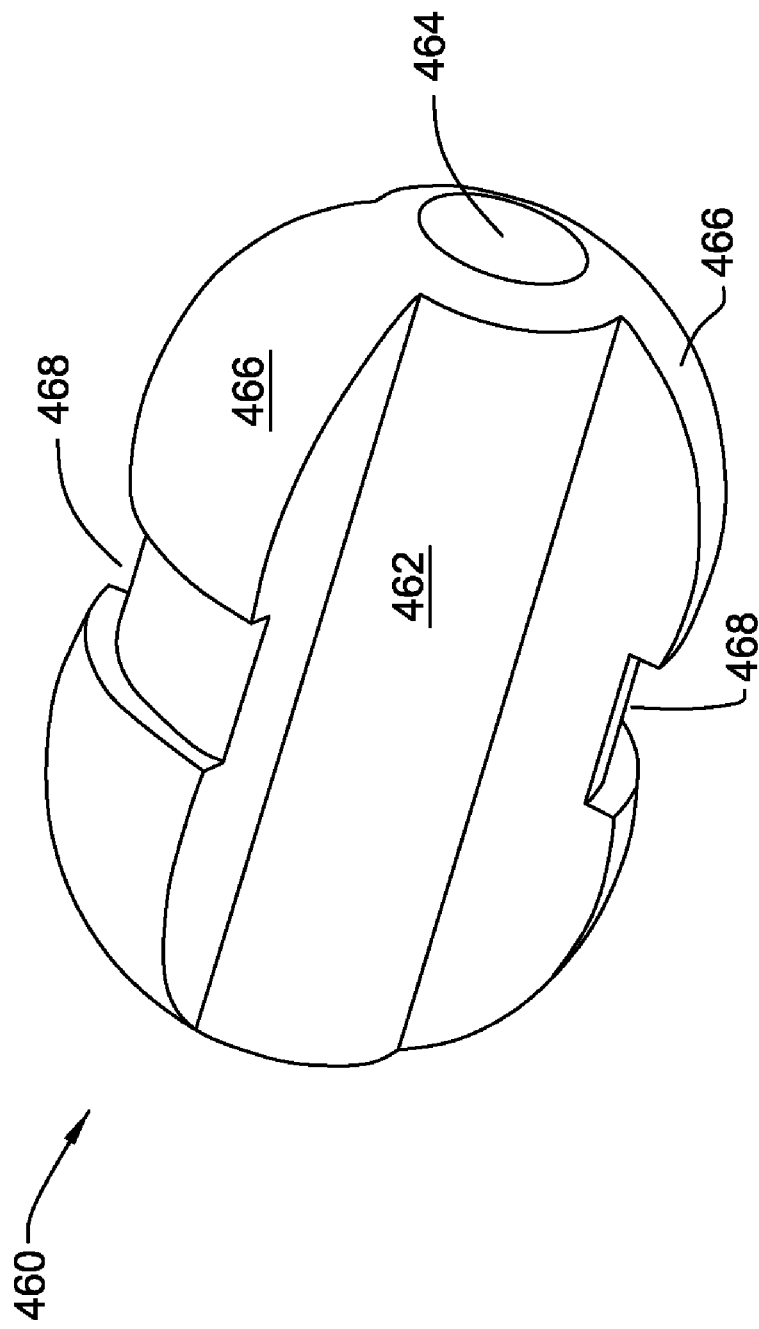
FIG. 47 is a perspective view of an alternative bead of this invention.

It should be understood that the shells of the beads of this version of the invention may have alternative shapes. One alternative shell 460 is now described by reference to FIG. 47. Shell 460 is shaped to have a center tube-shaped column 462. Column 462 is formed with a center located axially extending through bore 464 for receiving a core. Radiating outwardly from column 462, shell 460 has a number of arcuately spaced-apart fins 466. Each fin 466 is generally symmetrical around the lateral axis. Thus, each end of fin 466 has an outwardly curved face (not identified). Each fin is further formed so as to have in center section thereof a laterally extending groove 468. In the illustrated version of the invention, groove 468 has a rectangular cross sectional profile.

When the beads including shell 460 are loaded in the delivery cannula 18, the elongated shape of the shells ensures that the beads line up core end-to-core end. When the cement is applied to the beads to form the agglomeration, the cement fills both the fin grooves 468 and the angular void spaces between the fins 466. Thus, when these beads are discharged from the cannula, the carry with them a sufficient amount of cement to form the implant.

Figure 48A:
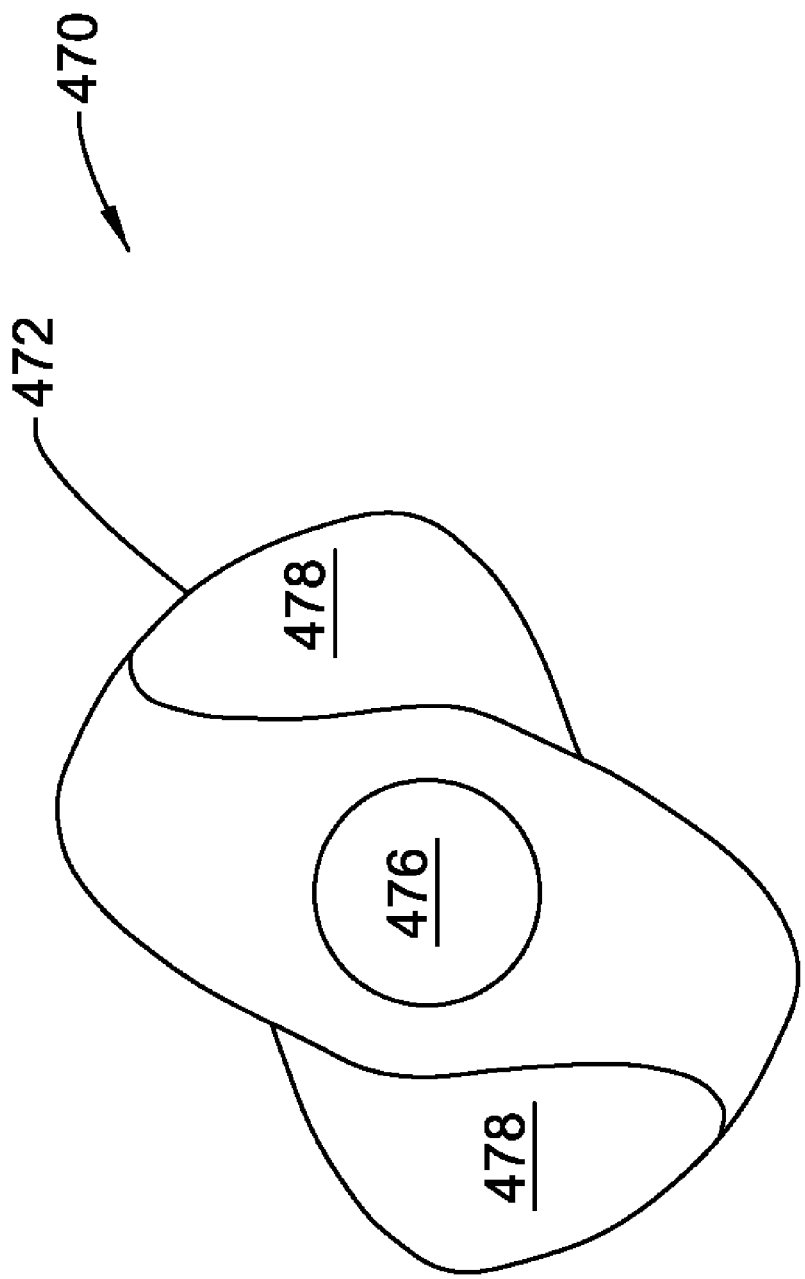
FIGS. 48A and 48B are respectively, front and perspective views of another alternative bead of this invention.
Figure 48B:
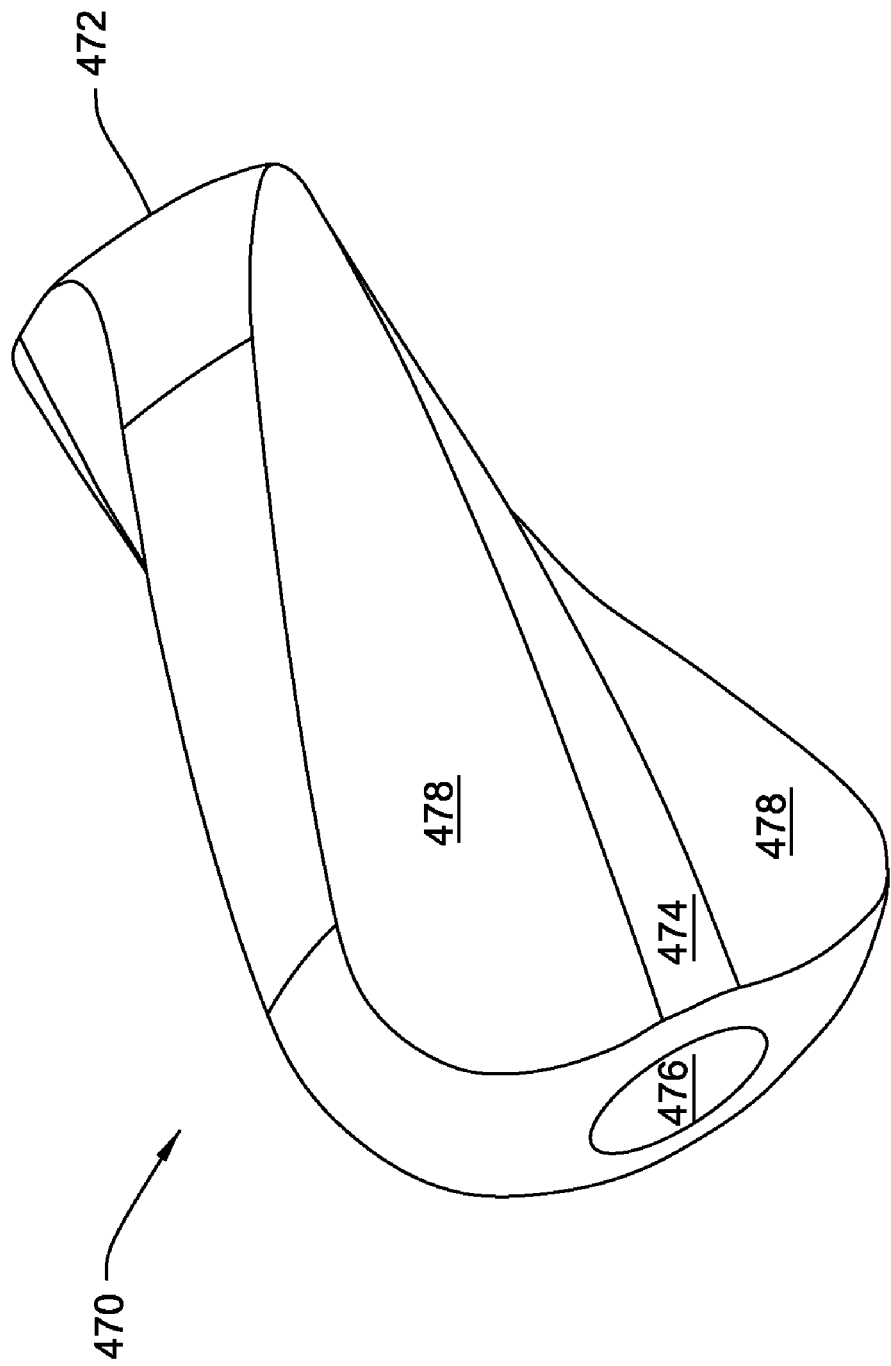

FIGS. 48A and 48B illustrate another alternative bead 470 of this invention used to form the bead and cement agglomeration. Bead 470 has a plastic shell 472 with a tubular center column 474. Column 474 is formed with an opening (not identified) for receiving the metal core 476. Two wings 478 project symmetrically and radially away opposed sides of column 474. Shell 472 is formed so that wings 478 have a curved profile along the length of the bead 470. In other words, the axis extending laterally between the wings, the axis perpendicular to the longitudinal axis of the bead 470, rotates along the length of the bead. In the illustrated version of bead 470, from one end of the bead to the other, this axis rotates through an arc of approximately 90°. The shell 472 of bead 470 is further formed so that that the corners adjacent the opposed ends of the bead are curved.

When the beads 470 of this invention are loaded in the delivery cannula 18, they align metal core-to-metal core. When cement is introduced into the cannula 18 to form the bead and cement agglomeration, the pressure head of the cement acting against the surfaces of the opposed wings 476 can cause the bead to rotate. More particularly, the bead will rotate until the pressure head of the cement is able to flow over the bead and onto the next bead.

During the process of delivering the bead and cement agglomeration, the force on the bead cores 476 forces the beads out of the tubes. The cement is likewise discharged owing to the fact this is adhering to the surfaces of the shell wings 478.

Figure 49:
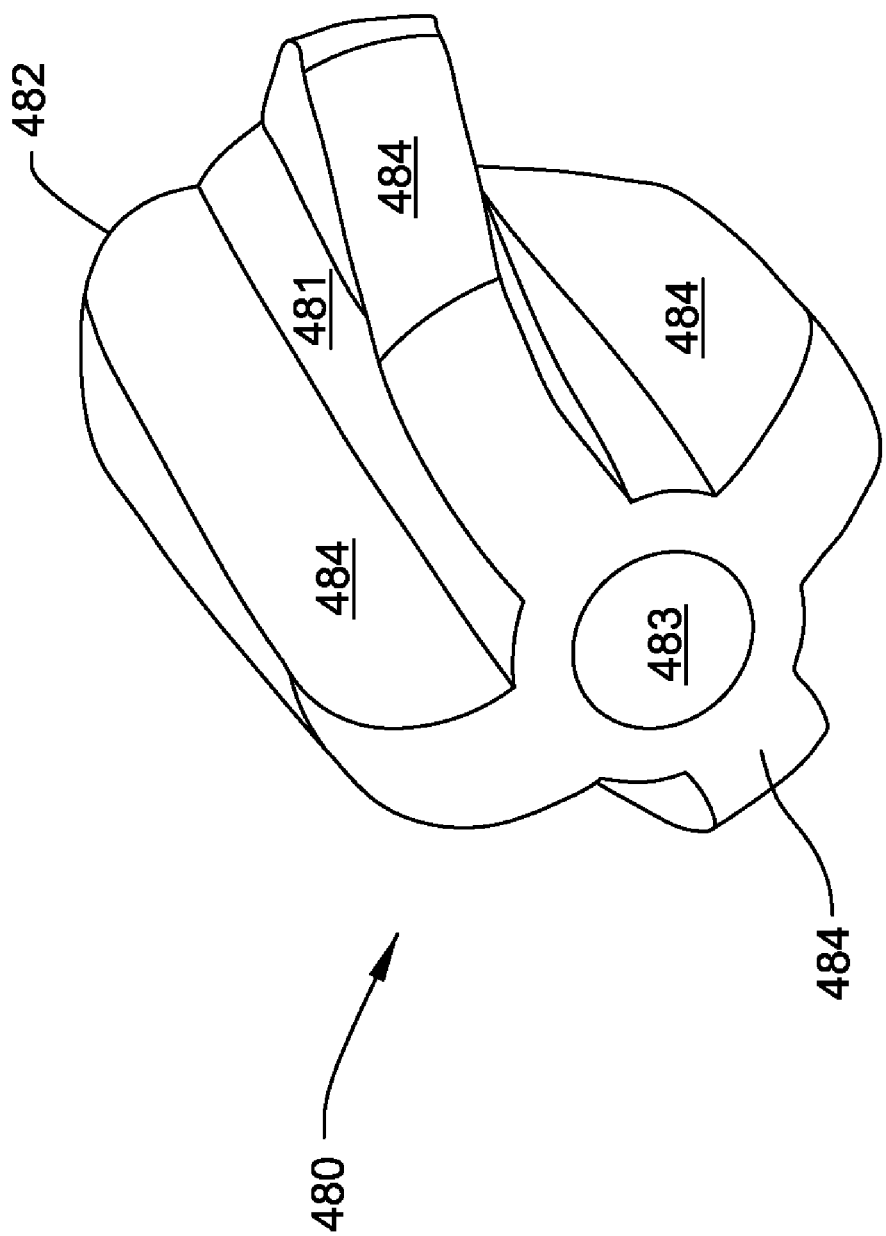
FIG. 49 is a perspective view of another alternative bead of this invention.
Figure 50:
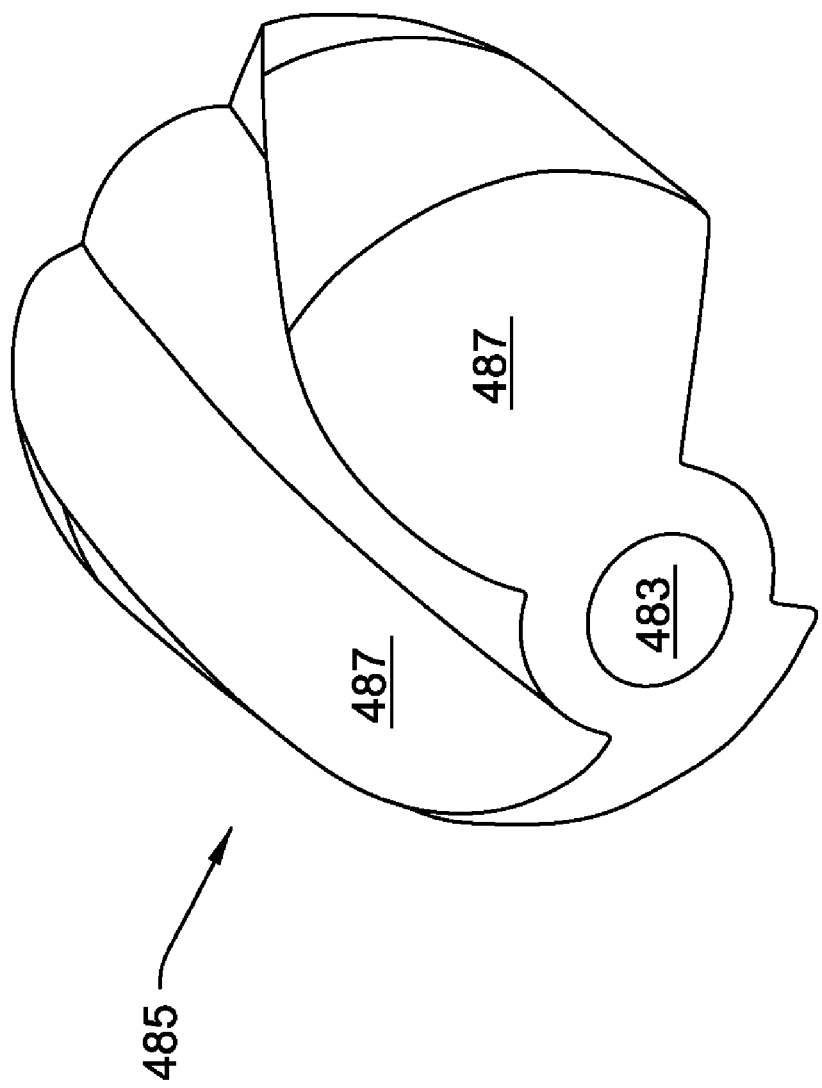
FIG. 50 is a perspective view of another alternative bead of this invention.

FIG. 49 illustrates an alternative bead 480. Bead 480 is formed with a shell 482. Shell 482 has a center-liked, tube-like column 481 in which core 483 is disposed. Four equangularly spaced apart wings 484. Shell 484 is shaped so that the curvature of any individual wing 484 between the opposed ends of the bead is approximately 45°. FIG. 50 illustrates an alternative bead 485. Bead 485 has a shell 486 with column 487 similar to column 581 of bead 480. A core 483 is disposed in column 487. Two symmetric wings 488 extend radially outwardly from column 487. Shell 486 is similar in basic shape to shell 472. A difference between the two shells is that wings 488 extend angularly outwardly from the sections of the column 487 from which they project. Thus, the outer perimeters of wings 488 subtend a larger arc than their inner perimeters.

XIX. Fourth Alternative Delivery Handpiece

Figure 51:
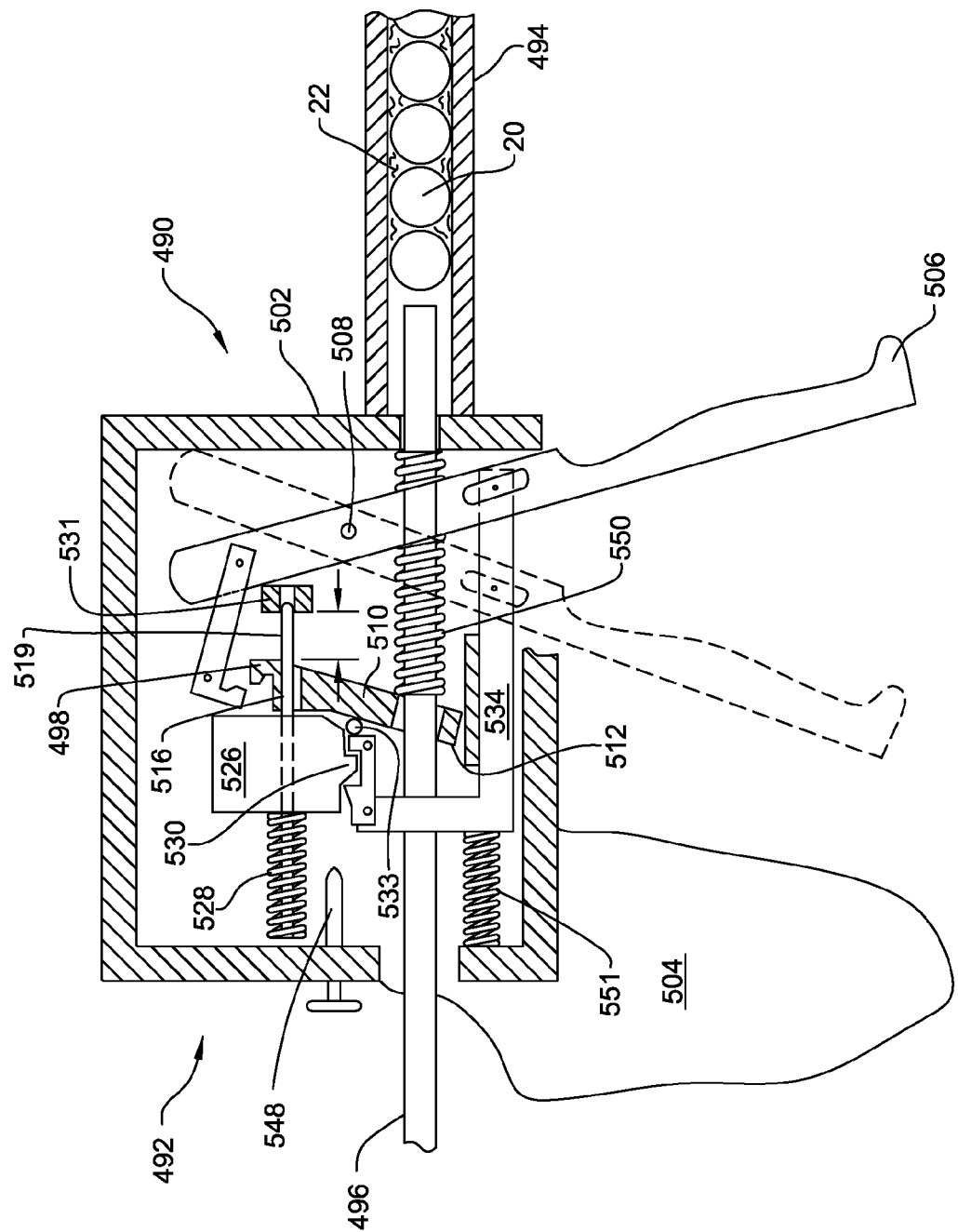
FIG. 51 is a side cross sectional view of an alternative delivery assembly of this invention for advancing a push rod into the delivery cannula.

FIG. 51 illustrates a handpiece 490 capable of applying one of two different types of force to the bead and cement agglomeration in order to force the agglomeration into the bone. Handpiece 490 includes a gun shaped body 492 from which a delivery cannula 494 extends. A push rod 496 enters the body 492 through the proximal rear end of the body. Internal to the body is a drive pawl 498. Drive pawl 498 extends over the push rod 496 and is shaped to engage and advance the push rod into the delivery cannula 494. As described below, one of two components selectively advance the drive pawl 498.

Handpiece body 492 is shown to have a barrel 502 diagrammatically depicted as a rectangular structure. A handgrip 504 is formed integrally with and extends downwardly from the rear proximal end of the barrel. A trigger 506, illustrated as an elongated bar, is mounted to the barrel 502 so as to be located forward of the handgrip 504. The trigger 506 has an exposed section that extends out of the barrel and is the part visibly in front of the handgrip 504. The trigger also has a concealed section located inside the barrel 502. A pivot pin 508 pivotally connects the concealed section of the trigger to at least one of the side walls of the barrel 502. In FIG. 51, the trigger is shown in solid in its normal at rest position. The trigger is also shown in phantom in the retracted, actuated position when adjacent the handgrip 504.

Drive pawl 498 has a finger like base 510 that is generally planar in shape. Base 510 is formed with a through hole 512 that extends laterally, front to rear through the base. Formed integrally with and located above base 510, the driver pawl 498 has a crown 514, (FIG. 52B). Drive pawl 498 is shaped so that on proximally directed side the pawl, the crown tapers outwardly from the base. A through hole 516 extends laterally, front to rear, through crown 514. The crown 514 is further formed to have a J-shaped hook 518 (FIG. 53B). The hook 518 extends upwardly from the distal end of the crown 514 and is further oriented so that the pointed section thereof is directed proximally.

Handpiece 490 is constructed so that drive pawl 498 is slidably mounted to a post 519. The post 519 extends forward from the inner surface of the rear structural wall of the handpiece barrel 502. Specifically, the handpiece is assembled so that post 519 extends through pawl hole 516.

A drive arm 520, seen best in FIGS. 52B and 53B, is a first component internal to handpiece 490 capable of advancing the drive pawl 498 forward. Drive arm 520 is generally in the shape of an elongated rod. One end of the drive arm, the most distal end, is pivotally attached to the concealed section of the trigger 506 above the pivot pin 521. The proximal end of drive arm 520 is formed with a hook 522. The drive arm is positioned and the hook 522 shaped so that the drive arm hook 522 can engage the hook 518 integral with pawl 498.

Figure 52A:
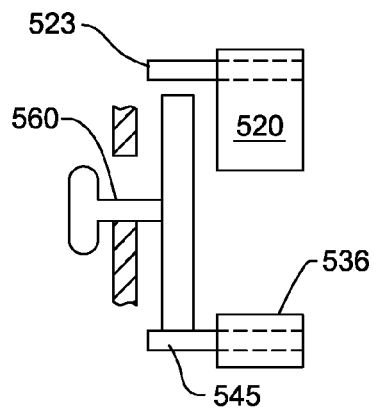
FIGS. 52A and 52B are, respectively, side and face views of how the control arm of the delivery assembly of FIG. 51 is set to configure the assembly so that it delivers a continues forward force to the push rod.
Figure 52B:
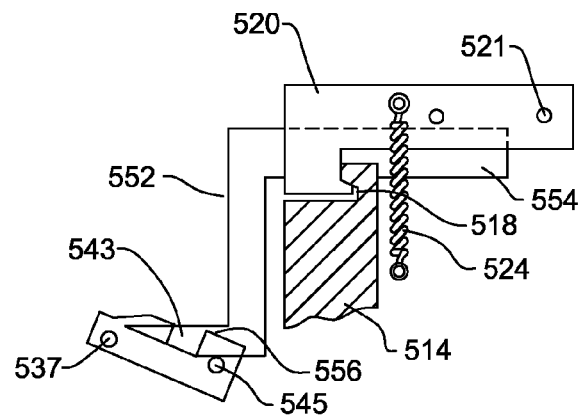

Drive arm 520 also includes a pin 523, best seen in FIG. 52A, that extends outwardly from the side of the rod towards the adjacent side wall of the barrel 502. A spring 524, shown only in FIG. 52B, is connected between the drive arm 520 and the barrel 502. Not identified are the posts integral with the barrel 502 and the drive arm 520 from which the spring 524 is suspended. Spring 524 is connected to between the barrel and drive arm to urge the drive arm downwardly. This downward positioning of the drive arm places the arm hook 522 in engagement with the drive pawl hook 518.

An impactor 526 is the second component internal to handpiece 490 capable of advancing pawl 498. Impactor 526 is in the form of solid block of metal. The impactor 526 is slidably mounted to a post 519 between the drive pawl and the rear wall of the barrel 502. The bore internal to the impactor through which post 519 extends not illustrated. While the impactor 526 is generally has a rectangular shape, a tab 530 is formed integrally therewith and extends downwardly from the impactor bottom surface. While not explicitly identified, it should be understood that tab 530 has a forward facing surface that extends perpendicularly downwardly from the base of the barrel. Tab 530 also has a rearwardly facing surface that is angled downwardly such as the distance from the base of the barrel increases, the surface extends toward the front of the handpiece 490.

A coil spring 528 is disposed over post 519 between the rear structural wall of the barrel 502 and the impactor 526. The coil spring 528 is designed to, when in the expanded state, hold the impactor 526 away from rear wall of the barrel 502. In some preferred versions of the invention, when spring 528 is fully extended, the spring urges the impactor into a position where it is able to engage its actuating drive finger 536 discussed below, A stop plate 531 is also part of handpiece 490. Stop plate 531 is fixedly mounted to the barrel 502 so as to be located over the distal end of pin 519. In some versions of the invention, plate 531 extends inwardly from an inner surface of one of the structural side walls of the barrel 502 (side wall not illustrated). The illustrated stop plate 531 is shown as having an opening (not identified). The opening is the void space internal to the stop plate in which the distal free end of post 519 is disposed.

A stop pin 533 is also provided. Stop post 533 is positioned adjacent pawl 498 to limit rearward movement of the pawl.

A drive link 534 and finger 536 cooperate to urge the impactor 526 rearwardly. Drive link 534 is shown as L-shaped bar. The elongated section of the link 534 is slidably mounted in the lower portion of the barrel. In the illustrated version of the invention, link 534 is shown sandwiched between the inner surface of the bottom structural wall of the barrel and a rail 538. The rail may be part of a structure that extends upwardly from the barrel bottom structural wall. The most distal end of the elongated section of the drive link is connected to the concealed section of the trigger 506 below pivot pin 508. A pin 540 connects the drive link 534 to the trigger 506. Pin 540 travels in an elongated slot 542 formed in the trigger 506 so that, as the trigger is retracted, the drive link will undergo a rearward linear motion.

The short section of the drive link 534 extends upwardly from the proximal end of the elongated section. Finger 536, now described by reference to FIGS. 52A and 53B, is pivotally connected to the free end of the drive link short section by a pivot pin 537. Finger 536 is shaped to have a notch 543 dimensioned to receive impactor tab 530. Finger 536 is further shaped to have a rearwardly directed surface 544 that extends diagonally upwardly.

Figure 53A:
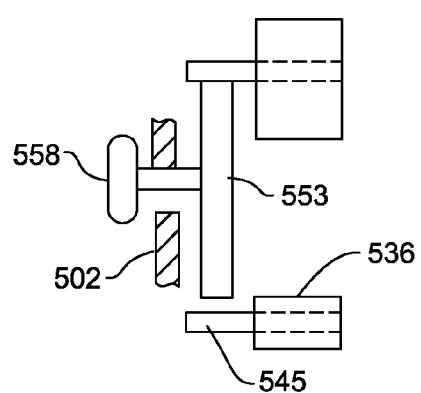
FIGS. 53A and 53B are, respectively, side and face views of how the control arm of the delivery assembly of FIG. 51 is set to configure the assembly so that it delivers a discreet, forward impact force to the push rod.
Figure 53B:
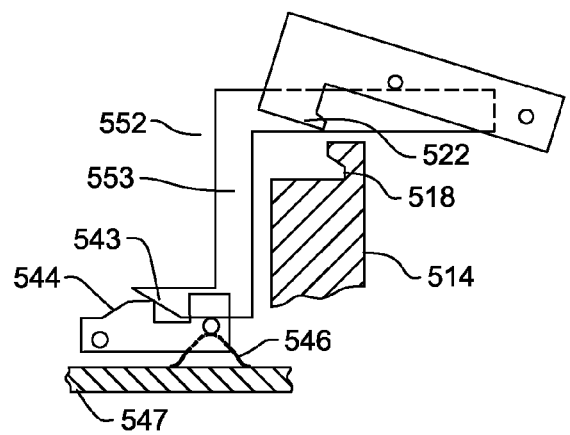

A second pin, pin 545, seen in FIGS. 52A and 53A, extends outwardly from finger 536 toward the adjacent structural side wall of the barrel 502. Pin 545 is seated against a leaf spring 546 seen only in FIG. 53B. Leaf spring 546 is mounted to a bar 547 that extends outwardly from the side wall of the barrel. Leaf spring 546 imposes a force on pin 545 that normally causes the pin 545 to hold the finger in the generally horizontal orientation. When finger 536 is so orientated, impactor tab 530 seats in finger notch 543.

A release pin 548 is mounted to the rear structural wall of the barrel 502. Release pin 548 is positioned so that when the finger 536 is retracted rearwardly, the pin will abut the diagonal surface 544 of the finger. In many preferred versions of the invention, the release pin 548 is threadedly mounted to the barrel 502. This allows the location along the path of travel of the finger at which the pin 544 abuts the finger to be selectively set.

A coil spring 550 normally holds the drive pawl 498 in its static state. Spring 550 extends between the inner surface of the front structural wall of the barrel 502 and the pawl base 510. The force spring 550 imposes on the drive pawl 498 normally places the pawl in a position wherein the pawl abuts stop post 533. When drive arm 520 is engaged with the pawl 498, this positioning of the pawl results in a like rearward positioning of the drive arm 520. When the drive arm 520 is so positioned, the drive arm pulls the portion of trigger 506 above 508 rearwardly. This causes the causes the exposed section of the trigger 506 to be in the forward position.

A spring 551 extends forwardly from the inner surface of the rear structural wall of the barrel 502. Spring 551 abuts drive link 534.

When drive arm 520 is disengaged from the drive pawl 498, finger 536 is engaged with the impactor 526. when the handpiece is so configured, spring 551 urges the drive link 534 forward. This displacement of the drive link 534 results in the like forward displacement of the exposed end of the trigger 506.

A control bar 552, now described by reference to FIGS. 52A, 52B, 53A and 53B, also disposed inside the barrel 502, sets which one of the drive arm 520 or finger 536 is engaged to cause the advancement of the drive pawl 498. Control bar 552 is in the form of three beams that are connected together as a single unit. There is a center beam 553 that generally extends vertically inside the barrel 502. More particularly the center beam 553 is mounted to rails (not shown) that allow the beam to slide vertically up and down. A top beam 554 extends distally forward from the top of the center beam 552. Beam 554 is of a sufficient length that the beam extends below drive arm pin 523. A bottom beam 556 extends proximally rearward from bottom of the center beam 553. Beam 556 is of sufficient length that it extends over finger pin 545. In the illustrated version of the invention top and bottom beams 556 are parallel. This need not always be the case.

The control bar 552 is mounted to the handpiece barrel 502 so that top beam 554 is located adjacent drive arm 520 and bottom beam 556 is adjacent finger 536. A control knob 558, located outside of the barrel 502, is connected to the bar center beam 552 by a post 560. Knob 558 is manually set to move the bar 552 up and down so as to control which component actuates the drive pawl 498.

Handpiece 490 is configured for use by loading an agglomeration of beads and cement in the delivery cannula 494. A push rod 496 is inserted into the handpiece barrel 502 through the rear end. Push rod 496 is passed through pawl through hole 510 and the center of spring 550. The distal end of the push rod is inserted into the proximal end opening of the delivery cannula. The push rod 496 is thus set for actuation by the drive pawl 498.

Control bar 552 is set in the lower of the two positions in order to cause the drive arm 520 to be the component that engages and actuates the drive pawl 498. When control bar 552 is so positioned, bottom beam 556 presses against finger pin 545. The force beam 556 places on the finger pin 545 overcomes the force leaf spring 546 places on the pin. Thus, pin 545 is pushed downwardly so as to result in the like diagonally downward pivoting of finger 536 around pivot pin 537. This pivoting of finger 536 serves to disengage impactor tab 530 from finger notch 543. When control bar 552 is so positioned, top beam 554 is spaced below pin 523. Spring 524 imposes a force on the drive arm 520 so as to urge the arm downwardly. This disposition of the drive arm 520 causes the drive arm hook 522 to engage pawl hook 518.

When trigger 506 of handpiece 490 of this invention is retracted toward handgrip 504, the trigger displaces the drive arm 520 forwardly and drive link 534 and finger 536 rearwardly. When the components internal to handpiece 490 are positioned as described above, since finger 536 and the trigger is retracted away from the impactor 526, this rearward displacement of the finger does not result in a like movement of the impactor. Neverthless, the drive arm 520 is engaged with the pawl 498. Consequently, forward movement of the drive arm 520 results in a like movement of the pawl 498. Thus, the manual force applied to the drive pawl through the trigger and drive arm overcomes the force imposed by spring 550. As a consequence of the forward movement of the drive pawl forward movement, the push rod becomes friction trapped in the pawl through hole 512. Consequently, the advancement of the drive pawl results in a like advancement of the push rod.

In this mode of operation, the push rod is continually advanced forwardly with the retraction of trigger 506. Once the trigger 506 undergoes its maximum rearward displacement, the practitioner releases his/her grip on the trigger. At this there no forces opposing the force placed on the pawl by spring 550. Spring 550 thus urges the pawl rearwardly. When the pawl is so displaced in its pivoted slightly. This pivoting repositions the pawl so that it no longer imposes a friction force of the push rod 496. Thus, when the pawl is rearwardly displaced by spring 550, the pawl does not cause the push rod to undergo a like displacement.

Alternatively, handpiece 490 is used to apply a sudden impact force against the push rod 496. This process starts with the resetting of control bar 552 to its top located position. The repositioning of the control bar 552 results in top beam 554 pressing against drive arm pin 523. The upward imposed by the beam 554 against the pin overcomes the downward force imposed by spring 524. The displacement of the top beam 554, through pin 523, thus pivots the drive arm diagonally upward. As a result of this displacement of the drive arm 520, arm hook 52 is rotated out of engagement with pawl hook 518.

The upwardly displacement of the control bar 552 results in the like movement of the lower beam 556. Lower beam 556 thus moves away from finger pin 545. Spring 546 is thus free to urge pin 545 and, by extension, the rest of finger 536 upwardly, into the horizontal position. The pivoting of the finger 536 back into this position results in the seating of the impactor tab 430 in the finger notch 543.

Push rod 496 is impact driven forward by the rearward pivoting of the trigger. This motion causes the previously described simultaneous forward movement of the drive arm 520 and rearward movement of finger 536. As described above, when the control bar 552 is in the impact position, the drive finger 520 is disengaged from the drive pawl 498. Therefore this forward displacement of the pawl has no effect on the pawl. However, the impactor tab 530 is seated in notch 543 of finger 536. Thus, the rearward displacement of the finger results in a like displacement of the impactor 526 along post 519. As a result of this displacement of the impactor 526, spring 528 compresses. Eventually, the finger 536 moves rearwardly to the point at which the tip of pin 548 strikes finger surface 544. The continued movement of the finger 536 against pin 548 results in the pin pivoting the finger downwardly around pin 537. This downward movement of finger 536 results in the finger disengaging from the impactor 526. Once this event occurs, the spring 528 is able to expand. The release of kinetic energy by the spring pushes the impactor 526. More specifically, spring 528 pushes the impactor forward with sufficient force and over a sufficient distance that the impactor is able to strike pawl crown 514 and push the pawl forward. Thus, the force imposed by spring 528 through the impactor 526 on the pawl 496 is sufficient to overcome the force imposed by spring 550. This sudden forward displacement of the pawl causes the push rod 496 to engage in a like sudden forward motion. This forward motion of the pawl 498 is limited by its abutment against stop plate 531.

It should be understood that the rearward motion of the drive link 534 results in compression of spring 551. When the drive finger 536 disengages from the impactor 526, spring 551 is free to work against the drive link 534. The forward displacement of the drive ling 534 by spring 551 results in two effects. First, the drive link 534 restores the trigger to the forward position. Secondly, the drive link 534 also moves the finger 536 back to its forward position so that the finger can reengage the impactor 526.

Handpiece 490 of this invention is thus able to apply a continual force to the push rod or a sudden force, an impact force. It is believed that when beads formed from plastic, including beads formed with plastic shells, are subjected to a sudden impact force, the force is more readily transferred as a shock wave through the beads to the surfaces against which the beads abut. The application of this force as a shock wave is believed to lessen the deformation of the beads. Instead the shock of this force is believed in some circumstances result in rapid compaction of the cancellous tissue so as facilitate the formation of a void space in the bone in which the implant can be formed.

XX. Fully And Partially Contained Bead Packages

As depicted by FIGS. 54A and 54B, it may be desirable in some versions of the invention to partially, if not fully encase the beads 20 forming the agglomeration. As seen in FIG. 54A, a set of two or more beads 20 can be loosely contained in a bag 570. Bag 570 is typically formed of a porous material through which the cement can flow. In the illustrated version of the invention, the bags 570 are elongated structure to facilitate the loading of the bags in the delivery cannula 18. Each bag 570 is provided front and rear with an end plate 572. When the loaded in the cannula, end plates 572 function as register members through which the pressure to advance the agglomeration is transferred to the downline beads. Also, while not illustrated, end plates can be provided with through holes. The through holes serves as channels through which cement or other fluent material forming the agglomeration can flow into each bag.

Also, in some versions of the invention, end plate Alternatively, as depicted in FIG. 54B, a bag 578 of this invention may be an open ended structure.

When an agglomeration including bead-containing bags of this invention is used, the material forming the bags allows the cement to flow into the interior of the bag. This cement flow is increased when open-ended bags 578 are employed. Since the beads 20 are not tightly packed in the bags, the bags do not appreciably limit the free movement of the beads so that the beads are not able to fully pack into the void space in which the implant is to be formed. Then once the bags with beads are in the void space so as to form the implant, the bags function as barriers that reduce the extravasious movement of cement out of the cavity in which the implant is to be formed.

The bags 570 and 578 are particularly useful in containing the beads 20 to prevent the beads 20 from straying to undesirable locations at the target site X. By providing the bags 570 and 578, multiple beads 20 may be connected together to limit the likelihood of a single element 12 being displaced to an undesirable location. It should be appreciated that any of the beads 20 previously described, in any size, and including any number (1 or more), could be used with the bags 570 and 578 to form a compound element.

The bags 570 and 578 may be formed entirely or in sections of a porous material, a non-porous material, a resorbable material, a non-resorbable material, a flexible material, a rigid or semi-rigid material, an expandable material, a non-expandable material, a radiopaque material, a radiolucent material, a radioactive material, or any combinations or substitutions thereof. The bags 570 and 578 may include a coating or coatings similar to the beads 20 described above and the beads 20 in the bags 570 and 578 may also include a similar or different coating or coatings. In some embodiments, the bags 570 and 578 may be formed of a material that begins to cure or harden upon exposure to blood, body fluids, UV, IR, or other natural or artificial catalysts placed in contact with the bags 570 and 578. The bags 570 and 578 may also hold such a material or be impregnated with such a material. For instance, the bags 570 and 578 may contain a powder component in addition to the beads 20 such that when mixed with body fluids, forms a flowable material capable of setting to a hardened condition.

Bags 570 and 578 may include one or more end plates 572. The end plates 15 may be flat or rounded. Some bags 570 and 578 may include only a single end plate 15 for closing a single open end of the bags 570 and 578, such as when the bags 570 and 578 includes a bag or sock having a single open end for filling the beads 20 in the bag or sock. The end plates 15 may include small bores such as shown in FIGS. 2O and 2R to allow the fluent material 18 to enter into the bags 570 and 578 or exit from the bags 570 and 578.

Loose beads 20 could also be placed between adjacent compound elements. Thus loose beads 20 could be mixed between the bags with beads.

The beads 20, including the compound elements (beads 20 in bags 570 and 578) are preferably sized to fit within a needle or cannula of 10 gauge or less, more preferably 12 gauge or less.

XXI. Alternative Agglomeration Delivery Assembly

Figure 55:
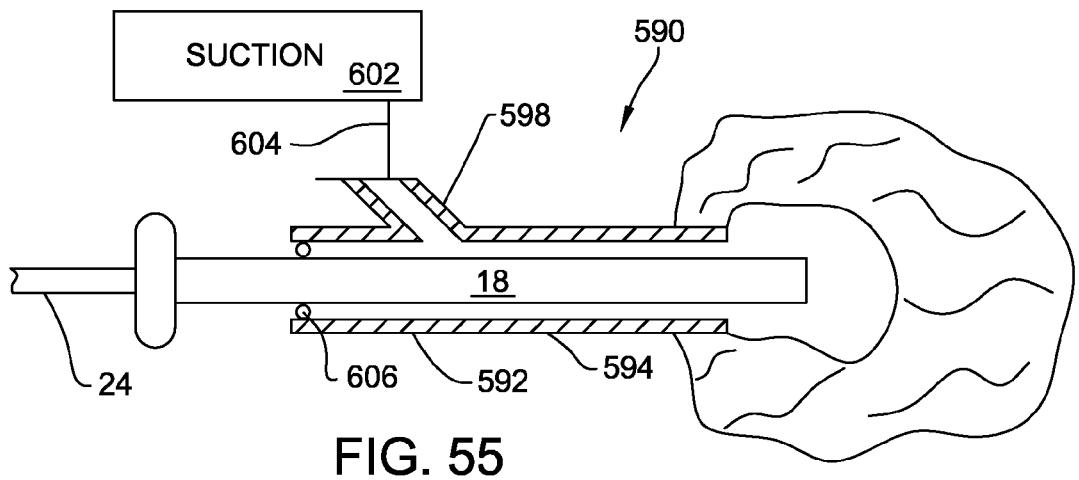
FIG. 55 is a cross sectional view of a delivery assembly of this invention with a return cannula.

FIG. 55 illustrates an alternative assembly 590 for delivering a bead and cement agglomeration into a bone 10 of this invention. Assembly 590 includes a return cannula 592 and, disposed therein, the delivery cannula 18. In some versions of the invention, the access cannula may function as the return cannula 592. The return cannula includes a tubular body 594.

Collectively the delivery cannula 18 and the return cannula 592 are shaped so that the delivery cannula 18 is disposed in the return cannula, there is a gap between the cannulae. In some versions of the invention, ribs (not illustrated) extend inwardly from the inner wall of the return cannula 592. The ribs center the delivery cannula 18 in the return cannula 592 to ensure that there is annular gap between the cannulae.

Adjacent the proximal end of the body 594-access cannula 590 has a suction fitting 598. Suction fitting 598 is dimensioned to receive a tube from a suction source 602. In the Figures, this tube is represented as a line 604. An O-ring 606 is fitted in the proximal end of the central lumen of the return cannula 592. The O-ring 606 forms a seal between the outside of the delivery cannula and the adjacent inner annular surface of the return cannula 592. In some versions of the invention, the return cannula is formed with an annular groove in the central lumen, (groove not illustrated). This groove is located adjacent the proximal end of the cannula 592. The O-ring 606 is seated in this grove so as to prevent the longitudinal movement of the O-ring when the delivery cannula is longitudinally displaced.

When Delivery assembly 590 of this invention is employed to inject a bone and cement agglomeration into the bone 10, both cannulae 18 and 592 are disposed within the bone. More particular, the assembly 590 is positioned so that the distal ends of both cannulae 18 and 592 are located in the space in which the implant is to be formed.

Using a push rod 24, the bead and cement agglomeration is injected into the bone. By selectively actuating the suction source 602, the pressure inside the cavity where the implant is being formed is regulated. Specifically, when the suction source 602 is actuated, a suction is drawn on the cavity through the conduit formed by the gap between and cannulae 20 and 592. This suction draws fluid, such a body fluids and uncured cement into this conduit. This fluid draw serves to cause the pressure inside the cavity to drop. An advantage of so regulating the cavity's pressure is that it reduces the likelihood that the cement will flow in an uncontrolled manner through other openings out of the bone.

In an alternative means by which this version of the invention can be practiced is to provide the delivery and return cannulae as two separate cannulae. An advantage of this version of the invention is that the cannulae can be independently positioned in the bone in which the implant is formed.

XXII. Second Alternative Agglomeration Delivery Assembly

Figure 56:
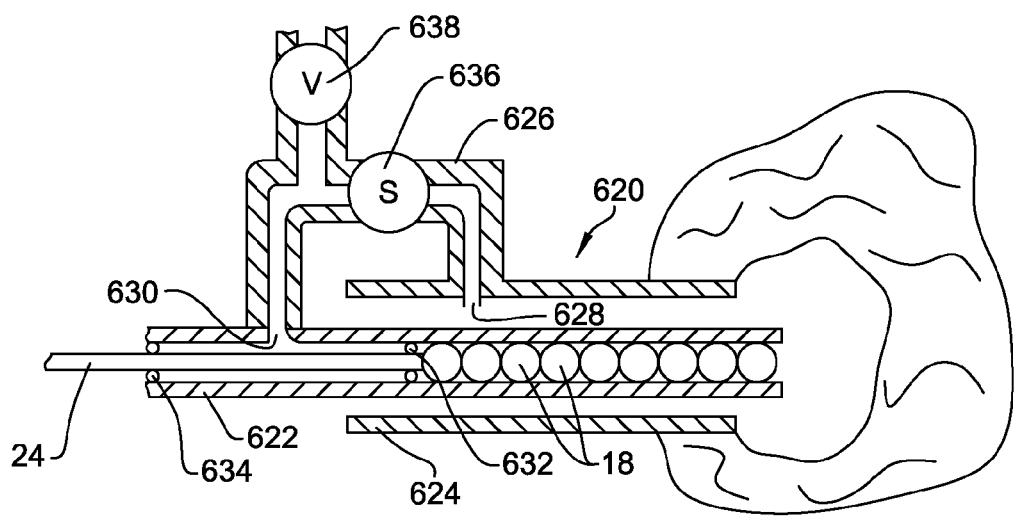
FIG. 56 is a cross sectional view of another delivery assembly of this invention with a return cannula.

Another assembly 620 for regulating pressure internal to the bone cavity is now described by reference to FIG. 56. Assembly 620 include concentric deliver and return cannulae 622 and 624, respectively. The cannulae are dimensioned relative to each other so that there is a gap between the outer surface of the delivery cannula 622 and the inner surface of the return cannula 624. The cannulae are further arranged so that typically the deliver cannula 622 projects a slight distance forward from the return cannula 624. A return line 626 extends between the cannula 622 and 624. Specifically, the return cannula 624 includes an outlet port 628 to which one end of the return line 626 is connected. Delivery cannula 622 has an inlet port 630 to which the second end of the return line is connected.

As in the previous described versions of the invention, a push rod 24 is employed to force the bead and cement agglomeration out of the delivery cannula 622. In this version of the invention, a first O-ring 632 is disposed around the distal end of the push rod. The O-ring 632 provides a seal between the push rod and the inner circumferential wall of the delivery cannula. The O-ring 632 is mounted to the push rod 24 to advance with the push rod. Thus, in some versions of the invention, O-ring 632 is seated between two annular spaced apart lips that extend circumferentially around the push rod immediately proximal to the distal end of the push rod (lips not illustrated). A second O-ring, O-ring 634, is also disposed in the delivery cannula 622. The O-ring 634 is located immediately forward of the proximal end of the push rod. The O-ring 634 serves as a static seal between the delivery cannula and the moving push rod 24.

Shown in line with return line 626 is a pressure sensor 636. A valve 638 to atmosphere is also shown connected to the return line 626.

When push rod 24 of assembly 620 of this invention is advanced to inject the agglomeration into the bone, O-ring 632 prevents the flow of cement proximally beyond the distal end of the O-ring. The O-ring 634 prevents the air from entering the delivery cannula 622 from the proximal end of the cannula. Thus, as the push rod is extended, a vacuum develops in the space around the section of the push rod disposed within the delivery cannula. This vacuum becomes a suction force that draws first through the return line and then through the gap between the cannula 622 and 624. This suction serves to draw at least a fraction of the cement discharged from the delivery cannula 622 back out of the bone cavity through the return cannula 624. The level of this suction is monitored with sensor 636. The level of suction can be set by adjusting valve 638.

In this version of the invention, as with assembly 590, the delivery cannula is typically positioned to extend forward of the return cannula. This prevents the cement that is discharged from the delivery cannula from immediately being drawn out of the bone cavity into the return cannula Delivery assembly 620 of this invention thus offers another means to reduce the pressure inside the bone cavity so as to minimize the extravasation of cement out of the bone. This assembly provides a means to so control pressure without requiring a separate suction unit.

XXIII ADDITIONAL EMBODIMENTS

The invention has been described in an illustrative manner, and it is to be understood that the terminology which has been used is intended to be in the nature of words of description rather than of limitation. Obviously, many modifications and variations of the present invention are possible in light of the above teachings, and the invention may be practiced otherwise than as specifically described.

Thus, not all features disclosed may be incorporated in all versions of the invention. Similarly, the various features of one or more versions of this invention may be incorporated into the features of other of the disclosed versions of the invention. Therefore, it is the object of the appended claims to cover all such variations and modifications that come within the true spirit and scope of this invention.

What is claimed is:

1. An assembly for forming an implant in a bone, said assembly comprising:
   a return cannula, said return cannula having a distal end, a proximal end opposite the distal end and being configured for insertion into the bone;
   a delivery cannula disposed within the return cannula, said delivery cannula having an open distal end, a proximal end opposite the distal end and being configured for insertion into a bone;
   one of an access cannula and a return line attached to the return cannula;
   an agglomeration of solid beads and cement contained within the delivery cannula; and
   a delivery mechanism attached to the proximal end of the delivery cannula, said delivery mechanism configured to urge the agglomeration out of the distal end of the delivery cannula,
   the one of the access cannula and the return line being configured to relieve excess fluid pressure within the bone by removing excess fluid within the return cannula, the excess fluid pressure being caused by delivering the agglomeration.

2. The assembly of claim 1, wherein said removal of excess fluid is performed by a suction fitting.

3. The assembly of claim 2, wherein the suction fitting is a tube.

4. The assembly of claim 1, wherein said removal of the excess fluid from the return cannula is by suction, which is regulated by a valve.

5. The assembly of claim 4, wherein the level of suction is monitored by a sensor.

6. The assembly of claim 1, wherein a center lumen of the return cannula contains a seal providing a seal between the inner wall of the return cannula and an outer wall of the delivery cannula.

7. The assembly of claim 6, wherein the seal is an O ring.

8. The assembly of claim 7, wherein an O ring is disposed around the distal end of the delivery mechanism.

9. The assembly of claim 8, wherein a second O ring is disposed in the proximal end of the delivery cannula around the delivery mechanism.

10. The assembly of claim 1, wherein the delivery cannula and the return cannula are separate cannulas.

11. The assembly of claim 1, wherein the delivery cannula and the return cannula are concentric.

12. The assembly of claim 1, wherein the delivery cannula further comprises an inlet connected to the return line.

13. The assembly of claim 1, wherein the inner wall of the return cannula has one or more longitudinal ribs extending inward towards the outer wall of the delivery cannula.

14. An assembly for forming an implant in a bone, said assembly comprising:
   a return cannula, said return cannula having a distal end, a proximal end opposite the distal end and being configured for insertion into the bone;
   a delivery cannula disposed within the return cannula, said delivery cannula having an open distal end, a proximal end opposite the distal end and being configured for insertion into a bone;
   one of an access cannula and a return line attached to the return cannula;
   the delivery cannula further comprising an inlet connected to the return line;
   an agglomeration of solid beads and cement contained within the delivery cannula; and
   a delivery mechanism attached to the proximal end of the delivery cannula, said delivery mechanism configured to urge the agglomeration out of the distal end of the delivery cannula,
   the one of the access cannula and the return line being configured to relieve excess fluid pressure within the bone by removing excess fluid within the return cannula, the excess fluid pressure being caused by delivering the agglomeration, wherein a center lumen of the return cannula contains a seal providing a seal between the inner wall of the return cannula and an outer wall of the delivery cannula.

15. An assembly for forming an implant in a bone, said assembly comprising:

- a return cannula, said return cannula having a distal end, a proximal end opposite the distal end and being configured for insertion into the bone;
- a delivery cannula disposed within the return cannula, said delivery cannula having an open distal end, a proximal end opposite the distal end and being configured for insertion into a bone;
- one of an access cannula and a return line attached to the return cannula;
- the delivery cannula further comprising an inlet connected to the return line;
- an agglomeration of solid beads and cement contained within the delivery cannula; and
- a delivery mechanism attached to the proximal end of the delivery cannula, said delivery mechanism configured to urge the agglomeration out of the distal end of the delivery cannula,
- the one of the access cannula and the return line being configured to relieve excess fluid pressure within the bone by removing excess fluid within the return cannula, the excess fluid pressure being caused by delivering the agglomeration, wherein the delivery cannula and the return cannula are concentric.

* * * * *